United States Patent [19]

Billheimer et al.

[11] Patent Number: 5,166,214

[45] Date of Patent: Nov. 24, 1992

[54] USE OF IMIDAZOLES FOR THE TREATMENT OF ATHEROSCLEROSIS

[75] Inventors: Jeffrey T. Billheimer, West Chester, Pa.; Peter J. Gillies, Hockessin, Del.; C. Anne Higley, Newark, Del.; Thomas P. Maduskuie, Jr.; Ruth R. Wexler, both of Wilmington, Del.

[73] Assignee: Du Pont Merck Pharmaceutical Company, Wilmington, Del.

[21] Appl. No.: 533,241

[22] Filed: Jun. 4, 1990

Related U.S. Application Data

[63] Continuation-in-part of Ser. No. 416,606, Oct. 10, 1989, abandoned, which is a continuation-in-part of Ser. No. 279,981, Dec. 5, 1988, abandoned.

[51] Int. Cl.$^5$ .................. A61N 31/415; C07D 233/66
[52] U.S. Cl. .................................... 514/341; 514/398; 546/278; 548/315.1; 548/315.7; 548/324.1
[58] Field of Search ................ 548/337, 336; 514/398, 514/341; 546/278

[56] References Cited

U.S. PATENT DOCUMENTS

| | | | |
|---|---|---|---|
| 3,950,353 | 4/1976 | Durant | 548/342 |
| 4,228,291 | 10/1980 | Durant et al. | 514/256 |
| 4,413,130 | 11/1983 | White | 548/342 |
| 4,460,598 | 7/1984 | Lautenschlager et al. | 548/138 |
| 4,623,662 | 11/1986 | DeVries | 514/596 |
| 4,654,358 | 3/1987 | Lautenschlager et al. | 548/336 |
| 4,722,927 | 2/1988 | Holmes | 514/256 |

FOREIGN PATENT DOCUMENTS 3504679  8/1986  Fed. Rep. of Germany.
3504680  8/1986  Fed. Rep. of Germany.

Primary Examiner—Alan L. Rotman
Assistant Examiner—Catherine S. Kilby Scalzo
Attorney, Agent, or Firm—Gildo E. Fato; Annette L. Richter

[57] ABSTRACT

This invention relates to imidazoles as inhibitors of acyl-CoA: cholesterol acyltransferase (ACAT), processes for their preparation, and their use as antihypercholesterolemic agents or antiatherosclerotic.

10 Claims, No Drawings

USE OF IMIDAZOLES FOR THE TREATMENT OF ATHEROSCLEROSIS

CROSS-REFERENCE TO RELATED APPLICATION

This application is a continuation-in-part of U.S. Ser. No. 07/416,606 filed Oct. 10, 1989 abandoned, which is a continuation-in-part of U.S. Ser. No. 07/279,981 abandoned, filed Dec. 5, 1988, both of which are incorporated herein by reference.

FIELD OF THE INVENTION

This invention relates to imidazoles as inhibitors of acyl-CoA: cholesterol acyltransferase (ACAT), pharmaceutical compositions containing them, processes for their preparation, and their use as antihypercholesterolemic and/or antiatherosclerotic agents.

BACKGROUND OF THE INVENTION

Hypercholesterolemia is an established risk factor in the development of atherosclerosis. Therapeutic agents which control the level of serum cholesterol have proven to be effective in the treatment of coronary artery disease. While agents exist that can modulate circulating levels of cholesterol carrying lipoproteins, these agents have little or no effect on the intestinal absorption of cholesterol. Dietary cholesterol can increase the level of serum cholesterol to levels which place an individual at increased risk for the development or exacerbation of atherosclerosis. Since much of the free or unesterified cholesterol that is absorbed by intestinal mucosal cells must first be esterified by ACAT prior to its incorporation and secretion into the bloodstream in large lipoprotein particles called chylomicrons, inhibition of ACAT can reduce the absorption of dietary cholesterol. In addition, the accumulation and storage of cholesteryl esters in the arterial wall is associated with increased activity of ACAT. Inhibition of the enzyme is expected to inhibit the formation or progression of atherosclerotic lesions in mammals.

There are a limited number of patents in the literature disclosing compounds which are useful as ACAT inhibitors in particular and antiatherosclerotic agents in general. For example, U.S. Pat. No. 4,623,662, issued to De Vries on Nov. 18, 1986, discloses ureas and thioureas as ACAT inhibitors useful for reducing the cholesterol ester content of an arterial wall, inhibiting atherosclerotic lesion development, and/or treatment of mammalian hyperlipidemia. U.S. Pat. No. 4,722,927, issued to Holmes on Feb. 2, 1988, discloses disubstituted pyrimidineamides of oleic and linoleic acids as ACAT inhibitors useful for inhibiting intestinal absorption of cholesterol.

U.S. Pat. No, 4,460,598, issued to Lautenschlager et al. on Jul. 17, 1984, discloses compounds of the formula:

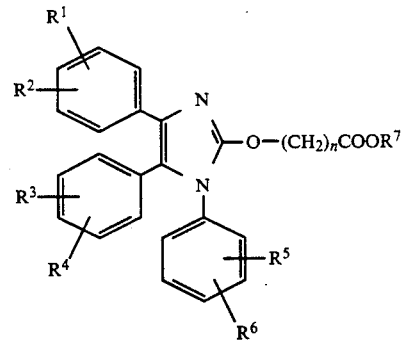

wherein
$R^1$, $R^2$, $R^3$, $R^4$, $R^5$ and $R^6$ independently are H, F, Cl, Br, I, alkyl, alkoxy, or $CF_3$, with the proviso that one or several of $R^1$ and $R^2$, $R^3$ and $R^4$, or $R^5$ and $R^6$ taken together represent methylenedioxy;
$R^7$ is H, alkali metal ion, alkyl of 1 to 6 carbon atoms, or benzyl; and
n is 0 to 10.

The synthesis and the use of these compounds in the treatment of thromboembolic, inflammatory and/or atherosclerotic diseases is disclosed.

U.S. Pat. No. 4,654,358, issued to Lautenschlager et al. on Mar. 31, 1987, discloses compounds of the formula:

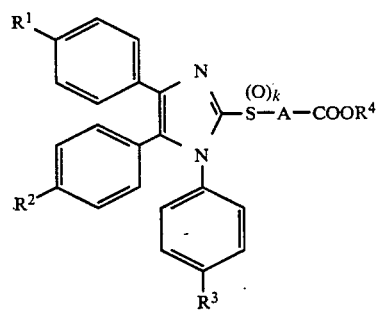

wherein
k is 0, 1, or 2,
$R^1$, $R^2$ and $R^3$ independently are H, F, Cl, $CH_3$, $CH_3O$, or $CF_3$;
$R^4$ is H, Na, K, $CH_3$, $CH_3CH_2$, $(CH_3)_2CH$, $CH_3(CH_2)_2$, or butyl;
A is $C(CH_3)_2$, $CH(CH_2)_mCH_3$, $(CH_2)_n$, or $(CH_2)_{n-2}CH(CH_3)$;
m is 0 to 8; and
n is 2 to 10.

The synthesis and the use of these compounds in the treatment of inflammatory diseases, diseases of lipid metabolism, and/or hyperlipidemic diseases is disclosed.

German Laid Open Application No. DE 3504679, Lautenschläger et al., published Aug. 14, 1986, discloses compounds of the formula:

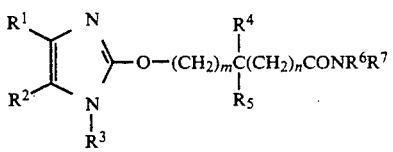

wherein
R$^1$, R$^2$ and R$^3$ independently are H, alkyl of 1 to 6 carbon atoms, cycloalkyl of 1 to 6 carbon atoms, or

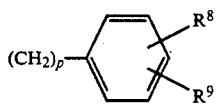

R$^4$ and R$^5$ independently are H, C$_6$H$_5$, or alkyl or 1 to 9 carbon atoms;
R$^6$ and R$^7$ independently are H, OH, saturated or unsaturated alkyl, cycloalkyl, or hydroxyalkyl of 1 to 10 carbon atoms,

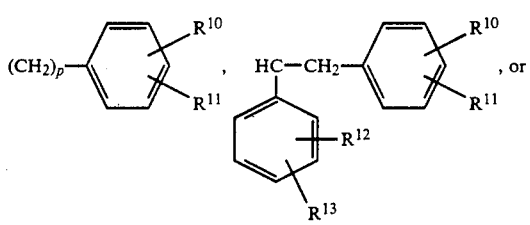

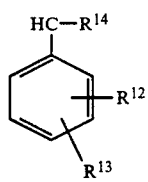

R$^8$, R$^9$, R$^{10}$, R$^{11}$, R$^{12}$ and R$^{13}$ independently are H, F, Cl, Br, NO$_2$, CH$_3$CONH, OH, alkyl of 1 to 3 carbon atoms, CF$_3$, and alkoxy of 1 to 3 carbon atoms, with the proviso that R$^8$ and R$^9$, R$^{10}$ and R$^{11}$, or R$^{12}$ and R$^{13}$ taken together represent methylenedioxy;
R$^{14}$ is alkyl of 1 to 2 carbon atoms;
m and n taken together represent a whole number from 0 to 9;
p is 0 to 2;
s is 0 to 2; and
t is 0 or 2.

The synthesis and the use of these compounds in the treatment of thromboembolic, inflammatory, atherosclerotic, and lipid metabolism diseases in general is disclosed.

German Laid Open Application No. DE 3504680, Lautenschläger et al., published Aug. 14, 1986, discloses compounds of the formula:

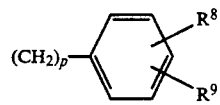

wherein
R$^1$, R$^2$ and R$^3$ independently are H, alkyl of 1 to 6 carbon atoms, cycloalkyl of 1 to 6 carbon atoms, or

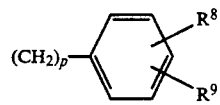

R$^1$ and R$^2$ can be taken together with the carbon atoms in the 4 and 5 position of the imidazole ring to represent a carbocyclic five- or six-membered aromatic or partially hydrogenated ring which may be substituted by R$^8$ or R$^9$;
R$^4$ and R$^5$ independently are H, C$_6$H$_5$, or alkyl of 1 to 9 carbon atoms;
R$^6$ is alkyl, cycloalkyl, or hydroxyalkyl of 1 to 20 carbon atoms, H, alkali metal if X is —COO—, 1-phenethyl, or

[structure with C$_s$H$_{2s-t}$ and R$^{10}$, R$^{11}$]

R$^7$ is H, OH if X is —CONR$^7$—, or alkyl of 1 to 4 carbon atoms;
R$^8$, R$^9$, R$^{10}$ and R$^{11}$ are independently H, Cl, F, Br, NO$_2$, CH$_3$CONH, OH, alkyl of 1 to 3 carbon atoms, CF$_3$, or alkoxy of 1 to 3 carbons, or R$^8$ and R$^9$ or R$^{10}$ and R$^{11}$ taken together represent methylenedioxy;
X is a bond, O, OC(=O)O, C(=O)O, CONR$^7$, OC(=O), or OC(=O)NR$^7$;
m and n taken together represent a whole number from 0 to 9;
p is 0 to 2;
s is 0 to 2; and
t is 0 or 2.

The synthesis and the use of these compounds in the treatment of thromboembolic, inflammatory, atherosclerotic, and lipid metabolism diseases in general is disclosed.

Durant et al., U.S. Pat. No. 4,228,291, issued Oct. 14, 1980, teaches compounds of the formula:

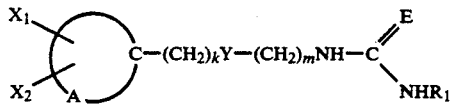

wherein A together with the carbon atom form an unsaturated heterocyclic nucleus which may be an imidazole, pyrazole, pyrimidine, pyrazine, pyridazine, thiazole, isothiazole, oxazole, isoxazole, triazole, thiadiazole, benzimidazole, or 5,6,7,8-tetrahydroimidazol[1,5- a]pyridine ring; $X_1$ is H, lower alkyl, hydroxyl, trifluoromethyl, benzyl, halogen, amino, or

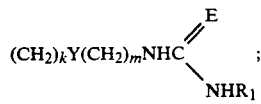

$X_2$ is H, or when $X_1$ is lower alkyl, lower alkyl or halogen; k is 0 to 2 and m is 2 or 3, provided that the sum of k and m is 3 or 4; Y is O, S, or NH; E is $NR_2$; $R_1$ is H, lower alkyl or di-lower alkyl amino-lower alkyl; and $R_2$ is H, nitro, or cyano. The compounds are said to be antihistamines of the $H_2$ receptor blocking type, as well as having anti-inflammatory activity.

White, U.S. Pat. No. 4,413,130, Nov. 1, 1983, discloses histamine $H_2$ receptor antagonists of the formula:

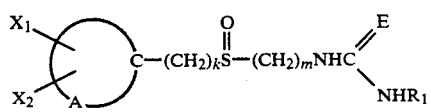

where A together with the carbon atom form an unsaturated heterocyclic nucleus which may be an imidazole, pyridine, thiazole, isothiazole, oxazole, isoxazole, pyrazole, triazole, thiadiazole, pyrimidine, pyrazine or pyridazine; $X_1$ and $X_2$ may be H, lower alkyl, trifluoromethyl, hydroxyl, halogen, amino, or $X_1$ and $X_2$ and at least two of the atoms comprising A may form a further ring; k is 0 to 2 and m is 2 or 3, provided that the sum of k and m is 3 or 4; E is O, S, or $NR_2$; $R^1$ is H, lower alkyl, acyl, or dialkylaminoalkyl; and $R_2$ is H, $NO_2$, CN, alkansulphonyl or arenesulphonyl.

There are no known literature references disclosing the imidazoles of this invention, their use as ACAT inhibitors, or their use to lower cholesterol or in the treatment of atherosclerosis.

The compounds of this invention are very potent ACAT inhibitors. As shown by the data presented below in Table 6, the compounds of this invention inhibit ACAT activity in vitro with at least ten times the potency of any ACAT inhibitors described in the current literature. As shown by the data presented below in Table 8, the compounds of this invention cause a reduction in the serum cholesterol level in cholesterol-fed hamsters. The compounds of this invention are thus expected to be useful in pharmaceutical formulations for the treatment of atherosclerosis. The compounds of this invention have been shown to lower serum cholesterol, and this invention should not be construed as limited to any particular antihypercholesterolemic mechanism of action.

SUMMARY OF THE INVENTION

The present invention provides novel compounds of Formula (I), processes for their preparation, pharmaceutical compositions containing such imidazoles, and therapeutic methods for their use as antihypercholesterolemic and/or antiatherosclerotic agents.

This invention provides compounds of Formula (I):

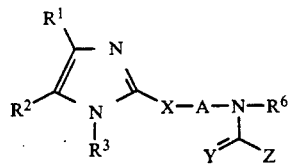

wherein
$R^1$ and $R^2$ are selected independently from H, $C_1$-$C_8$ alkyl, $C_3$-$C_8$ branched alkyl, $C_3$-$C_7$ cycloalkyl, $C_4$-$C_{10}$ cycloalkylalkyl, $C_7$-$C_{14}$ araalkyl, 2-, 3- or 4-pyridinyl, 2-thienyl, 2-furanyl, phenyl optionally substituted with 1 to 3 groups selected from F, Cl, Br, OH, $C_1$-$C_4$ alkoxy, $C_1$-$C_4$ alkyl, $C_3$-$C_8$ branched alkyl, $CH_3S(O)_r$, $NO_2$, $CF_3$, or $NR^7R^8$; or
$R^1$ and $R^2$ can also be taken together as

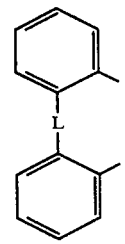

where L is O, $O(CH_2)_{m+1}O$, or $(CH_2)_m$ where m is 0-4;
$R^3$ is H, $C_1$-$C_6$ alkyl, allyl, benzyl, or phenyl optionally substituted with F, Cl, $CH_3$, $CH_3O$, or $CF_3$;
$R^4$ is straight chain $C_1$-$C_8$ alkyl optionally substituted with F; $C_3$-$C_8$ branched alkyl, $C_3$-$C_7$ cycloalkyl, $C_4$-$C_{10}$ cycloalkylalkyl, $C_7$-$C_{14}$ araalkyl where the aryl group is optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^7R^8$, or $NCOR^7$; $C_3$-$C_6$ alkenyl or alkynyl, $C_1$-$C_3$ perfluoroalkyl, phenyl optionally substituted with 1 to 3 groups selected from $C_1$-$C_4$ alkyl, $C_3$-$C_8$ branched alkyl, $C_1$-$C_4$ alkoxy, F, Br, Cl, $NH_2$, OH, CN, $CO_2H$, $CF_3$, $NO_2$, $C_1$-$C_4$ carboalkoxy, $NR^7R^8$ or $NCOR^7$; pentafluorophenyl, benzyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^7R^8$, or $NCOR^7$; 2-, 3- or 4- pyridinyl, pyrimidinyl, or biphenyl;
$R^5$ is H, $C_1$-$C_6$ alkyl, or benzyl;
$R^6$ is $C_1$-$C_8$ alkyl, $C_3$-$C_8$ branched alkyl, $C_3$-$C_7$ cycloalkyl, $C_3$-$C_8$ alkenyl or alkynyl, phenyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^7R^8$, or $NCOR^7$; pentafluorophenyl, benzyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^7R^8$, or $NCOR^7$;
$R^7$ and $R^8$ are selected independently from H or $C_1$-$C_4$ alkyl;
X is $S(O)_r$, O, $NR^5$, $CH_2$;
A is $C_2$-$C_{10}$ alkyl, $C_3$-$C_{10}$ branched alkyl, $C_3$-$C_{10}$ alkenyl, or $C_3$-$C_{10}$ alkynyl;

Y is O, S, H$_2$, NH;
Z is NHR$^4$, OR$^4$, or R$^4$;
r is 0-2,
or a pharmaceutically acceptable salt thereof.

Preferred are compounds of Formula (I) wherein:
R$^1$ and R$^2$ are selected independently from C$_1$-C$_8$ alkyl, C$_3$-C$_8$ branched alkyl, C$_3$-C$_7$ cycloalkyl, C$_4$-C$_{10}$ cycloalkylalkyl, C$_7$-C$_{14}$ araalkyl, 2-, 3-, or 4-pyridinyl, 2-thienyl, 2-furanyl, phenyl optionally substituted with 1 to 2 groups selected from F, Cl, Br, OH, C$_1$-C$_4$ alkoxy, C$_1$-C$_4$ alkyl, C$_3$-C$_8$ branched alkyl, CH$_3$S(O)$_r$, NO$_2$, or NR$^7$R$^8$; or
R$^1$ and R$^2$ can also be taken together as

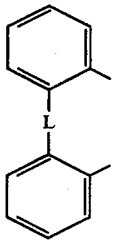

where L is O, O(CH$_2$)$_{m+1}$O, or (CH$_2$)$_m$ where m is 0-4.

More preferred are Compounds of Formula (I) wherein:
R$^3$ is H, CH$_3$, phenyl;
R$^6$ is C$_1$-C$_8$ alkyl, C$_3$-C$_8$ branched alkyl, C$_3$-C$_7$ cycloalkyl, phenyl optionally substituted with 1 to 3 groups selected from CH$_3$, CH$_3$O, F, Br, Cl, NH$_2$, OH, CN, CO$_2$H, CF$_3$, or di(C$_1$-C$_4$)alkylamino; or benzyl optionally substituted with 1 to 3 groups selected from CH$_3$, CH$_3$O, F, Br, Cl, NH$_2$, OH, CN, CO$_2$H, CF$_3$, or di(C$_1$-C$_4$)alkylamino;
X is S(O)$_r$, CH$_2$;
A is C$_2$-C$_{10}$ alkyl, C$_4$-C$_9$ branched alkyl.

More specifically preferred because of their biological activity are compounds of Formula (I) wherein:
R$^1$ and R$^2$ are selected independently from C$_1$-C$_8$ alkyl, C$_3$-C$_8$ branched alkyl, C$_3$-C$_7$ cycloalkyl, C$_4$-C$_{10}$ cycloalkylalkyl, C$_7$-C$_{14}$ araalkyl, 2-, 3-, or 4-pyridinyl, 2-thienyl, or phenyl optionally substituted with 1 to 2 groups selected from F, Br, Cl, C$_1$-C$_4$ alkyl, C$_3$-C$_8$ branched alkyl, CH$_3$O, CH$_3$S(O)$_r$, NO$_2$, or di(C$_1$-C$_4$)alkylamino; or
R$^1$ and R$^2$ can also be taken together as

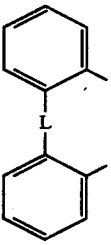

where L is O or OCH$_2$O;
R$^3$ is H;
R$^4$ is C$_1$-C$_8$ alkyl, C$_3$-C$_8$ branched alkyl, C$_3$-C$_7$ cycloalkyl, C$_4$-C$_{10}$ cycloalkylalkyl, C$_7$-C$_{14}$ araalkyl, phenyl substituted with 1 to 3 groups selected from CH$_3$, F, Cl, CH$_3$O, CN; or benzyl optionally substituted with 1 to 3 groups selected from CH$_3$, CH$_3$O, F, Cl, or CN;
R$^6$ is C$_1$-C$_8$ alkyl or phenyl optionally substituted with 1 to 3 groups selected from CH$_3$, CH$_3$O, F, Cl, or CN;
A is C$_4$-C$_9$ alkyl;
X is S(O)$_r$.

Specifically preferred are:
N'-(2,4-difluorophenyl)-N-[5-(4,5-diphenyl-1H-imidazol-2-ylthio)pentyl]-N-heptylurea
N-[5-(4,5-diphenyl-1H-imidazol-2-ylthio)pentyl]-N-heptyl-N'-phenylurea
N'-(2,4-difluorophenyl)-N-[8-(4,5-diphenyl-1H-imidazol-2-ylthio)octyl]-N-heptylurea
N-butyl-N'-(2,4-difluorophenyl)-N-[8-(4,5-diphenyl-1H-imidazol-2-ylthio)octyl]urea
N'-(2,4-dimethoxyphenyl)-N-[5-(4,5-diphenyl-1H-imidazol-2-ylthio)pentyl]-N-heptylurea
N-[5-(4,5-diphenyl-1H-imidazol-2-ylthio)pentyl]-N-heptyl-N'-methylurea
N-[5-(4,5-diphenyl-1H-imidazol-2-ylthio)pentyl]-N-heptyl-N'-propylurea
N'-(2,4-difluorophenyl)-N-[5-[(4,5-diphenyl-1H-imidazol-2-yl)sulfonyl]pentyl]-N-heptylurea
N-[5-(4,5-diphenyl-1H-imidazol-2-ylthio)pentyl]-N'-(3-fluorophenyl)-N-heptylthiourea
N-[5-(4,5-diphenyl-1H-imidazol-2-ylthio)pentyl]-N'-(3-fluorophenyl)-N-heptylurea
N'-(2,4-difluorophenyl)-N-heptyl-N-[5-(4-phenyl-1H-imidazol-2-ylthio)pentyl]urea
N-[5-(4,5-diphenyl-1H-imidazol-2-ylthio)pentyl]-N-heptyl-N'-(2,4,6-trifluorophenyl)thiourea
N'-(2,6-dichlorophenyl)-N-[5-(4,5-diphenyl-1H-imidazol-2-ylthio)pentyl]-N-heptylurea
N-[5-(4,5-diphenyl-1H-imidazol-2-ylthio)pentyl]-N-heptyl-N'-(1-methylethyl)urea
N-[5-(4,5-diphenyl-1H-imidazol-2-ylthio)pentyl]-2,4-difluoro-N-heptylbenzeneacetamide
N-[5-(4,5-diphenyl-1H-imidazol-2-ylthio)pentyl]-N-heptyl-N'-propylthiourea
N-[5-(4,5-diphenyl-1H-imidazol-2-ylthio)pentyl]-N-heptyl-N'-octylurea
N'-cyclohexyl-N-[5-(4,5-diphenyl-1H-imidazol-2-ylthio)pentyl]-N-heptylurea
N'-(2,4-difluorophenyl)-N-[5-[(4,5-diphenyl-1H-imidazol-2-yl)sulfinyl]pentyl]-N-heptylurea
N'-(2,4-difluorophenyl)-N-[2-(4,5-diphenyl-1H-imidazol-2-ylthio)ethyl]-N-heptylurea
N-[5-(4,5-diphenyl-1H-imidazol-2-ylthio)pentyl]-N-heptylbutanamide
N-[5-[4,5-bis(4-methoxyphenyl)-1H-imidazol-2-ylthio]pentyl]-N'-(2,4-difluorophenyl)-N-heptylurea
N-[5-[4,5-bis(1-methylethyl)-1H-imidazol-2-ylthio]pentyl]-N'-(2,4-difluorophenyl)-N-heptylurea
N'-(2,4-difluorophenyl)-N-[5-(4,5-dipropyl-1H-imidazol-2-ylthio)pentyl]-N-heptylurea
N-[5-[4,5-bis(4-fluorophenyl)-1H-imidazol-2-ylthio]pentyl]-N'-(2,4-difluorophenyl)-N-heptylurea
N-[5-(1H-dibenz[2,3:6,7]oxedino[4,5-d]imidazol-2-ylthio)pentyl]-N'-(2,4-difluorophenyl)-N-heptylurea
N-[5-[4,5-bis(2-thienyl)-1H-imidazol-2-ylthio]pentyl]-N'-(2,4-difluorophenyl)-N-heptylurea
N-[5-(4,5-diphenyl-1H-imidazol-2-ylthio)pentyl]-N-heptylpentanamide
N-[5-(4,5-diphenyl-1H-imidazol-2-ylthio)pentyl]-N-heptyl[1,1'-biphenyl]-4-acetamide
N-[5-(4,5-diphenyl-1H-imidazol-2-ylthio)pentyl]-N-heptyl-N'-(2,4,6-trifluorophenyl)urea N-[5-[4,5-bis(2-pyridinyl)-1H-imidazol-2-ylthio]pentyl]-N'-(2,4-difluorophenyl)-N-heptylurea N'-(2,4-difluorophenyl)-N-[6-(4,5-diphenyl-1H-imidazol-2-yl)hexyl]-N-heptylurea N-[5-[4,5-bis(4-methylphenyl)-1H-imidazol-2-ylthio]-pentyl]-N'-(2,4-difluorophenyl)-N-heptylurea N-[5-[4,5-bis(4-methoxyphenyl)-1H-imidazol-2-ylthio]-pentyl]-N-heptylbutanamide N-[5-[4,5-bis(4-hydroxyphenyl)-1H-imidazol-2-ylthio]-pentyl]-N'-(2,4-difluorophenyl)-N-heptylurea N-[5-[4,5-bis(1-methylethyl)-1H-imidazol-2-ylthio]pentyl]-N-heptylcyclohexaneacetamide N-[5-[4,5-bis(3-methoxyphenyl)-1H-imidazol-2-ylthio]-pentyl]-N'-(2,4-difluorophenyl)-N-heptylurea N-[5-[4,5-bis(2-methoxyphenyl)-1H-imidazol-2-ylthio]-pentyl]-N'-(2,4-difluorophenyl)-N-heptylurea N'-[(1,1'-biphenyl)-4-yl]-N-[5-(4,5-diphenyl-1H-imidazol-2-ylthio)pentyl]-N-heptylurea N-(2,4-difluorophenyl)-N-[5-(4,5-diphenyl-1H-imidazol-2-ylthio)pentyl]-N'-octylurea Propyl [5-(4,5-diphenyl-1H-imidazol-2-ylthio)pentyl]-heptylcarbamate (Phenylmethyl) [5-(4,5-diphenyl-1H-imidazol-2-ylthio)-pentyl]heptylcarbamate Phenyl [5-(4,5-diphenyl-1H-imidazol-2-ylthio)pentyl]-heptylcarbamate (2-Methylpropyl) [5-(4,5-diphenyl-1H-imidazol-2-ylthio)pentyl]heptylcarbamate Ethyl [5-(4,5-diphenyl-1H-imidazol-2-ylthio)pentyl]-heptylcarbamate Octyl [5-(4,5-diphenyl-1H-imidazol-2-ylthio)pentyl]-heptylcarbamate N-[5-[4,5-bis[4-(dimethylamino)phenyl]-1H-imidazol-2-ylthio]pentyl]-N'-(2,4-difluorophenyl)-N-heptylurea N-[5-(4,5-dicyclohexyl-1H-imidazol-2-ylthio)pentyl]-N'-(2,4-difluorophenyl)-N-heptylurea (4-fluorophenyl)[5-(4,5-diphenyl-1H-imidazol-2-ylthio)-pentyl]heptylcarbamate N-[5-(4,5-diphenyl-1H-imidazol-2-ylthio)pentyl]-N'-octyl-N-phenylurea N-[5-(1H,9H-dibenz[4,5:8,9][1,3]dioxonino[6,7-d]imidazol-2-ylthio)-pentyl]-N'-(2,4-difluorophenyl)-N-heptylurea N'-(4-cyanophenyl)-N-[5-(4,5-diphenyl-1H-imidazol-2-ylthio)pentyl]-N-heptylurea N-[5-[4,5-bis(4-methoxyphenyl)-1H-imidazol-2-ylthio]-pentyl]-2,4-difluoro-N-heptylbenzeneacetamide Phenyl [5-[4,5-bis(4-(dimethylamino)phenyl)-1H-imidazol-2-ylthio]pentyl]heptylcarbamate N-[5-[4,5-bis(4-methoxyphenyl)-1H-imidazol-2-ylthio]-pentyl]-N-heptyl-N'-(1-methylethyl)urea N-[5-[4,5-bis[4-(dimethylamino)phenyl]-1H-imidazol-2-ylthio]pentyl]-N-heptyl-N'-(1-methylethyl)urea or a pharmaceutically acceptable salt thereof.

DETAILED DESCRIPTION OF THE INVENTION

Synthesis

The novel compounds of Formula (I) may be prepared using the reactions and techniques described in this section. The reactions are performed in solvents appropriate to the reagents and materials employed and suitable for the transformation being effected. It is understood by those skilled in the art of organic synthesis that the functionality present on the imidazole and other portions of the molecule must be compatible with the reagents and reaction conditions proposed. Not all compounds of Formula (I) falling into a given class may be compatible with some of the reaction conditions required in some of the methods described. Such restrictions to the substituents which are compatible with the reaction conditions will be readily apparent to one skilled in the art and alternative methods described must then be used.

The compounds of Formula (I) wherein X is O, S or NH can be prepared by the route shown in Scheme 1. The esters of Formula (3) wherein X is O or S can be prepared by converting the requisite 4-imidazolin-2-one (1) where X is O, or 4-imidazolin-2-thione (1) where X is S, into the corresponding alkali metal salt by addition of a base such as sodium hydride, and the salt is alkylated with a compound of the formula M-(A')CO$_2$R, wherein R is CH$_3$ or C$_2$H$_5$, M is a halogen or a tosylate group, and A' is a moiety having one less methylene group than A, in a polar solvent such as N,N-dimethylformamide. Alternatively, the esters of Formula (3) wherein X is S may be prepared by direct alkylation of the requisite 4-imidazolin-2-thione with M-(A')CO$_2$R, without the addition of a suitable base, in a polar solvent such as N,N-dimethylformamide at a temperature from ambient temperature to the reflux temperature of the solvent. The esters of Formula (3) wherein X is NH can be prepared by the reaction of the requisite 2-aminoimidazole of Formula (2) with a compound of the formula M-(A')CO$_2$R wherein R, M, and A' are as defined above, in a suitable solvent such as N,N-dimethylformamide. Compounds of Formula (2) wherein R$^3$ is H are preferentially alkylated at a ring nitrogen atom. Therefore, in order to prepare compounds of Formula (I) wherein X is NH and R$^3$ is H, it is usually necessary to protect the ring nitrogen atom. The protecting group is preferably stable under basic conditions and easily removed under acidic conditions, e.g., a silyl or trityl group. The protected 2-aminoimidazole can then be used to prepare esters of Formula (3) wherein R$^3$ is a protecting group. The protecting group can be removed at any suitable stage in the synthetic sequence for the preparation of the compounds of Formula (I) wherein X is NH and R$^3$ is H.

Scheme 1

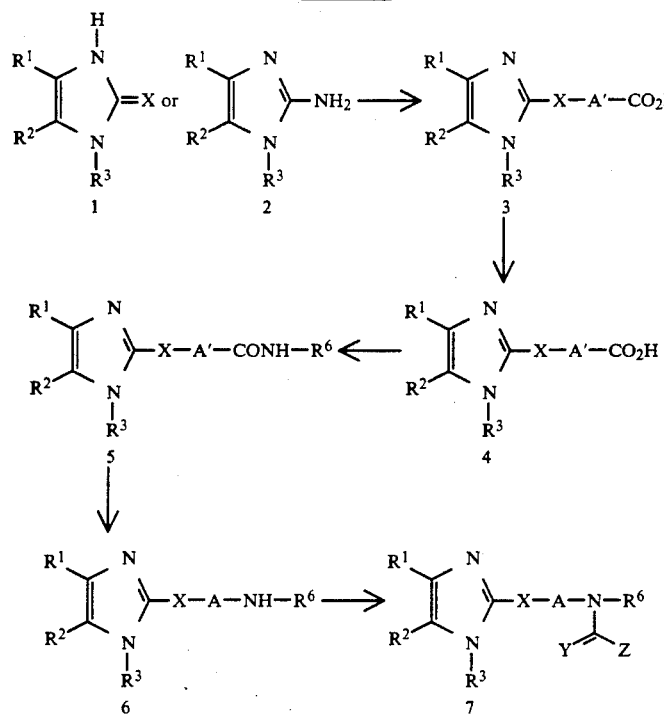

The esters of Formula (3) are hydrolyzed to the corresponding carboxylic acids of Formula (4) by methods which are well known in the chemical literature. For example, the hydrolysis can be accomplished by reaction with an alkali metal hydroxide in aqueous or organic solvents such as water, alcohols, ethers or mixtures thereof, followed by acidification with a mineral acid. The methods used to prepare compounds of Formula (4) are substantially similar to the methods described in U.S. Pat. No. 4,654,358, U.S. Pat. No. 4,460,598 and in co-assigned application U.S. Ser. No. 244,170 (BP-6339) filed Sep. 14, 1988 now U.S. Pat. No. 4,900,744, the teaching of which is incorporated by reference. Compounds of Formula (4) wherein $R^1$ and $R^2$ are phenyl or substituted phenyl, $R^3$ is H, X is S, A' is $(CH_2)_{n-1}$ and n is 8 to 21 are claimed as antihypercholesterolemic compounds in co-assigned application, U.S. Ser. No. 244,170 (BP-6339).

The amides of Formula (5) are prepared by coupling the carboxylic acids of Formula (4) with a primary amine by amide bond forming reactions which are well known in the chemical literature. One method for amide bond formation is to use a coupling reagent which generates a reactive intermediate such as a mixed anhydride or active ester. Examples of such coupling agents are disubstituted carbodiimides, N,N'-carbonyldiimidazole, diphenylphosphoryl azide, and the like. For example, the coupling can be carried out with a disubstituted carbodiimide such as dicyclohexylcarbodiimide in an appropriate solvent such as methylene chloride, acetonitrile, toluene, or N,N-dimethylformamide. Nucleophilic hydroxy compounds such as 1-hydroxy-1H-benzotriazole, which form highly active esters, may be added to catalyze the reaction.

There are several alternate approaches to the preparation of the amides of Formula (5). For example, the boron trifluoride etherate catalyzed reaction of the carboxylic acids of Formula (4) with a primary amine, with azeotropic removal of water, affords the amides of Formula (5). Another approach is to convert the carboxylic acids of Formula (4) to the corresponding acid chloride using thionyl chloride, oxalyl chloride or the like and then to react the acid chloride with a primary amine in the presence of a base such as triethylamine to afford the amides of Formula (5). Alternatively, the esters of Formula (3) can be directly converted to the amides of Formula (5) by ester aminolysis in the presence of strong alkali metal catalysts such as sodium amide, sodium hydride, sodium methoxide, Grignard reagents or butyllithium, or in the presence of milder catalysts such as 2-pyridone, boron tribromide, or dimethylaluminum amides.

The amines of Formula (6) can be prepared by reduction of the corresponding amides of Formula (5) by a variety of methods well known to those skilled in the art. For example, reagents such as lithium aluminum hydride, diborane, sodium bis(2-methoxyethoxy)aluminum hydride (Red-Al ®), and diisobutylaluminum hydride can be used to reduce an amide to an amine. Such reactions are typically conducted in an appropriate anhydrous aprotic solvent such as ether, toluene or tetrahydrofuran at a temperature from room temperature to the boiling point of the solvent for a period of 2-48 hours.

Alternatively amines of Formula (6), wherein X is NH can be prepared by the route shown in Scheme 2. The primary amines (9) can be prepared by reacting 2-bromoimidazoles of Formula (8) with an appropriately elaborated diamine under neat, thermal conditions or in an appropriate solvent such as N,N-dimethylformamide, toluene, acetonitrile or tetrahydrofuran, at or below the boiling point of the solvent.

Scheme 2

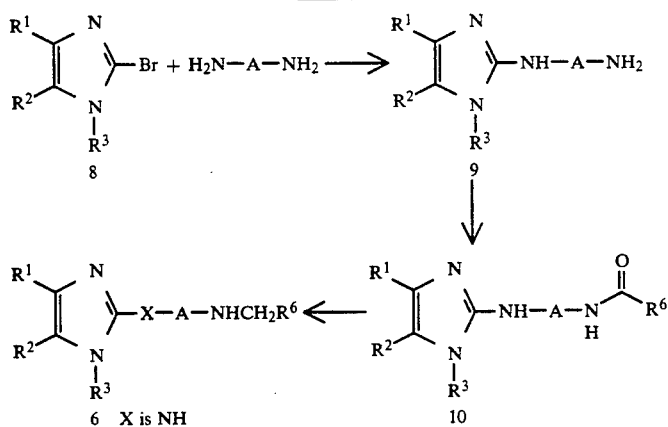

The secondary amines of Formula (6) wherein X is NH can be prepared by direct alkylation of the primary amines of Formula (9) with an appropriately substituted alkyl halide. Or, the secondary amines (6) are prepared by acylation of the primary amines of Formula (9) with an acid chloride or activated carboxylic acid derivative to give the amide of Formula (10) and reduction of the amide (10) to the amines (6) by well known methods previously described.

The compounds of Formula (7) where Y is O and Z is $NR^4$, $OR^4$, $R^4$ are prepared by the reaction of the secondary amines (6) with the requisite isocyanates, chloroformates, acid chlorides, activated urea or activated carboxylic acid derivatives in an appropriate solvent such as hexane, toluene, diethyl ether, diphenyl ether, methylene chloride or tetrahydrofuran at a temperature at or below the boiling point of the solvent.

The guanidines of Formula (7), where in Y is NH and Z is $NR^4$ are prepared by the reaction of the secondary amines (6) with an appropriately substituted S-methyl carbamimidothioate salt (C. R. Rasmussen, F. J. Villani, et al., *Synthesis*, 460, 1988), in acetonitrile or dioxane at reflux.

The amines of Formula (7), wherein Y is $H_2$ are prepared by reaction of the corresponding ureas or amides of Formula (7) wherein Y is O, with a reducing agent such as lithium aluminum hydride or other such reagents in an appropriate anhydrous aprotic solvent such as hexane, toluene, diethylether or tetrahydrofuran at temperatures at or below the boiling point of the solvent.

As shown in Scheme 3, the thioureas of Formula (12) wherein X is S, O or NH and Z is $NHR^4$ can be prepared in an analogous manner by the reaction of the secondary amines of Formula (6) with the requisite isothiocyanate. Alternatively, the thioureas or thioamides where Z is $R^4$ of Formula (12) can be prepared from the ureas or amides of Formula (7) by the reaction with Lawesson's reagent or diphosphorus pentasulfide in an appropriate solvent such as toluene.

Scheme 3

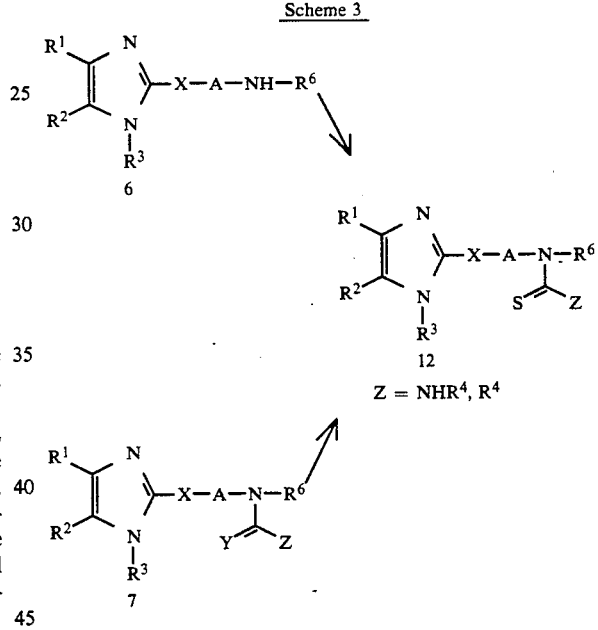

As shown in Scheme 4, alternatively the amides of Formula (5) can be prepared by the alkylation of (1) or (2) with compounds of the formula M-(A')CONHR$^6$ wherein M is a halogen or tosylate group, as described for compounds of Formula (3), Scheme 1.

Scheme 4

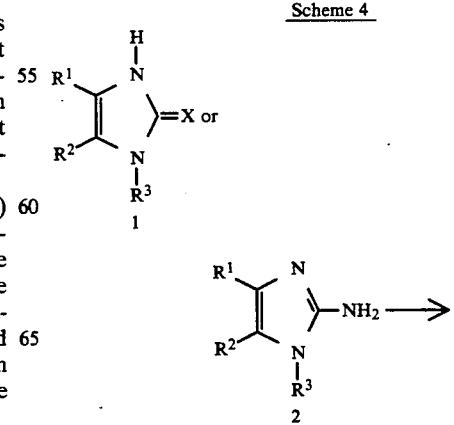

-continued
Scheme 4

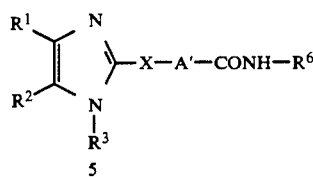

Alternatively, compounds of Formula (7), where X is O, S, or NH can be prepared by the route shown in Scheme 5. The compounds of Formula (13) can be prepared from a lactone or an hydroxyalkylcarboxylic ester and an appropriate amine, neat or in an inert solvent such as N,N-dimethylformamide at ambient or elevated temperatures. The amines of Formula (14) are prepared by reduction of the corresponding amide of Formula (13) by a variety of well known methods, as illustrated above. The compounds of Formula (15) are prepared by the reaction of the secondary amine (14) with the requisite isocyanates, chloroformates, acid chlorides, activated ureas or activated carboxylic acid derivatives as described for the preparation of compounds of Formula (7), Scheme 1.

The compounds of Formula (7), wherein A is branched alkyl, can be prepared by a route analogous to that shown in Scheme 5. The requisite lactones with branching substituents can be prepared by functionalization of the parent unsubstituted lactones. Alternatively, branched cyclic α,ω-diacid anhydrides can be reduced to the corresponding branched lactone using agents such as sodium borohydride. Synthesis of compounds of Formula (16) then proceeds exactly as described in the preceding paragraph, and alkylation of compounds of Formula (1) affords compounds of Formula (7), wherein A is branched alkyl.

The compound of Formula (16) can be prepared by conversion of the hydroxy group to a halogen moiety by a variety of well known methods. Examples of these methods are phosphorous tribromide, phosphorous oxychloride, thionyl chloride, or triphenylphosphine and carbon tetrabromide. Or, compounds of Formula (16) where M is a tosylate or similar functionality, can be prepared from toluene sulfonyl chloride and triethylamine, in an appropriate aprotic solvent such as methylene chloride, tetrahydrofuran or toluene.

The compounds of Formula (7) can be prepared by converting the requisite 4-imidazolin-2-one (1) where X is O, or 4-imidazolin-2-thione (1) where X is S into the corresponding alkali metal salt by addition of a base such as sodium hydride, and alkylating with the compounds of Formula (16) in a polar aprotic solvent such as N,N-dimethylformamide at an appropriate temperature.

-continued
Scheme 5

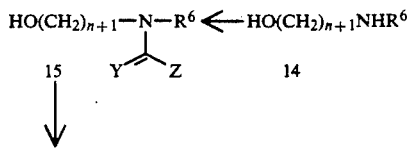

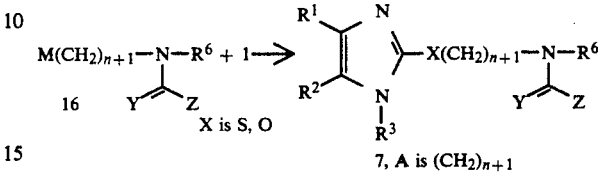

The compounds of Formula (7) wherein X is $CH_2$ are prepared by the route shown in Scheme 6. The compounds of Formula (18) are prepared by converting the requisite imidazoles of Formula (17) where $R^3$ is alkyl or an appropriate protecting group, into the corresponding alkali metal salt, by addition of a base such as n-butyl lithium, and alkylating with an appropriate alkyl halide in a solvent such as tetrahydrofuran under an inert atmosphere and reduced temperatures. The compounds of Formula (19) are prepared from compounds of Formula (18) by reaction with an appropriately substituted amine, in an inert solvent such as toluene, acetonitrile, tetrahydrofuran or N,N-dimethylformamide, at a temperature at or below the boiling point of the solvent. The imidazole compounds of Formula (20) are prepared by the reaction of the secondary amines of Formula (19) with the requisite isocyanate, chloroformate, acid chloride or other activated carboxylic acid derivative as previously described. Or, the imidazole compounds of Formula (20) can be prepared by reacting the alkali metal salt of compounds of Formula (17) with the elaborated compounds of Formula (16) in analogous conditions described above. The compounds of Formula (7) wherein X is $CH_2$ and $R^3$ is H, are prepared by deprotecting compounds of Formula (20), where $R^3$ is a protecting group. For example, when $R^3$ is a silyl protecting group, removal with tetrabutylammonium fluoride in tetrahydrofuran at reflux, affords compounds of Formula (7) where X is $CH_2$.

Likewise, compounds of Formula (7) wherein X is O, S, NH or $CH_2$ and Y is $H_2$ may be prepared by reacting compounds similar to compounds of Formula (18) with an appropriately functionalized secondary amine, $HNCH_2ZR^6$, in a solvent such as toluene, acetonitrile, tetrahydrofuran, or N,N-dimethylformamide at a temperature at or below the boiling point of the solvent.

Scheme 5

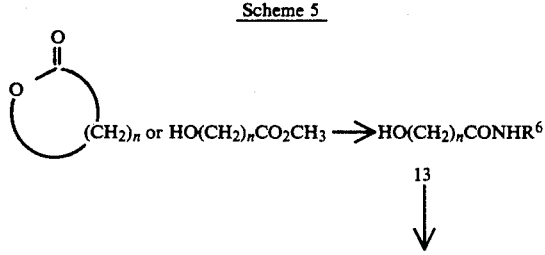

Scheme 6

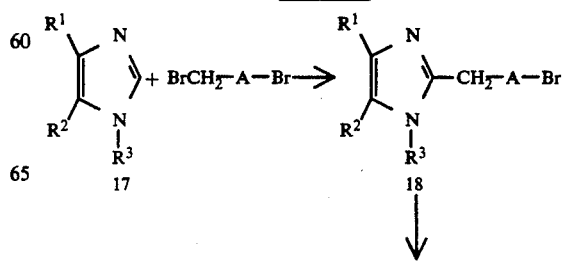

-continued
Scheme 6

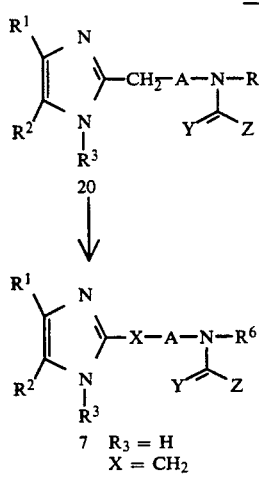

7  R₃ = H
   X = CH₂

The linked phenyl compounds of Formula (24) are prepared as shown in Scheme 7. The linked bis-benzaldehyde compounds of Formula (21) are prepared by bis alkylation of an appropriately functionalized dihaloalkyl, with a substituted salisaldehyde, using an alkali base, such as sodium hydride in an inert solvent, such as N,N-dimethylformamide. The α-hydroxyketones of Formula (22) are prepared by standard literature benzoin forming reaction conditions, Walter S. Ide, Johannes S. Buck, *Organic Reactions*, Vol. IV, p. 269, utilizing potassium cyanide in ethanol:water, at reflux.

The imidazoles of Formula (23) are prepared by methods well known in the literature, Klaus Hoffman, The Chemistry of Heterocyclic Compounds, Imidazoles, Part I, by condensing the α-hydroxyketone compounds of Formula (22) with thiourea, or ammonium thiocyanate, or an appropriately substituted thiourea in a suitable solvent such as N,N-dimethylformamide, ethanol or hexanol, at a temperature at or below the boiling point of the solvent.

The compounds of Formula (24) are prepared by alkylating the alkali metal salt of imidazole (23) with the compound of Formula (16), as described previously to give the compounds of Formula (24) directly or with a compound of formula M(A')CO₂R when R is CH₃ or C₂H₅, M is halogen or a tosylate group and A' is a moiety having one less methylene group than A, as described in Scheme 1.

Scheme 7

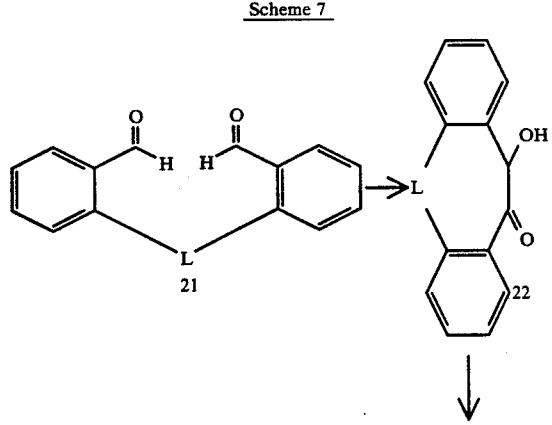

-continued
Scheme 7

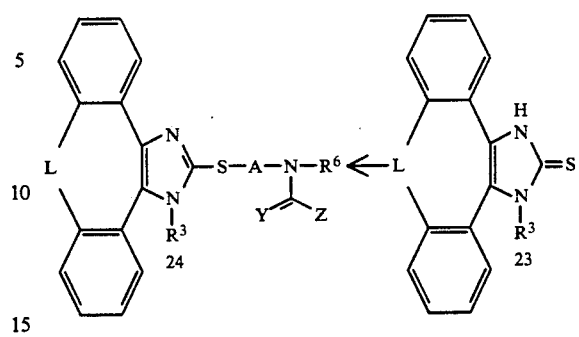

The compounds of Formula (1), Scheme 8, wherein X is S are available from commercial sources or can be prepared by methods as described above.

Scheme 8

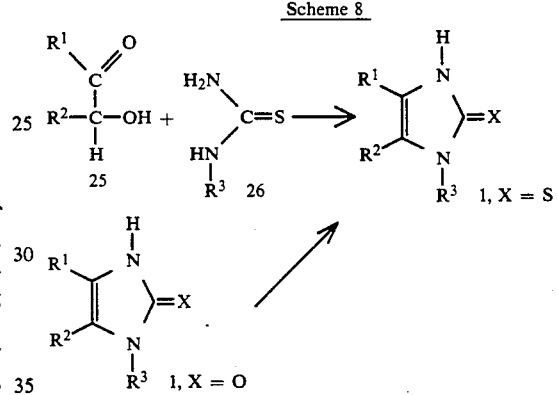

Alternatively, the compounds of Formula (1) where X is S, Scheme 8, can be prepared from the corresponding 4-imidazolin-2-ones of Formula (1) where X is O, *Org. Syn. Coll.*, Vol. II, 231, by reaction with Lawesson's reagent or diphosphorus pentasulfide in a suitable solvent such as toluene.

As shown in Scheme 9, the 2-aminoimidazoles of Formula (2) can be prepared by the reaction of the appropriately substituted α-aminoketones of Formula (27) with cyanamide (28). Compounds of Formula (2) can be used in the preparation of compounds of Formula (I) as previously described in Scheme 1.

Scheme 9

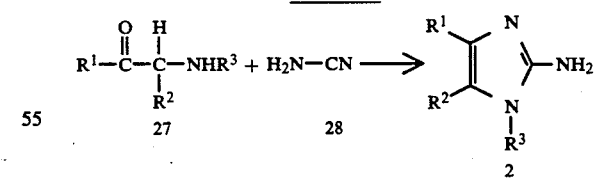

As shown in Scheme 10, the compounds of Formula (I) wherein X is S(O)ᵣ and r is 1 or 2 can be prepared by the oxidation of the compounds of Formula (29) by methods which are well known in the chemical literature. For example, the oxidation of (29) with one equivalent of a peracid such as m-chloroperoxybenzoic acid in a suitable solvent such as methylene chloride at a low temperature affords primarily the sulfoxides of Formula (30), and the oxidation of (29) with an oxidant such as potassium hydrogen persulfate, or Oxone ®, in a suitable solvent such as methanol affords the sulfones of Formula (31).

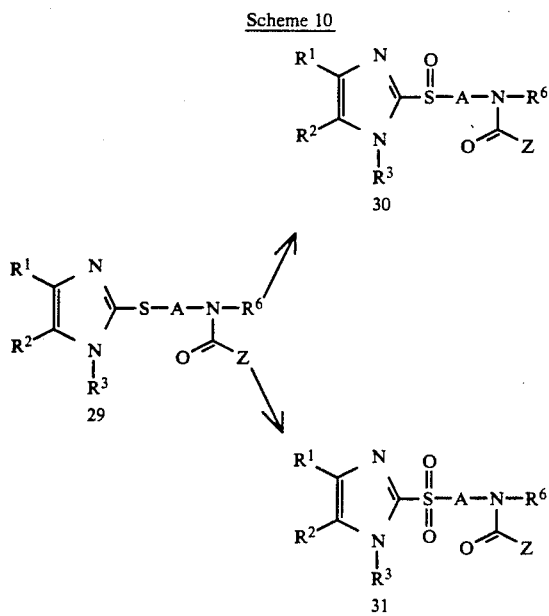

Scheme 10

Alternatively, compounds of Formula (7) where $R^3$ is not H, Scheme 11, can be prepared by direct alkylation of compounds of Formula (7) when R is H, in the presence or absence of a base such as potassium carbonate, pyridine, sodium hydride, triethylamine, or potassium t-butoxide in an appropriate solvent such as N,N-dimethylformamide, glyme, tetrahydrofuran, pyridine or methylene chloride.

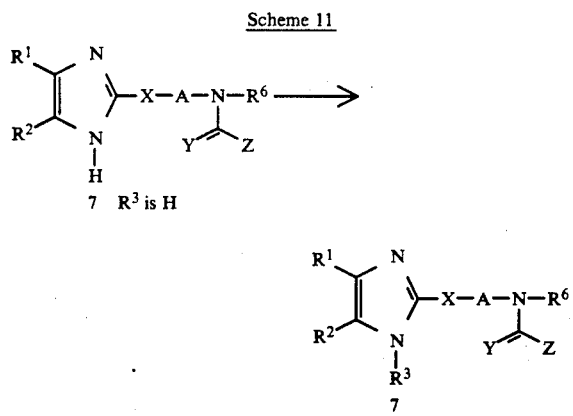

Scheme 11

Preparation of pharmaceutically suitable salts of Formula (I) can be carried out in accordance with well known techniques for forming salts. Physiologically acceptable salts include acid addition salts, e.g., hydrochloric, sulfuric, acetic, trifluoroacetic, succinic, citric, and benzene sulfonic acid salts.

The compounds of this invention and their preparation can be further understood by the following examples, which exemplify but do not constitute a limitation of the invention. In these examples, unless otherwise indicated, all temperatures are in degrees centigrade and parts and percentages are by weight.

EXAMPLE 1

Preparation of N'-(2,4-difluorophenyl)-N-[5-(4,5-dihenyl-1H-imidazol-2-ylthio)pentyl]-N-heptylurea Part A. To a solution of 4,5-diphenyl-2-imidazolethiol (25.2 g, 0.1 mol) in N,N-dimethylformamide (250 mL) was added, dropwise, a solution of ethyl 5-bromopentanoate (23.73 mL, 31.35 g, 0.15 mol) in N,N-dimethylformamide (80 mL), and the reaction mixture was stirred at reflux under nitrogen for 18 hours. The reaction mixture was cooled, poured into 5% sodium bicarbonate and ice, and then extracted with ethyl acetate. The combined organic extracts were washed sequentially with 5% sodium bicarbonate, water, saturated sodium chloride solution, dried over magnesium sulfate, and concentrated under vacuum. The residue was chromatographed with 7:3 hexane-ethyl acetate, and the resulting solid was recrystallized from acetonitrile and triturated with hexane to give 5-(4,5-diphenyl-1H-imidazol-2-ylthio)pentanoic acid ethyl ester (25.95 g, 0.068 mol) as a white solid, mp 87°–89°. $^1$H NMR (DMSO-d$_6$) $\delta$7.55–7.15(m,11H), 4.0(q,2H,J=8Hz), 2.9(t,2H,J=7Hz), 2.3(t,2H,J=7Hz), 1.9–1.6(m,4H), 1.2(t,3H,J=8Hz).

Additional esters which can be used as intermediates in the preparation of compounds of Formula (I) are prepared similarly as taught in co-assigned application, U.S. Ser. No. 244,170 (BP-6339).

Part B. To a solution of 5-(4,5-diphenyl-1H-imidazol-2-ylthio)pentanoic acid ethyl ester (7.6 g, 0.02 mol) in ethanol (200 mL), was added dropwise a solution of sodium hydroxide (7.6 g) in water (200 mL), and the reaction mixture was stirred at reflux under nitrogen for 3 hours. The reaction mixture was concentrated to half the original volume and then extracted with ether. The ether extracts were discarded. The reaction mixture was acidified to pH 1 with 1N hydrochloric acid and extracted with ether, and the combined organic extracts were dried over magnesium sulfate and concentrated under vacuum. The resulting solid was recrystallized from acetonitrile and triturated with hexane to give 5-(4,5-diphenyl-1H-imidazol-2-ylthio)pentanoic acid (3.88 g, 0.011 mol) as a white solid, mp 190°–195°. $^1$H NMR (DMSO-d$_6$) $\delta$12.6(s,1H), 7.6–7.1(m,10H), 3.3–3.1(m,2H), 2.3–2.1(m,3H), 1.8–1.6(m,4H).

Additional acids which can be used as intermediates in the preparation of compounds of Formula (I) are prepared similarly and are claimed in co-assigned application, U.S. Ser. No. 244,170.

Part C, Method 1. To a solution of 5-(4,5-diphenyl-1H-imidazol-2-ylthio)pentanoic acid (2.0 g, 0.0057 mol) in N,N-dimethylformamide (25 mL) was added 1-hydroxybenzotriazole hydrate (0.93 g, 0.0069 mol) followed by a solution of heptylamine (1.10 mL, 0.86 g, 0.0074 mol) in N,N-dimethylformamide (10 mL). The reaction mixture was cooled to 0° and dicyclohexylcarbodiimide (1.42 g, 0.0069 mol) was added portionwise as a solid. The reaction mixture was stirred for 2 hours at 0° and then stirred for 48 hours at ambient temperature. The solids were filtered and washed with N,N-dimethylformamide. The filtrate was concentrated and the residue was chromatographed with 1:1 hexane-ethyl acetate. The resulting solid was recrystallized from acetonitrile and triturated with hexane to give 5-(4,5-diphenyl-1H-imidazol-2-ylthio)-N-heptylpentanamide (2.21 g, 0.0049 mol) as a white solid, mp 104°–106°. $^1$H NMR (CDCl$_3$) δ11.6(s,1H), 7.6-7.1(m,10H), 6.1-6.0(m,1H), 3.1-2.8(m,4H), 2.2(t,2H,J=7Hz), 1.9-1.7(m,2H), 1.7-1.5(m,2H), 1.4-1.1(m,10H), 0.9(t,3H,J=8Hz).

Part C, Method 2. To a solution of 5-(4,5-diphenyl-1H-imidazol-2-ylthio)pentanoic acid (2.0 g, 0.0057 mol) in toluene (35 mL) was added heptylamine (1.63 mL, 1.27 g, 0.011 mol) and then boron trifluoride etherate (1.35 mL, 1.56 g, 0.011 mol) and the reaction mixture was stirred at reflux for 120 hours using a Dean-Stark moisture trap. The reaction mixture was cooled, extracted with 0.1N NaOH, 0.1N HCl, and water, and the combined organic extracts were dried over magnesium sulfate and concentrated under vacuum. The residue was chromatographed and worked-up as described in Part C, Method 1, to give 5-(4,5-diphenyl-1H-imidazol-2-ylthio)-N-heptylpentanamide (2.35 g, 0.005 mol) as a white solid.

Part D. To a solution of lithium aluminum hydride, (1.52 g, 0.04 mol) in dry tetrahydrofuran (50 mL) was added, dropwise, a solution of 5-(4,5-diphenyl-1H-imidazol-2-ylthio)-N-heptylpentanamide (4.04 g, 0.009 mol) in tetrahydrofuran (25 mL) and the reaction mixture was stirred at reflux for 18 hours. The reaction mixture was cooled to 0°, quenched by the slow and careful sequential addition of water (1.52 mL), 15% sodium hydroxide (4.56 mL), and water (4.56 mL), and then stirred at 0° for 30 minutes. The solution was then dried over magnesium sulfate and concentrated under vacuum, and the residue was chromatographed with a gradient of 1:0 to 3:1 to 1:1 ethyl acetate-methanol. The resulting yellow oil was triturated with cold hexane to give N-[5-(4,5-diphenyl-1H-imidazol-2-ylthio)pentyl]-1-heptanamine as a white solid. A solution of this amine (0.80 g, 0.0018 mol) in ether (20 mL) was treated with a sufficient amount of ethereal HCl (about 25 mL) to cause complete precipitation of the amine as the hydrochloride salt. The reaction mixture was stirred for 15 minutes, and the supernatant liquid was decanted to afford a gummy solid, which was triturated with hot acetonitrile and then with cold hexane to give N-[5-(4,5-diphenyl-1H-imidazol-2-ylthio)pentyl]-1-heptanamine hydrochloride (0.82 g, 0.0017 mol) as a white solid, mp 187°-190°. $^1$H NMR (CDCl$_3$) δ9.3(s,2H), 7.7-7.3(m,10H), 3.7-3.5(m,2H), 3.0-2.7(m,4H), 2.0-1.2(m,16H), 0.9(1,3H,J=8Hz).

Part E. To a solution of N-[5-(4,5-diphenyl-1H-imidazol-2-ylthio)pentyl]-1-heptanamine (1.0 g, 0.0024 mol) in hexane (50 mL) was added, dropwise, a solution of 2,4-difluorophenylisocyanate (0.296 mL, 0.388 g, 0.0025 mol) in hexane (25 mL), and the reaction mixture was stirred at ambient temperature for 3 hours. The reaction mixture was concentrated under vacuum and the residue was chromatographed with 7:3 hexane-ethyl acetate to give the title compound (0.86 g, 0.0015 mol) as a white solid, mp 96°-98°. $^1$H NMR (CDCl$_3$) δ10.8(s,1H), 7.7-7.1(m,14H), 3.4(t,2H,J=7Hz), 3.2(t,2H,J=7Hz), 3.0(t,2H,J=7Hz), 1.9-1.4(m,16H), 0.9(t,3H,J=8Hz).

EXAMPLE 2

Preparation of N-[5-(4,5-diphenyl-1H-imidazol-2-ylthio)pentyl]-N-heptyl-N'-phenylurea To a solution of N-[5-(4,5-diphenyl-1H-imidazol-2-ylthio)pentyl]-1-heptanamine (1.0 g, 0.0024 mol) in hexane (50 mL) was added, dropwise, a solution of phenylisocyanate (0.27 mL, 0.298 g, 0.0025 mol) in hexane (25 mL) and the reaction mixture was stirred at ambient temperature for 4 hours. The reaction mixture was concentrated under vacuum and the residue was chromatographed with 6:4 hexane-ethyl acetate to give the title compound (0.5 g, 0.009 mol) as a yellow amorphous solid. $^1$H NMR (CDCl$_3$) δ11.0(s,1H), 7.7-6.9(m,14H), 6.4(s,1H), 3.4(t,2H,J=7Hz), 3.2(t,2H,J=7Hz), 3.0(t,2H,J=7Hz), 1.9-1.1(m,16H), 0.9(t,3H,J=8Hz).

EXAMPLE 3

Preparation of N'-(2,4-difluorophenyl)-N-[8-(4,5-diphenyl-1H-imidazol-2-ylthio)octyl]-N-heptylurea Part A. To a solution of 8-(4,5-diphenyl-1H-imidazol-2-ylthio)octanoic acid (8.44 g, 0.02 mol) in methylene chloride (100 mL) at 0° was added, portionwise as a solid, dicyclohexylcarbodiimide (4.12 g, 0.02 mol), and the reaction mixture was stirred at 0° for 30 minutes. To this reaction mixture was added, dropwise, heptylamine (2.96 mL, 2.3 g, 0.02 mol) and the reaction mixture was stirred at reflux for 72 hours. The reaction mixture was cooled, and the solids were filtered and washed with chloroform. The filtrate was concentrated under vacuum and the residue was chromatographed with a gradient of 7:3 to 1:1 hexane-ethyl acetate. The resulting solid was recrystallized from acetonitrile and triturated with hexane to give 8-(4,5-diphenyl-1H-imidazol-2-ylthio)-N-heptyloctanamide (3.28 g, 0.0067 mol) as a white solid, mp 119°-120°. $^1$H NMR (DMSO-d$_6$) δ12.5(s,1H), 7.8-7.1(m,10H), 3.2-2.9(m,4H), 2.0(t,2H,J=7Hz), 1.75-1.0(m,21H), 1.0-0.8(m,3H).

Part B. To a solution of lithium aluminum hydride (0.96 g, 0.025 mol) in dry tetrahydrofuran (30 mL) was added, dropwise, a solution of 8-(4,5-diphenyl-1H-imidazole-2-ylthio)-N-heptyloctanamide (2.82 g, 0.0057 mol) in tetrahydrofuran (15 mL) and the reaction mixture was stirred at reflux for 18 hours. The reaction mixture was cooled to 0°, quenched by the slow and careful sequential addition of water (0.96 mL), 15% sodium hydroxide (2.88 mL), and water (2.88 mL), and then stirred at 0° for 30 minutes. The solution was then dried over magnesium sulfate and concentrated, and the residue was chromatographed with 1:1 hexane:ethyl acetate and then with a gradient of 1:0 to 3:1 to 1:1 ethyl acetate-methanol to give 8-(4,5-diphenyl-1H-imidazol-2-ylthio)-N-heptyl-1-octanamine (1.07 g, 0.0022 mol) as a white solid, mp 87°-89°. $^1$H NMR (CDCl$_3$) δ7.6-7.2(m,11H), 3.1(t,2H,J=7Hz), 2.7-2.5(m,2H), 1.8-1.1(m,25H), 0.9(t,3H,J=8Hz).

Part C. To a solution of 8-(4,5-diphenyl-1H-imidazol-2-ylthio)-N-heptyl-1-octanamine (0.5 g, 0.001 mol) in hexane (25 mL) was added, dropwise, a solution of 2,4-difluorophenylisocyanate (0.15 mL, 0.194 g, 0.00125 mol) in hexane (10 mL), and the reaction mixture was stirred at ambient temperature for 3 hours. The reaction mixture was concentrated under vacuum and the residue was chromatographed using 8:2 hexane-ethyl acetate to give a solid which was triturated with cold ethyl acetate and then hexane to give the title compound (0.18 g, 0.00028 mol) as a white solid, mp 89°-91°. $^1$H NMR (DMSO-d$_6$) δ12.5(s,1H), 7.9(s,1H), 7.5-7.1(m,10H), 3.3-3.1(m,5H), 1.8-1.2(m,17H), 0.9(t,3H,J=8Hz).

EXAMPLE 4

Preparation of N-butyl-N'-(2,4-difluorophenyl)-N-[8-(4,5-diphenyl-1H-imidazol-2-ylthio)octyl]urea Part A. To a solution of 8-(4,5-diphenyl 1H-imidazol-2-ylthio)octanoic acid (4.4 g, 0.0125 mol) in methylene chloride (65 mL) at 0° was added, portionwise as a solid, dicyclohexylcarbodiimide (2.3 g, 0.011 mol) and the reaction mixture was stirred at 0° for 30 minutes. To this reaction mixture was added, dropwise, a solution of butylamine (1.24 mL, 0.92 g, 0.012 mol) in methylene chloride (15 mL) and the reaction mixture was stirred at reflux for 18 hours. The reaction mixture was cooled, and solids were filtered and washed with methylene chloride. The filtrate was concentrated under vacuum and the residue was chromatographed with a gradient of 7:3 to 1:1 hexane-ethyl acetate. The resulting solid was recrystallized from acetonitrile and triturated with hexane to give N-butyl-8-(4,5-diphenyl-1H-imidazol-2-ylthio)octanamide (1.43 g, 0.003 mol) as a white solid, mp 136°-137°. $^1$H NMR (DMSO-d$_6$) $\delta$12.5(s,1H), 7.8-7.7(m,1H), 7.7-7.1(m,10H), 3.2-2.9(m,4H), 2.0(t,2H,J=7Hz), 1.8-1.1(m,14H), 0.9(t,3H,J=8Hz).

Part B. To a solution of lithium aluminum hydride (0.46 g, 0.012 mol) in dry tetrahydrofuran (15 mL) was added, dropwise, a solution of N-butyl-8-(4,5-diphenyl-1H-imidazol-2-ylthio)octanamide (1.20 g, 0.0027 mol) in tetrahydrofuran (8 mL) and the reaction mixture was stirred at reflux for 18 hours. The reaction mixture was cooled to 0° C. and quenched by the slow and careful sequential addition of water (0.46 mL), 15% sodium hydroxide (1.38 mL), and water (1.38 mL) and then the reaction mixture was stirred at 0° for 30 minutes. The solution was dried over magnesium sulfate and concentrated under vacuum, and the residue was chromatographed with 1:1 hexane-ethyl acetate and then with a gradient of 1:0 to 8:2 to 1:1 ethyl acetate-methanol. The resulting solid was triturated with hexane to give N-butyl-8-(4,5-diphenyl-1H-imidazol-2-ylthio)octanamine (0.45 g, 0.001 mol) as a white solid, mp 75°-78°. $^1$H NMR (CDCl$_3$) $\delta$7.6-7.1(m,10H), 3.1(t,2H,J=7Hz), 2.5(t,2H,J=7Hz), 1.7-1.0(m,16H), 0.9(t,3H,J=8Hz).

Part C. To a solution of N-butyl-8-(4,5-diphenyl-1H-imidazol-2-ylthio)octanamine (0.2 g, 0.00045 mol) in hexane (15 mL) was added, dropwise, a solution of 2,4-difluorophenylisocyanate (0.065 mL, 0.085 g, 0.00055 mol) in hexane (5 mL) and the reaction mixture was stirred at ambient temperature for 3 hours. The reaction mixture was concentrated under vacuum and the residue was chromatographed with 7:3 hexane-ethyl acetate and the resulting solid was recrystallized from acetonitrile and triturated with hexane to give the title compound (0.138 g, 0.00023 mol) as a white solid, mp 114°-115°. $^1$H NMR (CDCl$_3$) $\delta$8.1-7.9(m,1H), 7.6-7.2(m,11H), 6.95-6.75(m,2H), 6.5-6.4(m,1H), 3.4-3.1(m,6H), 1.8-1.3(m,16H), 1.0(t,3H,J=8Hz).

EXAMPLE 5

Preparation of N'-(2,4-dimethoxyphenyl)-N-[5-(4,5-diphenyl-1H-imidazol-2-ylthio)pentyl]-N-heptylurea To a solution of N-[5-(4,5-diphenyl-1H-imidazol-2-ylthio)pentyl]-1-heptanamine (0.75 g, 0.0017 mol), prepared according to the procedure of Example 1, Part D, in hexane (40 mL) was added, dropwise, a solution of 2,4-dimethoxyphenylisocyanate (0.358 g, 0.002 mol) in hexane (20 mL) and the reaction mixture was stirred at ambient temperature for 4.5 hours. The reaction mixture was concentrated under vacuum and the residue was chromatographed with 7:3 hexane-ethyl acetate. The resulting solid was triturated with hexane to give the title compound (0.83 g, 0.0014 mol) as a glassy solid. $^1$H NMR (CDCl$_3$) $\delta$7.7-7.1(m,10H), 6.8-6.1(m,3H), 3.8(s,3H), 3.7(s,3H), 3.45(s,1H), 3.4-3.3(m,2H), 3.2(t,2H,J=7Hz), 3.0(t,2H,J=7Hz), 1.8-1.1(m,16H), 0.9(t,3H,J=8Hz).

EXAMPLE 6

Preparation of N'-(2,4-difluorophenyl)-N-heptyl-N-[5-(1-methyl-4,5-diphenyl-1H-imidazol-2-ylthio)pentyl]urea To a solution of potassium carbonate (0.056 g, 0.00042 mol) in dry tetrahydrofuran (10 mL) was added, portionwise as a solid, N'-(2,4-difluorophenyl)-N-[5-(4,5-diphenyl-1H-imidazol-2-ylthio)pentyl]-N-heptylurea (0.25 g, 0.00042 mol) and the reaction mixture was stirred at ambient temperature for 10 minutes. To this reaction mixture was added, dropwise, methyl iodide (0.039 mL, 0.0895 g, 0.00063 mol) and the reaction mixture was stirred for 18 hours at ambient temperature. The reaction mixture was then treated with N,N-dimethylformamide (1.0 mL) and methyl iodide (0.1 mL) and the reaction mixture was stirred at reflux for an additional 24 hours. The reaction mixture was cooled, poured into water and extracted with ethyl acetate. The combined organic extracts were dried over magnesium sulfate and concentrated under vacuum. The residue was chromatographed with 3:7 hexane-ethyl acetate to give the title compound (0.13 g, 0.00022 mol) as a yellow oil. $^1$H NMR (CDCl$_3$) $\delta$8.1-8.0(m,1H), 7.5-7.1(m,10H), 6.9-6.7(m,2H), 6.4(s,1H), 3.5(s,3H), 3.4-3.2(m,5H), 1.9-1.2(m,17H), 0.9(t,3H,J=8Hz).

EXAMPLE 7

Preparation of N-[5-(4,5-diphenyl-1H-imidazol-2-ylthio)pentyl]-N-heptyl-N'-methylurea To a solution of N-[5-(4,5-diphenyl-1H-imidazol-2-ylthio)pentyl]-1-heptanamine (0.30 g, 0.0007 mol) in hexane (15 mL) was added methylisocyanate (0.06 mL, 0.057 g, 0.001 mol) and the reaction mixture was stirred at ambient temperature for 18 hours. The reaction mixture was concentrated under vacuum and the residue was chromatographed with 1:1 hexane-ethyl acetate. The resulting oil was triturated with hexane to give the title compound (0.23 g, 0.00047 mol) as a white solid, mp 93°-96°. $^1$H NMR (CDCl$_3$) $\delta$7.6-7.2(m,11H), 4.35-2.7(m,9H), 1.9-1.2(m,16H), 0.9(t,3H,J=8Hz).

EXAMPLE 8

Preparation of N-[5-(4,5-diphenyl-1H-imidazol-2-ylthio)pentyl]-N-heptyl-N'-propylurea To a solution of N-[5-(4,5-diphenyl-1H-imidazol-2-ylthio)pentyl]-1-heptanamine (0.36 g, 0.0008 mol) in hexane (15 mL) was added propylisocyanate (0.094 mL, 0.085 g, 0.001 mol), and the reaction mixture was stirred at ambient temperature for 4 hours. The reaction mixture was then treated with additional propylisocyanate (0.094 mL, 0.085 g, 0.001 mol) and stirred at ambient temperature overnight and then at reflux for 72 hours. The reaction mixture was concentrated under vacuum and the residue was chromatographed using 2:8 hexane-ethyl acetate. The resulting oil was triturated with hexane to give the title compound (0.8 g, 0.00015 mol) as a white solid, mp 78°–80°. ¹H NMR (CDCl₃) 7.6–7.2(m,10H), 4.4(t,1H,J=7Hz), 3.4–2.9(m,8H), 1.9–1.1(m,19H), 1.0–0.75(m,6H).

EXAMPLE 9

Preparation of N'-(2.4-difluorophenyl)-N[-2-(4,5-diphenyl-1H-imidazol-2-ylthio)ethyl]-N-propylurea Part A. To a solution of bromoacetylchloride (25.51 mL, 48.67 g, 0.31 mol) in methylene chloride (200 mL) at −15° was added, dropwise, a solution of propylamine (24.62 mL, 17.7 g, 0.3 mol) in methylene chloride (100 mL) and the reaction mixture was stirred at 0° for 30 minutes and then stirred at ambient temperature for 30 minutes. The reaction mixture was poured into water and then extracted with methylene chloride. The combined organic extracts were dried over magnesium sulfate and concentrated under vacuum. The residue was distilled to give bromo-N-propylacetamide as a clear liquid, bp 138°–142°. ¹H NMR (CDCl₃) δ7.1(s,1H), 3.9(d,2H,J=6Hz), 3.3(m,2H), 1.6(m,2H), 0.9(t,3H,J=7Hz).

Part B. A portion of sodium hydride, 60% in mineral oil (0.4 g, 0.01 mol), was washed twice with hexane (10 mL) and the hexane was replaced with N,N-dimethylformamide (100 mL). To this solution was added, portionwise as a solid, sodium iodide (0.4 g, 0.003 mol) and then, dropwise, a solution of diphenylimidazole (2.52 g, 0.01 mol) in N,N-dimethylformamide (10 mL) followed by the dropwise addition of a solution of bromo-N-propylacetamide (1.80 g, 0.01 mol) in N,N-dimethylformamide (10 mL). The reaction mixture was stirred at reflux for 18 hours, then cooled and poured, carefully, into ice water, and then extracted with ethyl acetate. The combined organic extracts were backwashed with brine, dried over magnesium sulfate and concentrated under vacuum. The residue was chromatographed using 1:1 hexane-ethyl acetate and the resulting solid was recrystallized from acetonitrile to give 2-(4,5-diphenyl-1H-imidazol-2-ylthio)-N-propylacetamide as a white solid, mp 183°–185°. ¹H NMR (DMSO-d₆) δ12.6(s,1H), 8.3(s,1H), 7.5–7.1(m,10H), 3.8(s,2H), 3.0(q,2H,J=7.5Hz), 1.4(sextet, 2H,J=9Hz), 0.8(t,3H,J=6Hz).

Part C. Employing the method of Example 1, Part D, but using 2-(4,5-diphenyl-1H-imidazol-2-ylthio)-N-propylacetamide, N-[2-(4,5-diphenyl-1H-imidazol-2-ylthio)ethyl]-1-propanamine (0.28 g, 0.00083 mol) was obtained as an oil. ¹H NMR (CDCl₃) δ7.9–7.6(m,2H), 7.5–7.1(m,10H), 3.1(s,4H), 2.6(t,2H,J=6Hz), 1.4(sextet, 2H,J=12Hz), 0.8(t,3H,J=9Hz).

Part D. Employing the method of Example 1, Part E, but using N-[2-(4,5-diphenyl-1H-imidazol-2-ylthio)ethyl]-1-propanamine, the title compound (0.20 g, 0.00045 mol) was obtained as a white solid, mp 189°–190°. ¹H NMR (CDCl₃) δ11.6–11.2(s,1H), 7.8–7.6(s,1H), 7.6–6.9(m,10H), 6.8–6.6(m,2H), 3.8(t,2H,J=7Hz), 3.4(t,2H,J=6.5Hz), 3.2(t,2H,J=6Hz), 1.8–1.6(m,4H), 1.0(t,3H,J=7.5Hz).

EXAMPLE 90

Preparation of N-5-(4,5-diphenyl-1H-imidazol-2-ylthio]-N-heptyl-N'-(2-pyridinyl)-urea A mixture of N-[5-(4,5-diphenyl-1H-imidazol-2-ylthio)pentyl]-1-heptanamine (4.35 g; 0.01 mol) and pyridyltosylurea (3.2 g; 0.011 mol; Frigola Conatansa, Jordi; ES 534,782) in diphenyl ether (35 mLs) was stirred under nitrogen at 180° C. for 30 minutes. The cooled solution was chromatographed with 1:1 hexane:ethyl acetate to give the title compound (4.03 g; 0.0073 mol) as an orange oil. ¹H NMR (CDCl₃) δ8.15–8.05(m,1H), 7.9(d,1H,J=8.4Hz), 7.6–7.4(m,5H), 7.3–7.1(m,8H), 6.9–6.8(m,1H), 3.32(t,2H,J=7.2Hz), 3.25(t,2H,J=7.9Hz), 3.05(t,2H,J=6.6Hz), 1.8–1.45(m,8H), 1.4–1.2(m,8H), 0.9(t,3H,J=6.8Hz).

EXAMPLE 118

Preparation of N-[5-[4,5-bis(4-methoxyphenyl)-1H-imidazol-2-ylthio]-pentyl]-N'-(2,4-difluorophenyl)-N-heptylurea Part A. A solution of γ-valerolactone (25.0 g, 0.249 mol) in toluene (50 mL) and n-heptylamine (35.96 g, 0.312 mol) was heated to reflux for 18 hours under a nitrogen atmosphere. The reaction mixture was allowed to cool to ambient temperature, diluted with ethyl acetate (300 mL), washed with 1N aqueous HCl (50 mL), water, brine, dried over magnesium sulfate and concentrated to give a white solid. The product was crystallized from ethyl ether:hexane to give N-heptyl-5-hydroxypentanamide (41.8 g, 0.194 mol) as white plates, mp 55°–6°. ¹H NMR (CDCl₃) δ6.06(bs,1H), 3.61(t,2H), 3.24(q,2H), 3.19(bs,1H), 2.19(t,2H), 1.80–1.23(m,14H), 0.866(t,3H).

Part B. To a solution of lithium aluminum hydride (6.7 g, 0.176 mol) in dry tetrahydrofuran (300 mL), a solution of N-heptyl-5-hydroxypentanamide (19.0 g, 0.088 mol) in dry tetrahydrofuran (100 mL) under a nitrogen atmosphere was added dropwise. The reaction mixture was heated to reflux for 18 hours, allowed to cool to room temperature and was poured slowly into a stirred mixture of 10% aqueous sodium sulfate (400 mL) and ice (200 mL). The resulting slurry was filtered through a bed of Celite ® and the filtrate was extracted with ethyl acetate (2×500 mL). The combined organic layer was washed with water, brine, dried over magnesium sulfate and concentrated to give a viscous yellow oil. The product was crystallized from hexane to give N-(5-hydroxypentyl)-N-heptylamine (15.2 g, 0.075 mol) as a white powder, mp 47°–8°. ¹H NMR (CDCl₃) δ3.63(t,2H), 2.63(q,4H), 2.39(bs,2H), 1.66–1.24(m,16H), 0.905(t,3H).

Part C. To a solution of N-(5-hydroxypentyl)-N-heptylamine (11.65 g, 0.0578 mol) in methylene chloride (75 mL) under a nitrogen atmosphere cooled to 0°, 2,4-difluorophenylisocyanate (8.97 g, 0.0578 mol) was added slowly. The reaction mixture was stirred for 1 hour, poured into 1N aqueous HCl (200 mL) and was extracted with ethyl acetate (300 mL). The combined organic layer was washed with water, brine, dried over magnesium sulfate and was concentrated to give N'-(2,4-difluorophenyl)-N-heptyl-N-5-hydroxypentylurea as a pale yellow oil (20.0 g, 0.056 mol). ¹H NMR (CDCl₃) δ8.03(m,1H), 6.88–6.59(m,2H), 6.45(bs,1H), 3.68(t,2H), 3.33(m,4H), 1.81–1.22(m,16H), 0.907(t,3H).

Part D. To a solution of N'-(2,4-difluorophenyl)-N-heptyl-N-5-hydroxypentylurea (15.0 g, 0.042 mol) and carbon tetrabromide (16.75 g, 0.051 mol) in methylene chloride (350 mL) under a nitrogen atmosphere at ambient temperature, a solution of triphenylphosphine (13.24 g, 0.051 mol) in methylene chloride (100 mL) was added slowly. The reaction mixture was stirred for 3 hours and was concentrated in vacuo to give crude viscous oil. The product was purified by flash chromatography on silica gel (400 mL) eluting with hexane:ethyl acetate (90:10 v:v) to give N-(5-bromopentyl)-N'-(2,4-difluorophenyl)-N-heptylurea as a viscous colorless oil (17.5 g, 0.042 mol). $^1$H NMR (CDCl$_3$) δ8.14–8.00(m,1H), 6.92–6.79(m,2H), 6.35(bs,1H), 3.49–3.25(m,6H), 1.99–1.26(m,16H), 0.915(t,3H).

Part E. To a suspension of sodium hydride (0.88 g, 60% mineral oil dispersion, 0.0022 mol) (washed free of mineral oil with hexane) in N,N-dimethylformamide (15 mL) under a nitrogen atmosphere, cooled to 0°, a solution of 4,5-[bis-(4-methoxyphenyl)-1H-imidazol]-2-thione (0.63 g, 0.002 mol) in N,N-dimethylformamide (5 mL) was added slowly. The reaction mixture was stirred for 2 hours and then a solution of N-(5-bromopentyl)-N'-(2,4-difluorophenyl)-N-heptylurea (0.845 g, 0.002 mol) in N,N-dimethylformamide (3 mL) was added. The reaction mixture was allowed to warm to ambient temperature, stirred an additional 2 hours, poured into water (50 mL) and extracted with ethyl acetate (2×50 mL). The combined organic extracts were washed with water, brine, dried over magnesium sulfate and concentrated to give a viscous oil. The product was purified by flash chromatography on silica gel (100 mL) eluting with hexane:ethyl acetate (70:30 v:v) to give the title compound as a pure yellow foam (0.98 g, 0.0015 mol). $^1$H NMR (CDCl$_3$) δ10.15(bs,1H), 7.87–7.76(m,1H), 7.51(d,2H), 7.3(d,2H), 6.86–6.6(m,6H), 6.42(d,1H), 3.8(s, 6H), 3.4(t,2H), 3.26(t,2H), 2.99(t,2H), 1.84–1.25(m,16H), 0.89(t,3H).

EXAMPLE 207

Preparation of
N-[5-(4,5-diphenyl-1H-imidazol-2-ylthio)pentyl]-N'-octyl-N-phenylurea To a solution of N-[5-(4,5-diphenyl-1H-imidazol-2-ylthio)pentyl]benzeneamine (0.41 g, 0.001 mol) in toluene (25 mL) was added n-octylisocyanate (0.23 g, 0.0015 mol). The reaction mixture was stirred at reflux for 18 hours and then the solvent was removed under vacuum. The residue (1.0 g) was chromatographed with 7:3 hexane-ethyl acetate. The resulting solid was triturated with hexane to give the title compound (0.32 g, 0.00056 mol) as a white solid, mp 74°–76°. $^1$H NMR (CDCl$_3$) 11.8(s,1H), 7.75–7.1(m,15H), 4.3(t,1H,J=6.0Hz), 3.8(t,2H,J=7.0Hz), 3.0(quintet,4H,J=6.0Hz), 1.9–0.90(m,18H), 0.8(t,3H,J=7.0Hz).

EXAMPLE 209

Preparation of
N-[5-[4,5-bis(4-hydroxyphenyl)-1H-imidazol-2-ylthio]-pentyl]-N'-(2,4-difluorophenyl)-N-heptylurea To a stirred solution of N-[5-[4,5-bis(4-methoxyphenyl)-1H-imidazol-2-ylthio]pentyl]-N'-(2,4-difluorophenyl)-N-heptylurea (0.78 g, 0.0012 mol) in methylene chloride (30 mL) cooled to −78° under a nitrogen atmosphere, 1M boron tribromide in methylene chloride (3.6 mL) was added. The reaction mixture stirred for 1 hour at 0°, was poured over ice (100 mL) and extracted with ethyl acetate (2×50 mL). The combined organic layer was washed with 10% aqueous NaHCO$_3$ (50 mL), water, brine, dried over magnesium sulfate, and concentrated in vacuo to give the crude oil. The product was purified by flash chromatography on silica gel (100 mL) eluting with hexane:ethyl acetate (40:60 v:v) to give a white foam, mp 110°–12° (0.5 g, 0.00008 mol). $^1$H NMR (DMSO-d$_6$) δ12.22 (bs,1H), 9.55(bs,1H), 9.32(bs,1H),7.92(s,1H), 7.45–6.6(m,11H), 3.24(m,4H), 3.06(t,2H), 1.77–1.17(m,16H), 0.88(t,3H).

EXAMPLE 211

Preparation of
N-[5-(1H,9H-dibenz-[4,5:8,9][1,3]dioxonino-[6,7-d]imidazol-2-ylthio)pentyl]-N'-(2,4-difluorophenyl)-N-heptylurea Part A. To a suspension of sodium hydride (washed free of mineral oil with hexane) (2.45 g, 80% oil dispersion, 0.081 mol) in dry N,N-dimethylformamide (50 mL) under a nitrogen atmosphere, cooled to 0°, a solution of salisaldehyde (10.0 g, 81.9 mmol) in dry N,N-dimethylformamide (10 mL) was added slowly. The reaction mixture was stirred at 0° for 2 hours and diiodomethane (11.3 g, 0.041 mol) was added. The reaction mixture was allowed to warm to ambient temperature for 18 hours and then was warmed to 60° for 20 hours. The reaction was allowed to cool to ambient temperature, poured into 1N aqueous HCl (100 mL) and extracted with ethyl acetate (2×100 mL). The combined organic extract was washed with water, brine, dried over magnesium sulfate and concentrated to give a solid. The product was purified by flash chromatography on silica gel (300 mL) eluting with methylene chloride (100%) to give 2,2'-(methylenedioxy)-bis-(2-benzaldehyde) as a white crystalline solid, mp 131° to 3° (5.1 g, 0.0199 mol). $^1$H NMR (CDCl$_3$) δ10.47(s, 2H), 7.87(d,2H), 7.68–7.54(m,2H), 7.21(d,2H), 7.15(t,2H), 6.02(s, 2H).

Part B. A mixture of 2,2'-(methylenedioxy)-bis-(2-benzaldehyde) (5.0 g, 0.0195 mol), potassium cyanide (0.63 g, 0.0975 mol) in ethanol (75 mL) and water (50 mL) was heated to reflux for 6 hours. The reaction mixture was allowed to cool to ambient temperature, was concentrated in vacuo and the resultant aqueous residue was partitioned between ethyl acetate and water. The organic layer was washed with water, brine, dried over magnesium sulfate and concentrated to give a viscous oil. The product was purified by flash chromatography on silica gel (250 mL) eluting with hexane:ethyl acetate (80:20 v:v) to give 13-hydroxydibenzo[d,h][1,3]-dioxonino-12(13H)-one as a crystalline solid, mp 129°–30° (2.5 g, 0.0975 mol). $^1$H NMR (DMSO-d$_6$) δ7.49(t,2H), 7.29–7.08(m,6H), 6.40(d,1H), 5.97(d,1H), 5.92(d,1H), 5.24(d,1H).

Part C. A solution of 13-hydroxy-dibenzo[d,h][1,3]-dioxonino-12(13H)-one (2.0 g, 0.0078 mol), thiourea (0.82 g, 0.0108 mol) and hexanol (25 mL), equipped with a column of 4 Å sieves and a condenser, was heated to 160° for 20 hours under a nitrogen atmosphere. The reaction mixture was allowed to cool to ambient temperature and was diluted with ethyl ether (100 mL) to give a solid. The solid was washed with ethyl ether and dried to give N-(1H,9H-dibenz-[4,5:8,9][1,3]dioxonino-[6,7-d]imidazol)-2-thione as a white crystalline powder (1.6 g, 0.00539 mol), mp >250°. $^1$H NMR (DMSO-d$_6$) δ12.5(s,2H), 7.43–7.08(m,8H), 6.2–5.0(bd,2H).

Part D. Employing the method of Example 118, Part E, but using N-(1H,9H-dibenz-[4,5:8,9][1,3]dioxonino-[6,7-d]imidazol)-2-thione, the title compound was isolated as a white foam, mp 65°–70° (0.85 g, 0.00134 mol). $^1$H NMR (CDCl$_3$) δ10.35–10.10(bs,1H), 7.56(m,1H), 7.30–6.95(m,10H), 6.4(d,1H), 5.70–5.20(bs,2H), 3.40–3.19(m,4H), 3.08(t,2H), 1.85–1.23(m,16H), 0.88(t,3H).

EXAMPLE 212

Preparation of
N'-[5-(1H-dibenz2,3:6,7]oxedino[4,5-d]imidazol-2-ylthio)pentyl]-N-(2,4-difluorophenyl)-N-heptylurea Employing the method of Example 118, Part E, but using 1H-dibenz[2,3:6,7]oxedino[4,5-d]imidazol)-2-thione, the title compound was isolated as a white powder, mp 82°–7° (0.36 g, 0.00059 mol). $^1$H NMR (CDCl$_3$) δ9.75–8.5(bs, 2H), 7.84–7.59(m,3H), 7.43–7.05(m,6H), 5.13–6.53(m,3H), 3.43–3 13(m,6H), 1.75–1.20(m,16H), 0.88(t,3H).

Additional ureas, which are listed in Tables 1 and 2, were prepared or could be prepared analogously according to the procedures listed above.

TABLE 1

| Ex. No. | R$^1$ | R$^2$ | R$^3$ | R$^4$ | n | R$^6$ | mp °C. |
|---|---|---|---|---|---|---|---|
| 1 | C$_6$H$_5$ | C$_6$H$_5$ | H | 2,4-diFC$_6$H$_3$ | 5 | (CH$_2$)$_6$CH$_3$ | 96–98 |
| 2 | C$_6$H$_5$ | C$_6$H$_5$ | H | C$_6$H$_5$ | 5 | (CH$_2$)$_6$CH$_3$ | amorphous solid |
| 3 | C$_6$H$_5$ | C$_6$H$_5$ | H | 2,4-diFC$_6$H$_3$ | 8 | (CH$_2$)$_6$CH$_3$ | 89–91 |
| 4 | C$_6$H$_5$ | C$_6$H$_5$ | H | 2,4-diFC$_6$H$_3$ | 8 | (CH$_2$)$_3$CH$_3$ | 114–115 |
| 5 | C$_6$H$_5$ | C$_6$H$_5$ | H | 2,4-diCH$_3$OC$_6$H$_3$ | 5 | (CH$_2$)$_6$CH$_3$ | glassy solid |
| 6 | C$_6$H$_5$ | C$_6$H$_5$ | CH$_3$ | 2,4-diFC$_6$H$_3$ | 5 | (CH$_2$)$_6$CH$_3$ | oil |
| 7 | C$_6$H$_5$ | C$_6$H$_5$ | H | CH$_3$ | 5 | (CH$_2$)$_6$CH$_3$ | 93–96 |
| 8 | C$_6$H$_5$ | C$_6$H$_5$ | H | n-C$_3$H$_7$ | 5 | (CH$_2$)$_6$CH$_3$ | 78–80 |
| 9 | C$_6$H$_5$ | C$_6$H$_5$ | H | 2,4-diFC$_6$H$_3$ | 2 | (CH$_2$)$_2$CH$_3$ | 189–190 |
| 10 | C$_6$H$_5$ | C$_6$H$_5$ | H | 2,4-diFC$_6$H$_3$ | 10 | (CH$_2$)$_3$CH$_3$ | |
| 11 | C$_6$H$_5$ | C$_6$H$_5$ | H | 2,4-diFC$_6$H$_3$ | 5 | CH$_2$CH$_3$ | |
| 12 | C$_6$H$_5$ | C$_6$H$_5$ | H | 2,4-diFC$_6$H$_3$ | 3 | (CH$_2$)$_8$CH$_3$ | |
| 13 | C$_6$H$_5$ | C$_6$H$_5$ | H | 2,4-diFC$_6$H$_3$ | 3 | (CH$_2$)$_{10}$CH$_3$ | |
| 14 | C$_6$H$_5$ | C$_6$H$_5$ | H | 2,4-diFC$_6$H$_3$ | 10 | (CH$_2$)$_{10}$CH$_3$ | |
| 15 | C$_6$H$_5$ | C$_6$H$_5$ | CH$_3$ | 2,4-diFC$_6$H$_3$ | 8 | (CH$_2$)$_3$CH$_3$ | |
| 16 | C$_6$H$_5$ | C$_6$H$_5$ | n-C$_3$H$_7$ | 2,4-diFC$_6$H$_3$ | 5 | (CH$_2$)$_6$CH$_3$ | |
| 17 | C$_6$H$_5$ | C$_6$H$_5$ | n-C$_6$H$_{13}$ | 2,4-diFC$_6$H$_3$ | 5 | (CH$_2$)$_6$CH$_3$ | |
| 18 | C$_6$H$_5$ | C$_6$H$_5$ | CH$_2$CH=CH$_2$ | 2,4-diFC$_6$H$_3$ | 5 | (CH$_2$)$_6$CH$_3$ | |
| 19 | C$_6$H$_5$ | C$_6$H$_5$ | CH$_2$C$_6$H$_5$ | 2,4-diFC$_6$H$_3$ | 5 | (CH$_2$)$_6$CH$_3$ | |
| 20 | C$_6$H$_5$ | C$_6$H$_5$ | C$_6$H$_5$ | 2,4-diFC$_6$H$_3$ | 5 | (CH$_2$)$_6$CH$_3$ | 99–101 |
| 21 | C$_6$H$_5$ | C$_6$H$_5$ | C$_6$H$_5$ | 2,4-diFC$_6$H$_3$ | 8 | (CH$_2$)$_3$CH$_3$ | |
| 22 | C$_6$H$_5$ | C$_6$H$_5$ | 4-FC$_6$H$_4$ | 2,4-diFC$_6$H$_3$ | 5 | (CH$_2$)$_6$CH$_3$ | |
| 23 | C$_6$H$_5$ | C$_6$H$_5$ | 4-CH$_3$C$_6$H$_4$ | 2,4-diFC$_6$H$_3$ | 5 | (CH$_2$)$_6$CH$_3$ | |
| 24 | C$_6$H$_5$ | C$_6$H$_5$ | 4-CH$_3$OC$_6$H$_4$ | 2,4-diFC$_6$H$_3$ | 5 | (CH$_2$)$_6$CH$_3$ | |
| 25 | C$_6$H$_5$ | C$_6$H$_5$ | 4-CF$_3$C$_6$H$_4$ | 2,4-diFC$_6$H$_3$ | 5 | (CH$_2$)$_6$CH$_3$ | |
| 26 | C$_6$H$_5$ | C$_6$H$_5$ | 4-ClC$_6$H$_4$ | 2,4-diFC$_6$H$_3$ | 5 | (CH$_2$)$_6$CH$_3$ | |
| 27 | C$_6$H$_5$ | C$_6$H$_5$ | 3-FC$_6$H$_4$ | 2,4-diFC$_6$H$_3$ | 5 | (CH$_2$)$_6$CH$_3$ | |
| 28 | C$_6$H$_5$ | C$_6$H$_5$ | 2-FC$_6$H$_4$ | 2,4-diFC$_6$H$_3$ | 5 | (CH$_2$)$_6$CH$_3$ | |
| 29 | C$_6$H$_5$ | C$_6$H$_5$ | 3-CH$_3$OC$_6$H$_4$ | 3-FC$_6$H$_4$ | 5 | (CH$_2$)$_6$CH$_3$ | |
| 30 | C$_6$H$_5$ | C$_6$H$_5$ | 3-CH$_3$OC$_6$H$_4$ | 2,4-diFC$_6$H$_3$ | 5 | (CH$_2$)$_6$CH$_3$ | |
| 31 | C$_6$H$_5$ | C$_6$H$_5$ | 2-CF$_3$C$_6$H$_4$ | 2,4-diFC$_6$H$_3$ | 5 | (CH$_2$)$_6$CH$_3$ | |
| 32 | C$_6$H$_5$ | C$_6$H$_5$ | 4-FC$_6$H$_4$ | 2,4-diFC$_6$H$_3$ | 8 | (CH$_2$)$_3$CH$_3$ | |
| 33 | C$_6$H$_5$ | C$_6$H$_5$ | 2-FC$_6$H$_4$ | 2,4-diFC$_6$H$_3$ | 8 | (CH$_2$)$_3$CH$_3$ | |
| 34 | C$_6$H$_5$ | C$_6$H$_5$ | 3-CH$_3$OC$_6$H$_4$ | 2,4-diFC$_6$H$_3$ | 8 | (CH$_2$)$_3$CH$_3$ | |
| 35 | C$_6$H$_5$ | C$_6$H$_5$ | 4-CH$_3$OC$_6$H$_4$ | 2,4-diFC$_6$H$_3$ | 8 | (CH$_2$)$_3$CH$_3$ | |
| 36 | C$_6$H$_5$ | C$_6$H$_5$ | 4-CH$_3$OC$_6$H$_4$ | C$_6$H$_5$ | 5 | (CH$_2$)$_5$CH$_3$ | |
| 37 | C$_6$H$_5$ | C$_6$H$_5$ | H | 2-CF$_3$C$_6$H$_4$ | 8 | (CH$_2$)$_6$CH$_3$ | |
| 38 | C$_6$H$_5$ | C$_6$H$_5$ | H | 3-CF$_3$C$_6$H$_4$ | 5 | (CH$_2$)$_6$CH$_3$ | |
| 39 | C$_6$H$_5$ | C$_6$H$_5$ | H | 4-CF$_3$C$_6$H$_4$ | 5 | (CH$_2$)$_6$CH$_3$ | |
| 40 | C$_6$H$_5$ | C$_6$H$_5$ | H | 2-CH$_3$C$_6$H$_4$ | 5 | (CH$_2$)$_6$CH$_3$ | |
| 41 | C$_6$H$_5$ | C$_6$H$_5$ | H | 3-CH$_3$C$_6$H$_4$ | 5 | (CH$_2$)$_6$CH$_3$ | |
| 42 | C$_6$H$_5$ | C$_6$H$_5$ | H | 4-CH$_3$C$_6$H$_4$ | 5 | (CH$_2$)$_6$CH$_3$ | |
| 43 | C$_6$H$_5$ | C$_6$H$_5$ | H | 3-C$_2$H$_5$C$_6$H$_4$ | 5 | (CH$_2$)$_6$CH$_3$ | |
| 44 | C$_6$H$_5$ | C$_6$H$_5$ | H | 3-(CH$_3$)$_2$CHC$_6$H$_4$ | 5 | (CH$_2$)$_6$CH$_3$ | |
| 45 | C$_6$H$_5$ | C$_6$H$_5$ | H | 2-BrC$_6$H$_4$ | 5 | (CH$_2$)$_6$CH$_3$ | |
| 50 | C$_6$H$_5$ | C$_6$H$_5$ | H | 3-BrC$_6$H$_4$ | 5 | (CH$_2$)$_6$CH$_3$ | |
| 51 | C$_6$H$_5$ | C$_6$H$_5$ | H | 4-BrC$_6$H$_4$ | 5 | (CH$_2$)$_6$CH$_3$ | |
| 52 | C$_6$H$_5$ | C$_6$H$_5$ | H | 2-FC$_6$H$_4$ | 5 | (CH$_2$)$_6$CH$_3$ | |
| 53 | C$_6$H$_5$ | C$_6$H$_5$ | H | 3-FC$_6$H$_4$ | 5 | (CH$_2$)$_6$CH$_3$ | 124–126 |
| 54 | C$_6$H$_5$ | C$_6$H$_5$ | H | 4-FC$_6$H$_4$ | 5 | (CH$_2$)$_6$CH$_3$ | |
| 55 | C$_6$H$_5$ | C$_6$H$_5$ | H | 3-ClC$_6$H$_4$ | 5 | (CH$_2$)$_6$CH$_3$ | |
| 56 | C$_6$H$_5$ | C$_6$H$_5$ | H | 4-n-C$_4$H$_9$C$_6$H$_4$ | 5 | (CH$_2$)$_6$CH$_3$ | |
| 57 | C$_6$H$_5$ | C$_6$H$_5$ | H | 4-CH$_3$OC$_6$H$_4$ | 5 | (CH$_2$)$_6$CH$_3$ | |
| 58 | C$_6$H$_5$ | C$_6$H$_5$ | H | 4-CH$_3$CH$_2$O$_2$CC$_6$H$_4$ | 5 | (CH$_2$)$_6$CH$_3$ | |
| 59 | C$_6$H$_5$ | C$_6$H$_5$ | H | 2,3-diCH$_3$C$_6$H$_3$ | 5 | (CH$_2$)$_6$CH$_3$ | |
| 60 | C$_6$H$_5$ | C$_6$H$_5$ | H | 2,5-diCH$_3$C$_6$H$_3$ | 5 | (CH$_2$)$_6$CH$_3$ | |
| 61 | C$_6$H$_5$ | C$_6$H$_5$ | H | 2,6-diCH$_3$C$_6$H$_3$ | 5 | (CH$_2$)$_6$CH$_3$ | |
| 62 | C$_6$H$_5$ | C$_6$H$_5$ | H | 2,4-diCH$_3$C$_6$H$_3$ | 5 | (CH$_2$)$_6$CH$_3$ | |
| 63 | C$_6$H$_5$ | C$_6$H$_5$ | H | 2,3-diClC$_6$H$_3$ | 5 | (CH$_2$)$_6$CH$_3$ | |
| 64 | C$_6$H$_5$ | C$_6$H$_5$ | H | 2,6-diClC$_6$H$_3$ | 5 | (CH$_2$)$_6$CH$_3$ | 90–92 |

TABLE 1-continued

Structure:

$$R^1\text{-}C(=N)\text{-}C(R^2)=C\text{-}S\text{-}(CH_2)_n\text{-}N(R^6)\text{-}C(=O)\text{-}NHR^4$$ (imidazole with $R^3$ on N)

| Ex. No. | $R^1$ | $R^2$ | $R^3$ | $R^4$ | n | $R^6$ | mp °C. |
|---|---|---|---|---|---|---|---|
| 65 | $C_6H_5$ | $C_6H_5$ | H | 2,4-diClC$_6$H$_3$ | 5 | (CH$_2$)$_6$CH$_3$ | |
| 66 | $C_6H_5$ | $C_6H_5$ | H | 2,5-diClC$_6$H$_3$ | 5 | (CH$_2$)$_6$CH$_3$ | |
| 67 | $C_6H_5$ | $C_6H_5$ | H | 2,3-diFC$_6$H$_3$ | 5 | (CH$_2$)$_6$CH$_3$ | |
| 68 | $C_6H_5$ | $C_6H_5$ | H | 2,5-diFC$_6$H$_3$ | 5 | (CH$_2$)$_6$CH$_3$ | |
| 69 | $C_6H_5$ | $C_6H_5$ | H | 2,4,6-triClC$_6$H$_2$ | 5 | (CH$_2$)$_6$CH$_3$ | |
| 70 | $C_6H_5$ | $C_6H_5$ | H | 2,4,5-triClC$_6$H$_2$ | 5 | (CH$_2$)$_6$CH$_3$ | |
| 71 | $C_6H_5$ | $C_6H_5$ | H | 2,4,6-triFC$_6$H$_2$ | 5 | (CH$_2$)$_6$CH$_3$ | 78–80 |
| 72 | $C_6H_5$ | $C_6H_5$ | H | 2,4,5-triFC$_6$H$_2$ | 5 | (CH$_2$)$_6$CH$_3$ | |
| 73 | $C_6H_5$ | $C_6H_5$ | H | 3,4,5-triCH$_3$OC$_6$H$_2$ | 5 | (CH$_2$)$_6$CH$_3$ | |
| 74 | $C_6H_5$ | $C_6H_5$ | H | 2,4,6-triCH$_3$C$_6$H$_2$ | 5 | (CH$_2$)$_6$CH$_3$ | |
| 75 | $C_6H_5$ | $C_6H_5$ | H | 4-Cl,2-CH$_3$C$_6$H$_3$ | 5 | (CH$_2$)$_6$CH$_3$ | |
| 76 | $C_6H_5$ | $C_6H_5$ | H | 4-Cl,2,5-diCH$_3$C$_6$H$_2$ | 5 | (CH$_2$)$_6$CH$_3$ | |
| 77 | $C_6H_5$ | $C_6H_5$ | H | 4-Cl,3-CF$_3$C$_6$H$_3$ | 5 | (CH$_2$)$_6$CH$_3$ | |
| 78 | $C_6H_5$ | $C_6H_5$ | H | 4-Cl,2,6-diCH$_3$C$_6$H$_2$ | 5 | (CH$_2$)$_6$CH$_3$ | |
| 79 | $C_6H_5$ | $C_6H_5$ | H | 3-Cl,4-CH$_3$C$_6$H$_3$ | 5 | (CH$_2$)$_6$CH$_3$ | |
| 80 | $C_6H_5$ | $C_6H_5$ | H | 3-Cl,4-FC$_6$H$_3$ | 5 | (CH$_2$)$_6$CH$_3$ | |
| 81 | $C_6H_5$ | $C_6H_5$ | H | 5-Cl,2-CH$_3$OC$_6$H$_3$ | 5 | (CH$_2$)$_6$CH$_3$ | |
| 82 | $C_6H_5$ | $C_6H_5$ | H | 2-Cl,5-CF$_3$C$_6$H$_3$ | 5 | (CH$_2$)$_6$CH$_3$ | |
| 83 | $C_6H_5$ | $C_6H_5$ | H | 4-F,2-CH$_3$C$_6$H$_3$ | 5 | (CH$_2$)$_6$CH$_3$ | |
| 84 | $C_6H_5$ | $C_6H_5$ | H | 4-NO$_2$C$_6$H$_4$ | 5 | (CH$_2$)$_6$CH$_3$ | |
| 85 | $C_6H_5$ | $C_6H_5$ | H | 4-CNC$_6$H$_4$ | 5 | (CH$_2$)$_6$CH$_3$ | 68–70 |
| 86 | $C_6H_5$ | $C_6H_5$ | H | 4-NH$_2$C$_6$H$_4$ | 5 | (CH$_2$)$_6$CH$_3$ | |
| 87 | $C_6H_5$ | $C_6H_5$ | H | 4-CH$_3$NHC$_6$H$_4$ | 5 | (CH$_2$)$_6$CH$_3$ | |
| 88 | $C_6H_5$ | $C_6H_5$ | H | 4-(CH$_3$)$_2$NC$_6$H$_4$ | 5 | (CH$_2$)$_6$CH$_3$ | |
| 89 | $C_6H_5$ | $C_6H_5$ | H | 4-HOC$_6$H$_4$ | 5 | (CH$_2$)$_6$CH$_3$ | |
| 90 | $C_6H_5$ | $C_6H_5$ | H | 2-pyridinyl | 5 | (CH$_2$)$_6$CH$_3$ | oil |
| 91 | $C_6H_5$ | $C_6H_5$ | H | 3-pyridinyl | 5 | (CH$_2$)$_6$CH$_3$ | |
| 92 | $C_6H_5$ | $C_6H_5$ | H | 4-pyridinyl | 5 | (CH$_2$)$_6$CH$_3$ | |
| 93 | $C_6H_5$ | $C_6H_5$ | H | 2,6-pyrimidinyl | 5 | (CH$_2$)$_6$CH$_3$ | |
| 94 | $C_6H_5$ | $C_6H_5$ | H | $C_6H_{11}$ | 5 | (CH$_2$)$_6$CH$_3$ | 95–97 |
| 95 | $C_6H_5$ | $C_6H_5$ | H | $C_5H_9$ | 5 | (CH$_2$)$_6$CH$_3$ | |
| 96 | $C_6H_5$ | $C_6H_5$ | H | n-$C_6H_{13}$ | 5 | (CH$_2$)$_6$CH$_3$ | |
| 97 | $C_6H_5$ | $C_6H_5$ | H | n-$C_8H_{17}$ | 5 | (CH$_2$)$_6$CH$_3$ | oil[a] |
| 98 | $C_6H_5$ | $C_6H_5$ | H | n-$C_3H_7$ | 5 | (CH$_2$)$_6$CH$_3$ | |
| 99 | $C_6H_5$ | $C_6H_5$ | H | CF$_3$ | 5 | (CH$_2$)$_6$CH$_3$ | |
| 100 | $C_6H_5$ | $C_6H_5$ | H | CH$_2$CH=CHCH$_3$ | 5 | (CH$_2$)$_6$CH$_3$ | |
| 101 | $C_6H_5$ | $C_6H_5$ | H | CH$_2$CH=CH$_2$ | 5 | (CH$_2$)$_6$CH$_3$ | |
| 102 | $C_6H_5$ | $C_6H_5$ | H | CH$_2$CH=CHCH$_2$CH$_3$ | 5 | (CH$_2$)$_6$CH$_3$ | |
| 103 | $C_6H_5$ | $C_6H_5$ | H | CH$_2$C≡CCH$_3$ | 5 | (CH$_2$)$_6$CH$_3$ | |
| 104 | $C_6H_5$ | $C_6H_5$ | H | n-$C_4H_9$ | 5 | (CH$_2$)$_6$CH$_3$ | |
| 105 | $C_6H_5$ | $C_6H_5$ | H | CH(CH$_3$)$_2$ | 5 | (CH$_2$)$_6$CH$_3$ | 84–86 |
| 106 | $C_6H_5$ | $C_6H_5$ | H | CF$_2$CF$_3$ | 5 | (CH$_2$)$_6$CH$_3$ | |
| 107 | 2-pyridinyl | 2-pyridinyl | H | 2,4-diFC$_6$H$_3$ | 5 | (CH$_2$)$_6$CH$_3$ | oil[b] |
| 108 | 3-pyridinyl | 3-pyridinyl | H | 2,4-diFC$_6$H$_3$ | 5 | (CH$_2$)$_6$CH$_3$ | |
| 109 | 4-pyridinyl | 4-pyridinyl | H | 2,4-diFC$_6$H$_3$ | 5 | (CH$_2$)$_6$CH$_3$ | |
| 110 | 2-thienyl | 2-thienyl | H | 2,4-diFC$_6$H$_3$ | 5 | (CH$_2$)$_6$CH$_3$ | 75–80 |
| 111 | $C_6H_5CH_2$ | $C_6H_5CH_2$ | H | 2,4-diFC$_6$H$_3$ | 5 | (CH$_2$)$_6$CH$_3$ | |
| 112 | $C_6H_5(CH_2)_2$ | $C_6H_5(CH_2)_2$ | H | 2,4-diFC$_6$H$_3$ | 5 | (CH$_2$)$_6$CH$_3$ | |
| 113 | $C_6H_5(CH_2)_5$ | $C_6H_5(CH_2)_5$ | H | 2,4-diFC$_6$H$_3$ | 5 | (CH$_2$)$_6$CH$_3$ | |
| 114 | 4-FC$_6$H$_4$ | 4-FC$_6$H$_4$ | H | 2,4-diFC$_6$H$_3$ | 5 | (CH$_2$)$_6$CH$_3$ | 82–84 |
| 115 | 4-FC$_6$H$_4$ | 4-FC$_6$H$_4$ | H | 2,4-diFC$_6$H$_3$ | 8 | (CH$_2$)$_6$CH$_3$ | |
| 116 | 4-FC$_6$H$_4$ | 4-FC$_6$H$_4$ | H | n-$C_3H_7$ | 8 | (CH$_2$)$_6$CH$_3$ | |
| 117 | 4-FC$_5$H$_4$ | 4-FC$_6$H$_4$ | H | 2,4,6-triFC$_6$H$_2$ | 5 | (CH$_2$)$_6$CH$_3$ | |
| 118 | 4-CH$_3$OC$_6$H$_4$ | 4-CH$_3$OC$_6$H$_4$ | H | 2,4-diFC$_6$H$_3$ | 5 | (CH$_2$)$_6$CH$_3$ | 55–59 |
| 119 | 4-CH$_3$OC$_6$H$_4$ | 4-CH$_3$OC$_6$H$_4$ | H | 2,4-diFC$_6$H$_3$ | 8 | (CH$_2$)$_6$CH$_3$ | |
| 120 | 4-CH$_3$OC$_6$H$_4$ | 4-CH$_3$OC$_6$H$_4$ | H | n-$C_3H_7$ | 8 | (CH$_2$)$_6$CH$_3$ | |
| 121 | 4-CH$_3$OC$_6$H$_4$ | 4-CH$_3$OC$_6$H$_4$ | H | 2,4,6-triFC$_6$H$_2$ | 5 | (CH$_2$)$_6$CH$_3$ | |
| 122 | 4-CH$_3$C$_6$H$_4$ | 4-CH$_3$C$_6$H$_4$ | H | 2,4-diFC$_6$H$_3$ | 5 | (CH$_2$)$_6$CH$_3$ | 63–65[c] |
| 123 | 4-CH$_3$C$_6$H$_4$ | 4-CH$_3$C$_6$H$_4$ | H | 2,4-diFC$_6$H$_3$ | 8 | (CH$_2$)$_6$CH$_3$ | |
| 124 | 4-CH$_3$C$_6$H$_4$ | 4-CH$_3$C$_6$H$_4$ | H | n-$C_3H_7$ | 8 | (CH$_2$)$_6$CH$_3$ | |
| 125 | 4-CH$_3$C$_6$H$_4$ | 4-CH$_3$C$_6$H$_4$ | H | 2,4,6-triFC$_6$H$_2$ | 5 | (CH$_2$)$_6$CH$_3$ | |
| 126 | 4-(CH$_3$)$_2$NC$_6$H$_4$ | 4-(CH$_3$)$_2$NHC$_6$H$_4$ | H | CH$_3$ | 8 | (CH$_2$)$_6$CH$_3$ | |
| 127 | 4-NO$_2$C$_6$H$_4$ | 4-NO$_2$C$_6$H$_4$ | H | 2,4-diFC$_6$H$_3$ | 5 | (CH$_2$)$_6$CH$_3$ | |
| 128 | $C_6H_5$ | 4-CH$_3$SC$_6$H$_4$ | H | 2,4-diFC$_6$H$_3$ | 5 | (CH$_2$)$_6$CH$_3$ | |
| 129 | $C_6H_5$ | 4-CH$_3$SOC$_6$H$_4$ | H | 2,4-diFC$_6$H$_3$ | 5 | (CH$_2$)$_6$CH$_3$ | |
| 130 | $C_6H_5$ | 4-CH$_3$SO$_2$C$_6$H$_4$ | H | 2,4-diFC$_6$H$_3$ | 5 | (CH$_2$)$_6$CH$_3$ | |
| 131 | 4-ClC$_6$H$_4$ | 4-ClC$_6$H$_4$ | H | 2,4-diCH$_3$OC$_6$H$_3$ | 5 | (CH$_2$)$_6$CH$_3$ | |
| 132 | 4-BrC$_6$H$_4$ | 4-BrC$_6$H$_4$ | H | 2,4-diCH$_3$C$_6$H$_3$ | 8 | (CH$_2$)$_6$CH$_3$ | |
| 133 | $C_6H_5$ | 4-FC$_6$H$_4$ | H | 2,4,6-triFC$_6$H$_2$ | 8 | (CH$_2$)$_6$CH$_3$ | |
| 134 | 4-CF$_3$C$_6$H$_4$ | 4-CF$_3$C$_6$H$_4$ | H | 4-FC$_6$H$_4$ | 5 | (CH$_2$)$_6$CH$_3$ | |
| 135 | 2-ClC$_6$H$_4$ | 2-ClC$_6$H$_4$ | H | 2,4,6-triFC$_6$H$_2$ | 4 | (CH$_2$)$_7$CH$_3$ | |
| 136 | 3-ClC$_6$H$_4$ | 3-ClC$_6$H$_4$ | H | 2,4-diCH$_3$OC$_6$H$_3$ | 6 | (CH$_2$)$_8$CH$_3$ | |
| 137 | 4-ClC$_6$H$_4$ | 4-ClC$_6$H$_4$ | H | 2,4-diFC$_6$H$_3$ | 5 | (CH$_2$)$_6$CH$_3$ | 55–57[d] |

TABLE 1-continued

Structure: R¹ and R² on a pyrimidine-like ring with N, N-R³, and S—(CH$_2$)$_n$—N(R⁶)—C(O)—NHR⁴ substituent.

| Ex. No. | R¹ | R² | R³ | R⁴ | n | R⁶ | mp °C. |
|---|---|---|---|---|---|---|---|
| 138 | 4-FC$_6$H$_4$ | 3-ClC$_6$H$_4$ | H | 2,4-diFC$_6$H$_3$ | 5 | (CH$_2$)$_6$CH$_3$ | |
| 139 | 4-nC$_4$H$_9$C$_6$H$_4$ | 4-nC$_4$H$_9$C$_6$H$_4$ | H | C$_6$H$_5$ | 5 | (CH$_2$)$_6$CH$_3$ | |
| 140 | 3,4-diClC$_6$H$_3$ | C$_6$H$_5$ | H | n-C$_3$H$_7$ | 6 | (CH$_2$)$_6$CH$_3$ | |
| 141 | C$_6$H$_5$ | 3-pyridinyl | H | C$_6$H$_{11}$ | 5 | (CH$_2$)$_6$CH$_3$ | |
| 142 | C$_6$H$_5$ | 3-pyridinyl | H | 2,4-diFC$_6$H$_3$ | 5 | (CH$_2$)$_6$CH$_3$ | |
| 143 | C$_6$H$_5$ | 3-pyridinyl | H | 2,4-diFC$_6$H$_3$ | 8 | (CH$_2$)$_6$CH$_3$ | |
| 144 | C$_6$H$_5$ | 3-pyridinyl | H | n-C$_3$H$_7$ | 8 | (CH$_2$)$_6$CH$_3$ | |
| 145 | 4-FC$_6$H$_4$ | 3-pyridinyl | H | 2,4,6-triFC$_6$H$_2$ | 5 | (CH$_2$)$_6$CH$_3$ | |
| 146 | 4-CH$_3$OC$_6$H$_4$ | 3-pyridinyl | H | 2,4,6-triFC$_6$H$_2$ | 6 | (CH$_2$)$_6$CH$_3$ | |
| 147 | C$_6$H$_5$ | 2-thienyl | H | 2,4-diFC$_6$H$_3$ | 4 | (CH$_2$)$_7$CH$_3$ | |
| 148 | 4-FC$_6$H$_4$ | 2-thienyl | H | C$_6$H$_5$ | 5 | (CH$_2$)$_6$CH$_3$ | |
| 149 | 4-CH$_3$OC$_6$H$_4$ | 2-thienyl | H | 2,4-diCH$_3$OC$_6$H$_3$ | 5 | (CH$_2$)$_6$CH$_3$ | |
| 150 | C$_6$H$_5$ | 4-pyridinyl | H | 2,4-diFC$_6$H$_3$ | 5 | (CH$_2$)$_6$CH$_3$ | |
| 151 | 4-FC$_6$H$_4$ | 4-pyridinyl | H | C$_6$H$_5$ | 5 | (CH$_2$)$_6$CH$_3$ | |
| 152 | 4-CH$_3$OC$_6$H$_4$ | 4-pyridinyl | H | 2,4-diCH$_3$C$_6$H$_3$ | 6 | (CH$_2$)$_7$CH$_3$ | |
| 153 | C$_6$H$_5$ | 2-pyridinyl | H | 2,4-diFC$_6$H$_3$ | 5 | (CH$_2$)$_6$CH$_3$ | |
| 154 | 3-F,4-ClC$_6$H$_3$ | C$_6$H$_5$ | H | 2,4-diFC$_6$H$_3$ | 5 | (CH$_2$)$_6$CH$_3$ | |
| 155 | 4-CH$_3$OC$_6$H$_4$ | 4-FC$_6$H$_4$ | H | C$_6$H$_5$ | 8 | (CH$_2$)$_6$CH$_3$ | |
| 156 | 4-FC$_6$H$_4$ | C$_6$H$_5$ | H | 2,4-diFC$_6$H$_3$ | 5 | (CH$_2$)$_6$CH$_3$ | |
| 157 | 4-BrC$_6$H$_4$ | C$_6$H$_5$ | H | 2,4-diFC$_6$H$_3$ | 5 | (CH$_2$)$_6$CH$_3$ | |
| 158 | 4-CH$_3$OC$_6$H$_4$ | C$_6$H$_5$ | H | 2,4-diCH$_3$OC$_6$H$_3$ | 8 | (CH$_2$)$_6$CH$_3$ | |
| 159 | 3,4-diCH$_3$OC$_6$H$_3$ | 3,4-diCH$_3$OC$_6$H$_3$ | H | C$_6$H$_5$ | 9 | (CH$_2$)$_5$CH$_3$ | |
| 160 | C$_6$H$_5$ | H | H | 2,4-diFC$_6$H$_3$ | 5 | (CH$_2$)$_6$CH$_3$ | oil$^{(e)}$ |
| 161 | C$_6$H$_5$ | H | H | 2,4-diCH$_3$OC$_6$H$_3$ | 5 | (CH$_2$)$_6$CH$_3$ | |
| 162 | C$_6$H$_5$ | H | H | 2,4-diFC$_6$H$_3$ | 8 | (CH$_2$)$_6$CH$_3$ | |
| 163 | C$_6$H$_5$ | H | H | n-C$_3$H$_7$ | 5 | (CH$_2$)$_6$CH$_3$ | |
| 164 | 4-FC$_6$H$_4$ | H | H | 2,4-diFC$_6$H$_3$ | 5 | (CH$_2$)$_6$CH$_3$ | |
| 165 | 4-CH$_3$OC$_6$H$_4$ | H | H | 2,4-diFC$_6$H$_3$ | 8 | (CH$_2$)$_6$CH$_3$ | |
| 166 | C$_6$H$_5$ | H | H | C$_6$H$_5$ | 8 | (CH$_2$)$_6$CH$_3$ | |
| 167 | C$_6$H$_5$ | CH$_3$ | H | 2,4-diFC$_6$H$_3$ | 5 | (CH$_2$)$_6$CH$_3$ | |
| 168 | C$_6$H$_5$ | CH$_3$ | H | 2,4-diFC$_6$H$_3$ | 8 | (CH$_2$)$_6$CH$_3$ | |
| 169 | C$_6$H$_5$ | CH$_3$ | H | n-C$_3$H$_7$ | 8 | (CH$_2$)$_6$CH$_3$ | |
| 170 | C$_6$H$_5$ | CH$_3$ | H | 2,4-diCH$_3$OC$_6$H$_3$ | 8 | (CH$_2$)$_6$CH$_3$ | |
| 171 | 4-FC$_6$H$_4$ | CH$_3$ | H | 2,5-diClC$_6$H$_3$ | 5 | (CH$_2$)$_6$CH$_3$ | |
| 172 | C$_6$H$_5$ | n-C$_4$H$_9$ | H | 2,4-diFC$_6$H$_3$ | 5 | (CH$_2$)$_6$CH$_3$ | |
| 173 | C$_6$H$_5$ | n-C$_4$H$_9$ | H | 2,4-diFC$_6$H$_3$ | 8 | (CH$_2$)$_6$CH$_3$ | |
| 174 | C$_6$H$_5$ | n-C$_4$H$_9$ | H | 2,4-diCH$_3$OC$_6$H$_3$ | 5 | (CH$_2$)$_6$CH$_3$ | |
| 175 | C$_6$H$_5$ | n-C$_4$H$_9$ | H | n-C$_3$H$_7$ | 7 | (CH$_2$)$_6$CH$_3$ | |
| 176 | C$_6$H$_5$ | n-C$_8$H$_{17}$ | H | n-C$_3$H$_7$ | 9 | (CH$_2$)$_5$CH$_3$ | |
| 177 | C$_6$H$_5$ | n-C$_8$H$_{17}$ | H | 2,4-diClC$_6$H$_3$ | 4 | (CH$_2$)$_7$CH$_3$ | |
| 178 | C$_6$H$_5$ | C$_5$H$_9$ | H | 2,4-diFC$_6$H$_3$ | 8 | (CH$_2$)$_6$CH$_3$ | |
| 179 | C$_6$H$_5$ | C$_5$H$_9$ | H | 2,4,5-triClC$_6$H$_2$ | 5 | (CH$_2$)$_6$CH$_3$ | |
| 180 | 4-CH$_3$OC$_6$H$_4$ | C$_6$H$_{11}$ | H | C$_6$H$_5$ | 5 | (CH$_2$)$_8$CH$_3$ | |
| 181 | C$_6$H$_5$ | C$_6$H$_{11}$—CH$_2$ | H | 2,4-diFC$_6$H$_3$ | 5 | (CH$_2$)$_5$CH$_3$ | |
| 182 | C$_6$H$_5$ | C$_6$H$_{11}$—(CH$_2$)$_2$ | H | 2,4-diFC$_6$H$_3$ | 5 | (CH$_2$)$_6$CH$_3$ | |
| 183 | CH$_3$ | CH$_3$ | H | 2,4-diFC$_6$H$_3$ | 5 | (CH$_2$)$_6$CH$_3$ | |
| 184 | CH$_3$ | CH$_3$ | H | n-C$_3$H$_7$ | 8 | (CH$_2$)$_6$CH$_3$ | |
| 185 | n-C$_4$H$_9$ | n-C$_4$H$_9$ | H | 2,4,6-triFC$_6$H$_2$ | 8 | (CH$_2$)$_6$CH$_3$ | |
| 186 | H | H | H | 2,4-diFC$_6$H$_3$ | 5 | (CH$_2$)$_6$CH$_3$ | oil$^{(f)}$ |
| 187 | H | H | H | 2,4-diFC$_6$H$_3$ | 8 | (CH$_2$)$_6$CH$_3$ | |
| 188 | (CH$_3$)$_2$CH | (CH$_3$)$_2$CH | H | 2,4-diFC$_6$H$_3$ | 5 | (CH$_2$)$_6$CH$_3$ | 91–93 |
| 189 | C$_6$H$_5$ | C$_6$H$_5$ | H | 2,4-diFC$_6$H$_3$ | 2 | (CH$_2$)$_6$CH$_3$ | 144–146 |
| 190 | C$_6$H$_5$ | C$_6$H$_5$ | H | 2,4-diFC$_6$H$_3$ | 5 | (CH$_2$)$_2$CH$_3$ | 68–70 |
| 191 | C$_6$H$_5$ | C$_6$H$_5$ | H | 2,4-diFC$_6$H$_3$ | 5 | (CH$_2$)$_7$CH$_3$ | |
| 192 | C$_6$H$_5$ | C$_6$H$_5$ | H | (C$_6$H$_4$)(C$_6$H$_5$) | 5 | (CH$_2$)$_6$CH$_3$ | 119–121 |
| 193 | CH$_3$CH$_2$CH$_2$ | CH$_3$CH$_2$CH$_2$ | H | 2,4-diFC$_6$H$_3$ | 5 | (CH$_2$)$_6$CH$_3$ | 78–80 |
| 194 | 2-pyridinyl | 2-pyridinyl | H | 2,4-diFC$_6$H$_3$ | 5 | (CH$_2$)$_6$CH$_3$ | 80–83 (HCl salt) |
| 195 | 3-CH$_3$OC$_6$H$_4$ | 3-CH$_3$OC$_6$H$_4$ | H | 2,4-diFC$_6$H$_3$ | 5 | (CH$_2$)$_6$CH$_3$ | 100–102 |
| 196 | 2-CH$_3$OC$_6$H$_4$ | 2-CH$_3$OC$_6$H$_4$ | H | 2,4-diFC$_6$H$_3$ | 5 | (CH$_2$)$_6$CH$_3$ | oil$^{(g)}$ |
| 197 | 4-(CH$_3$)$_2$NC$_6$H$_4$ | 4-(CH$_3$)$_2$NC$_6$H$_4$ | H | 2,4-diFC$_6$H$_3$ | 5 | (CH$_2$)$_6$CH$_3$ | 68–70$^{(h)}$ |
| 198 | 4-(CH$_3$)$_2$NC$_6$H$_4$ | 4-(CH$_3$)$_2$NC$_6$H$_4$ | H | 2,4-diFC$_6$H$_3$ | 5 | (CH$_2$)$_6$CH$_3$ | 142–145 (HCl salt) |
| 199 | C$_6$H$_{11}$ | C$_6$H$_{11}$ | H | 2,4-diFC$_6$H$_3$ | 5 | (CH$_2$)$_6$CH$_3$ | 55–58$^{(i)}$ |
| 200 | C$_6$H$_5$ | 4-(CH$_3$)$_2$NC$_6$H$_4$ | H | 2,4-diFC$_6$H$_3$ | 5 | (CH$_2$)$_6$CH$_3$ | oil$^{(j)}$ |
| 201 | 2-furanyl | 2-furanyl | H | 2,4-diFC$_6$H$_3$ | 5 | (CH$_2$)$_6$CH$_3$ | liq$^{(k)}$ |
| 202 | 4-CH$_3$OC$_6$H$_4$ | 4-CH$_3$OC$_6$H$_4$ | H | CH$_2$(CH$_3$)$_2$ | 5 | (CH$_2$)$_6$CH$_3$ | oil$^{(l)}$ |
| 203 | 4-(t-C$_4$H$_9$)C$_6$H$_4$ | 4-(t-C$_4$H$_9$)C$_6$H$_4$ | H | 2,4-diFC$_6$H$_3$ | 5 | (CH$_2$)$_6$CH$_3$ | 78–80$^{(m)}$ |
| 204 | 4-CH$_3$OC$_6$H$_4$ | 4-CH$_3$OC$_6$H$_4$ | H | 2,4-diFC$_6$H$_3$ | 5 | CH$_3$ | 65–75$^{(n)}$ |
| 205 | 4-(CH$_3$)$_2$NC$_6$H$_4$ | 4-(CH$_3$)$_2$NC$_6$H$_4$ | H | CH(CH$_3$)$_2$ | 5 | (CH$_2$)$_6$CH$_3$ | 70–72$^{(o)}$ |
| 206 | C$_6$H$_5$ | C$_6$H$_5$ | H | (CH$_2$)$_7$CH$_3$ | 5 | 2,4-diFC$_6$H$_3$ | oil$^{(p)}$ |
| 207 | C$_6$H$_5$ | C$_6$H$_5$ | H | (CH$_2$)$_7$CH$_3$ | 5 | C$_6$H$_5$ | 74–76 |
| 208 | C$_6$H$_5$ | C$_6$H$_5$ | H | (CH$_2$)$_7$CH$_3$ | 5 | 2,4,6-triFC$_6$H$_2$ | 99–101 |

TABLE 1-continued

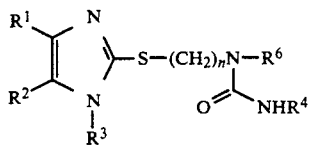

| Ex. No. | $R^1$ | $R^2$ | $R^3$ | $R^4$ | n | $R^6$ | mp °C. |
|---|---|---|---|---|---|---|---|
| 209 | 4-HOC$_6$H$_4$ | 4-HOC$_6$H$_4$ | H | 2,4-diFC$_6$H$_3$ | 5 | (CH$_2$)$_6$CH$_3$ | 110–112 |
| 210 | (CH$_3$)$_2$CH | (CH$_3$)$_2$CH | H | CH(CH$_3$)$_2$ | 5 | (CH$_2$)$_6$CH$_3$ | oil$^{(q)}$ |
| 211 | C$_6$H$_4$-2-OCH$_2$O-2'-C$_6$H$_4$ | | H | 2,4-diFC$_6$H$_3$ | 5 | (CH$_2$)$_6$CH$_3$ | 65–70 |
| 212 | C$_6$H$_4$OC$_6$H$_4$ | | H | 2,4-diFC$_6$H$_3$ | 5 | (CH$_2$)$_6$CH$_3$ | 82–87 |
| 213 | n-C$_3$H$_7$ | n-C$_3$H$_7$ | H | n-C$_3$H$_7$ | 5 | (CH$_2$)$_6$CH$_3$ | |
| 214 | 2-pyridinyl | 2-pyridinyl | H | C$_6$H$_{11}$ | 5 | (CH$_2$)$_6$CH$_3$ | |
| 215 | 3-pyridinyl | 3-pyridinyl | H | 2,4-diCH$_3$OC$_6$H$_3$ | 5 | (CH$_2$)$_6$CH$_3$ | |
| 216 | 4-pyridinyl | 4-pyridinyl | H | 2,4,6-triFC$_6$H$_2$ | 5 | (CH$_2$)$_6$CH$_3$ | |
| 217 | 2-CH$_3$OC$_6$H$_4$ | 2-CH$_3$OC$_6$H$_4$ | H | 3-FC$_6$H$_4$ | 5 | (CH$_2$)$_6$CH$_3$ | |
| 218 | 3-CH$_3$OC$_6$H$_4$ | 3-CH$_3$OC$_6$H$_4$ | H | CH(CH$_3$)$_2$ | 5 | (CH$_2$)$_6$CH$_3$ | |
| 219 | C$_6$H$_{11}$ | C$_6$H$_{11}$ | H | C$_6$H$_5$ | 5 | (CH$_2$)$_6$CH$_3$ | |
| 220 | C$_6$H$_5$ | 4-(CH$_3$)$_2$NC$_6$H$_4$ | H | (CH$_2$)$_7$CH$_3$ | 5 | (CH$_2$)$_6$CH$_3$ | |
| 221 | 2-furanyl | 2-furanyl | H | 2,6-diClC$_6$H$_3$ | 5 | (CH$_2$)$_6$CH$_3$ | |
| 222 | 4-(t-C$_4$H$_9$)C$_6$H$_4$ | 4-(t-C$_4$H$_9$)C$_6$H$_4$ | H | CH$_3$ | 5 | (CH$_2$)$_6$CH$_3$ | |
| 223 | 2-thienyl | 2-thienyl | H | (C$_6$H$_4$)(C$_6$H$_5$) | 5 | (CH$_2$)$_6$CH$_3$ | |
| 224 | 4-HO—C$_6$H$_4$ | 4-HO—C$_6$H$_4$ | CH$_3$ | 2,4-diFC$_6$H$_3$ | 5 | (CH$_2$)$_6$CH$_3$ | |
| 225 | (CH$_3$)$_2$CH | (CH$_3$)$_2$CH | CH$_3$ | C$_6$H$_{11}$ | 5 | (CH$_2$)$_6$CH$_3$ | |
| 226 | C$_6$H$_5$—CH$_2$ | C$_6$H$_5$—CH$_2$ | CH$_3$ | C$_6$H$_5$ | 5 | (CH$_2$)$_6$CH$_3$ | |
| 227 | C$_6$H$_4$-2-OCH$_2$O-2'-C$_6$H$_4$ | | H | 2,4-diFC$_6$H$_3$ | 3 | (CH$_2$)$_6$CH$_3$ | |
| 228 | C$_6$H$_4$OC$_6$H$_4$ | | H | C$_6$H$_{11}$ | 3 | (CH$_2$)$_6$CH$_3$ | |
| 229 | 4-CH$_3$OC$_6$H$_4$ | 4-CH$_3$C$_6$H$_4$ | H | 2,4-diFC$_6$H$_3$ | 8 | (CH$_2$)$_6$CH$_3$ | |
| 230 | 4-CH$_3$OC$_6$H$_4$ | 4-(CH$_3$)$_2$NC$_6$H$_4$ | H | C$_6$H$_{11}$ | 8 | (CH$_2$)$_6$CH$_3$ | |
| 231 | 4-CH$_3$OC$_6$H$_4$ | C$_6$H$_{11}$ | H | 2,4-diFC$_6$H$_3$ | 5 | (CH$_2$)$_3$CH$_3$ | |
| 232 | 4-CH$_3$OC$_6$H$_4$ | (CH$_3$)$_2$CH | H | 2,4-diFC$_6$H$_3$ | 5 | (CH$_2$)$_8$CH$_3$ | |
| 233 | 4-(CH$_3$)$_2$NC$_6$H$_4$ | C$_6$H$_{11}$ | H | 2,4-diFC$_6$H$_3$ | 5 | CH$_3$ | |
| 234 | 4-(CH$_3$)$_2$NC$_6$H$_4$ | (CH$_3$)$_2$CH | H | 2,4-diFC$_6$H$_3$ | 5 | C$_6$H$_5$ | |
| 235 | C$_6$H$_{11}$ | (CH$_3$)$_2$CH | CH$_2$CH$_3$ | 2,4-diFC$_6$H$_3$ | 5 | 3-FC$_6$H$_4$ | |
| 236 | C$_6$H$_5$ | 4-CH$_3$OC$_6$H$_4$ | C$_6$H$_5$ | (CH$_2$)$_7$CH$_3$ | 5 | (CH$_2$)$_3$CH$_3$ | |
| 237 | C$_6$H$_5$ | 4-(CH$_3$)$_2$NC$_6$H$_4$ | CH$_2$C$_6$H$_5$ | (CH$_2$)$_7$CH$_3$ | 5 | C$_6$H$_5$ | |
| 238 | C$_6$H$_5$ | C$_6$H$_{11}$ | H | n-C$_3$H$_7$ | 5 | (CH$_2$)$_6$CH$_3$ | |
| 239 | C$_6$H$_5$ | (CH$_3$)$_2$CH | H | C$_6$H$_{11}$ | 5 | (CH$_2$)$_6$CH$_3$ | |
| 240 | 4-CH$_3$SC$_6$H$_4$ | 4-CH$_3$SC$_6$H$_4$ | H | 2,4-diCH$_3$OC$_6$H$_3$ | 5 | (CH$_2$)$_6$CH$_3$ | |
| 241 | 4-CH$_3$SC$_6$H$_4$ | 4-CH$_3$SC$_6$H$_4$ | H | 2,4,6-triFC$_6$H$_2$ | 5 | (CH$_2$)$_6$CH$_3$ | |
| 242 | 4-CH$_3$SO$_2$C$_6$H$_4$ | 4-CH$_3$SO$_2$C$_6$H$_4$ | H | 3-FC$_6$H$_4$ | 5 | (CH$_2$)$_6$CH$_3$ | |
| 243 | C$_6$H$_5$ | 4-CH$_3$SC$_6$H$_4$ | H | CH(CH$_3$)$_2$ | 5 | (CH$_2$)$_6$CH$_3$ | |
| 244 | C$_6$H$_5$ | 4-CH$_3$SOC$_6$H$_4$ | H | C$_6$H$_5$ | 5 | (CH$_2$)$_6$CH$_3$ | |
| 245 | C$_6$H$_5$ | 4-CH$_3$SO$_2$C$_6$H$_4$ | H | (CH$_2$)$_7$CH$_3$ | 5 | (CH$_2$)$_6$CH$_3$ | |
| 246 | 4-CH$_3$OC$_6$H$_4$ | 4-CH$_3$OC$_6$H$_4$ | H | n-C$_3$H$_7$ | 5 | (CH$_2$)$_6$CH$_3$ | |
| 247 | 4-CH$_3$OC$_6$H$_4$ | 4-CH$_3$OC$_6$H$_4$ | H | C$_6$H$_{11}$ | 5 | (CH$_2$)$_6$CH$_3$ | |
| 248 | 4-CH$_3$OC$_6$H$_4$ | 4-CH$_3$OC$_6$H$_4$ | H | C$_6$H$_5$ | 5 | (CH$_2$)$_6$CH$_3$ | |
| 249 | 4-CH$_3$OC$_6$H$_4$ | 4-CH$_3$OC$_6$H$_4$ | H | 2,4-diFC$_6$H$_3$ | 3 | (CH$_2$)$_6$CH$_3$ | |
| 250 | 4-CH$_3$OC$_6$H$_4$ | 4-CH$_3$OC$_6$H$_4$ | H | C$_6$H$_{11}$ | 8 | (CH$_2$)$_6$CH$_3$ | |
| 251 | 4-CH$_3$OC$_6$H$_4$ | 4-CH$_3$OC$_6$H$_4$ | H | (CH$_2$)$_7$CH$_3$ | 5 | C$_6$H$_5$ | |
| 252 | 4-(CH$_3$)$_2$NC$_6$H$_4$ | 4-(CH$_3$)$_2$NC$_6$H$_4$ | H | n-C$_3$H$_7$ | 5 | (CH$_2$)$_6$CH$_3$ | |
| 253 | 4-(CH$_3$)$_2$NC$_6$H$_4$ | 4-(CH$_3$)$_2$NC$_6$H$_4$ | H | C$_6$H$_{11}$ | 5 | (CH$_2$)$_6$CH$_3$ | |
| 254 | 4-(CH$_3$)$_2$NC$_6$H$_4$ | 4-(CH$_3$)$_2$NC$_6$H$_4$ | H | C$_6$H$_5$ | 5 | (CH$_2$)$_6$CH$_3$ | |
| 255 | 4-(CH$_3$)$_2$NC$_6$H$_4$ | 4-(CH$_3$)$_2$NC$_6$H$_4$ | H | 2,4-diFC$_6$H$_3$ | 3 | (CH$_2$)$_6$CH$_3$ | |
| 256 | 4-(CH$_3$)$_2$NC$_6$H$_4$ | 4-(CH$_3$)$_2$NC$_6$H$_4$ | H | C$_6$H$_{11}$ | 8 | (CH$_2$)$_6$CH$_3$ | |
| 257 | 4-(CH$_3$)$_2$NC$_6$H$_4$ | 4-(CH$_3$)$_2$NC$_6$H$_4$ | H | (CH$_2$)$_7$CH$_3$ | 5 | C$_6$H$_5$ | |
| 258 | 4-CF$_3$C$_6$H$_4$ | 4-CF$_3$C$_6$H$_4$ | H | 2,4-diFC$_6$H$_3$ | 5 | (CH$_2$)$_6$CH$_3$ | oil$^{(r)}$ |
| 259 | C$_6$H$_5$ | H | C$_6$H$_5$ | 2,4-diFC$_6$H$_3$ | 5 | (CH$_2$)$_6$CH$_3$ | oil$^{(s)}$ |
| 260 | H | C$_6$H$_5$ | C$_6$H$_5$ | 2,4-diFC$_6$H$_3$ | 5 | (CH$_2$)$_6$CH$_3$ | oil$^{(t)}$ |
| 261 | C$_6$H$_5$ | C$_6$H$_5$ | H | CH(CH$_3$)$_2$ | 5 | C$_6$H$_5$ | 55–59 |
| 262 | C$_6$H$_5$ | C$_6$H$_5$ | H | CH(CH$_3$)$_2$ | 8 | (CH$_2$)$_3$CH$_3$ | 110–112 |
| 263 | C$_6$H$_5$ | C$_6$H$_5$ | H | CH(CH$_3$)$_2$ | 5 | 2,4-diFC$_6$H$_3$ | 46–50 |
| 264 | 4-CH$_3$O—C$_6$H$_4$ | 4-CH$_3$O—C$_6$H$_4$ | H | CH(CH$_3$)$_2$ | 5 | 4-(CH$_3$)$_2$NC$_6$H$_4$ | 76–80 |
| 265 | C$_6$H$_5$ | C$_6$H$_5$ | H | CH(CH$_3$)$_2$ | 5 | 4-(CH$_3$)$_2$NC$_6$H$_4$ | 166–167 |

TABLE 1-continued

[Structure: R¹ and R² on a carbon-carbon double bond attached to an imidazole ring with N-R³, with substituent —S—(CH₂)ₙN—R⁶ and a C(=O)NHR⁴ group]

| Ex. No. | R¹ | R² | R³ | R⁴ | n | R⁶ | mp °C. |
|---|---|---|---|---|---|---|---|
| 266 | $C_6H_5$ | $C_6H_5$ | H | 2,6-di[$(CH_3)_2CH$]$C_6H_3$ | 5 | $(CH_2)_6CH_3$ | 185–187 |

Footnotes to Table 1

(a)¹H NMR (CDCl₃) δ 11.6(s, 1H), 7.7–7.1(m, 10H), 4.4(t, 1H, J=5Hz), 3.4(t, 2H, H=6.7Hz), 3.2–3.9(m, 5H), 1.8–1.0(m, 29H), 1.0–0.8(m, 7H).

(b)¹H NMR (CDCl₃) δ 8.79–7.63(m, 7H), 7.29–7.12(m, 2H), 6.87–6.73(m, 2H), 6.44(bs, 1H), 3.34–3.08(m, 6H), 1.83–1.18(m, 16H), 0.86(t, 3H).

(c)¹H NMR (CDCl₃) δ 10.6–10.0(bs, 1H), 7.80(m, 1H), 7.35–7.00(m, 8H), 6.8–6.57(m, 2H), 6.4(bs, 1H), 3.89(t, 2H), 3.25(t, 2H), 3.00(t, 2H), 2.33(s, 3H), 2.32(s, 3H), 1.79–1.29(m, 16H), 0.88(t, 3H).

(d)¹H NMR (CDCl₃) δ 11.1–11.0(bs, 1H), 7.64(m, 1H), 7.5(d, 2H), 7.27(m, 6H), 6.75(m, 1H), 6.53(m, 1H), 6.33(bs, 1H), 3.45(t, 2H), 3.26(t, 2H), 2.98(t, 2H), 1.82–1.25(m, 16H), 0.90(t, 3H).

(e)¹H NMR (CDCl₃) δ 10.8–10.7(m, 1H), 8.0–7.2(m, 7H), 6.9–6.6(m, 2H), 6.0–5.9(m, 1H), 3.4(t, 2H, J=6.6Hz), 3.3(t, 2H, J=7.6Hz), 3.0(t, 2H, J=6.5Hz), 1.9–1.2(m, 18H), 0.9(t, 3H, J=7.2Hz).

(f)¹H NMR (CDCl₃) δ 10.4–10.1(m, 1H), 8.0–7.8(m, 1H), 7.2–6.9(m, 2H), 6.9–6.75(m, 2H), 6.5–6.4(m, 1H), 3.4–3.2(m, 4H), 3.0(t, 2H, J=7Hz), 1.9–1.1(m, 19H), 0.9(t, 3H, J=8Hz).

(g)¹H NMR (DMSO-d₆) δ 12.17(bs, 1H), 7.94(bs, 1H), 7.43–6.77(m, 11H), 3.57(s, 3H), 3.24(m, 4H), 3.19(s, 3H), 3.07(t, 2H, 1.76–1.18(m, 16H), 0.85(t, 3H).

(h)¹H NMR (CDCl₃) δ 10.03–9.55(bs, 1H), 7.86(m, 1H), 7.58–7.20(bm, 4H), 6.82–6.61(m, 4H), 6.42(bs, 1H), 3.30–3.21(m, 2H), 2.94(bs, 14H), 1.78–1.26(m, 16H), 0.88(t, 3H).

(i)¹H NMR (CDCl₃) δ 9.50–9.18(bs, 1H), 7.97(m, 1H), 6.80(m, 2H), 6.41(bs, 1H), 3.31(m, 4H), 2.86(t, 2H), 2.68–2.37(m, 2H), 1.91–1.13(m, 36H), 0.89(t, 3H).

(j)¹H NMR (CDCl₃) δ 10.2–9.8(bs, 1H), 7.85(m, 1H), 7.70–7.16(m, 7H), 6.75(m, 1H), 6.89(d, 3H), 6.39(bs, 1H), 3.38(t, 2H), 3.25(t, 2H), 3.01(t, 2H), 2.95(s, 6H), 1.85–1.25(m, 16H), 0.9(t, 3H).

(k)¹H NMR (CDCl₃) δ 10.35–10.15(bs, 1H), 7.95(m, 1H), 7.50–7.36(m, 2H), 6.98–6.69(m, 4H), 6.49–6.38(m, 3H), 3.35(t, 2H), 3.25(t, 2H), 3.05(t, 2H), 1.79–1.27(m, 16H), 0.90(t, 3H).

(l)¹H NMR (CDCl₃) δ 7.47(d, 4H), 6.84(d, 4H), 4.12(d, 1H), 3.84(m, 1H), 3.80(s, 6H), 3.33(t, 2H), 3.07(t, 2H), 2.96(t, 2H), 1.8–1.24(m, 16H), 1.08(d, 6H), 0.90(t, 3H).

(m)¹H NMR (CDCl₃) δ 10.15–10.0(bs, 1H), 7.82(m, 1H), 7.53(m, 2H), 7.31(m, 6H), 6.73(m, 1H), 6.61(m, 1H), 3.4(t, 2H), 3.26(t, 2H), 3.00(t, 2H), 1.82–1.49(m, 12H), 1.33(bs, 22H), 0.9(t, 3H).

(n)¹H NMR (CDCl₃) δ 10.8–10.76(bs, 1H), 7.70(m, 1H), 7.15(m, 2H), 7.31(m, 2H), 6.82(m, 4H), 6.73(m, 1H), 6.58(m, 1H), 6.40(bs, 1H), 3.8(s, 6H), 3.46(t, 2H), 3.01(s, 3H), 2.94(t, 2H), 1.78–1.44(m, 6H).

(o)¹H NMR (CDCl₃) δ 7.56–7.33(bs, 4H), 6.67(d, 4H), 4.11(d, 1H), 3.89(m, 1H), 3.3(t, 2H), 3.08(t, 2H), 2.95(bs, 14H), 1.84–1.25(m, 16H), 1.1(d, 6H), 0.9(t, 3H).

(p)¹H NMR (CDCl₃) δ 7.7–6.9(m, 14H), 4.1(t, 1H, J=5.4Hz), 3.8–3.65(m, 2H), 3.1–2.9(m, 4H), 1.9–1.0(m, 18H), 0.85(t, 3H, J=6.7Hz).

(q)¹H NMR (DMSO-d₆) δ 11.58(s, 1H), 5.71(d, 1H), 3.75(m, 1H), 3.07(t, 4H), 2.95–2.78(m, 4H), 1.57–1.1(m, 16H), 1.14(d, 6H), 1.10(d, 6H), 1.03(d, 6H), 0.85(t, 3H).

(r)¹H NMR (CDCl₃) δ 11.68(bs, 1H), 7.67–7.2(m, 9H), 6.68(m, 1H), 6.48(m, 1H), 6.33(m, 1H), 3.46(t, 2H), 3.27(t, 2H), 2.99(t, 2H), 1.83–1.2(m, 16H), 0.90(t, 3H).

(s)¹H NMR (CDCl₃) δ 8.0(s, 1H), 7.85–7.80(m, 2H), 7.55–7.40(m, 7H), 7.3–7.2(m, 2H), 6.9–6.8(m, 2H), 6.4(d, 1H, J=3.3Hz), 3.25(sextet, 4H, J=5.1Hz), 3.15(t, 2H, J=7.2Hz), 1.8–1.2(m, 16H), 0.9–0.8(m, 3H).

(t)¹H NMR (CDCl₃) δ 8.1–8.0(m, 1H), 7.5–7.3(m, 3H), 7.3–7.1(m, 4H), 7.1–7.0(m, 1H), 6.9–6.8(m, 1H), 6.5(d, 1H, J=3.3Hz), 3.3(q, 4H, J=7.4Hz), 3.1(t, 2H, J=7.2Hz), 1.8–1.2(m, 18H), 0.9–0.8(m, 3H).

EXAMPLE 267

Preparation of
N'-(2,4-difluorophenyl)-N-[5-(4,5-diphenyl-1H-imidazol-2-ylthio)pentyl]-N-heptylthiourea Employing the method of Example 1, Part E, using 2,4-difluorophenylisothiocyanate (0.14 g, 0.0008 mol), the title compound (0.19 g, 0.00031 mol) was obtained as a white solid, mp 116°–118°. ¹H NMR (CDCl₃) δ9.5–9.4(s,1H), 7.8–7.1(m,11H), 7.0–6.7(m,3H), 3.8(t,2H,J=7.6Hz), 3.6(t,2H,J=7.8Hz), 3.1(t,2H,J=7Hz), 1.9–1.1(m,18H), 0.9(t,3H,J=4Hz).

EXAMPLE 278

Preparation of
N'-(2,4-difluorophenyl)-N-[5-(4,5-diphenyl-1H-imidazol-2-ylsulfinyl)pentyl]-N-heptylurea To a solution of N'-(2,4-difluorophenyl)-N-[5-(4,5-diphenyl-1H-imidazol-2-ylthio)pentyl]-N-heptylurea (0.59 g, 0.001 mol) in methylene chloride (50 mL) cooled to −78° was added, dropwise, a solution of metachloroperbenzoic acid (0.286 g, 0.0017 mol) in methylene chloride (10 mL). The reaction mixture was stirred at −78° for 1 hour and then allowed to warm to ambient temperature. The reaction mixture was then cooled to 0° and then added, dropwise, was a solution of saturated sodium bisulfite. The layers were separated and the organic layer was washed with saturated sodium bisulfite. The layers were separated and the sodium chloride solution dried over magnesium sulfate and concentrated under vacuum. The residue (0.76 g) was chromatographed with 1:1 hexane-ethyl acetate to give the title compound (0.43 g, 0.00071 mol) as a yellow solid, mp 77°–79°. ¹H NMR (CDCl₃) δ8.1–7.9(m,1H), 7.6–7.2 (m,10H), 6.9–6.7(m,2H), 6.4(d,1H,J=3.3Hz), 3.4–3.1(m,6H), 2.0–1.1(m,18H), 0.9(t,3H,J=6.4Hz).

EXAMPLE 281

Preparation of
N'-(2,4-difluorophenyl)-N-[5-[(4,5-diphenyl-1H-imidazol-2-yl)sulfonyl]pentyl]-N-heptylurea To a solution of N'-(2,4-difluorophenyl)-N-[5-(4,5-diphenyl-1H-imidazol-2-ylthio)pentyl]-N-heptylurea (0.11 g, 0.00019 mol) in methanol (5 mL) was added, portionwise as a solid, Oxone ™ (0.234 g, 0.00038 mol) and the reaction mixture was stirred at ambient temperature for 7 hours. The solids were filtered and washed with methanol. The filtrate was concentrated under vacuum and the residue was chromatographed with 6:4 hexane-ethyl acetate to give the title compound (0.06 g, 0.000096 mol) as a glassy, colorless solid, mp 66°–68°. ¹H NMR (CDCl₃) δ7.85–7.75(m,1H), 7.6–7.1(m,11H), 6.8–6.6(m,2H), 6.4(s,1H), 3.4(t,4H,J=10Hz), 3.25(t,2H,J=7Hz), 1.9–1.75(m,2H), 1.75–1.4(m,6H), 1.4–1.1(m,8H), 0.9(t,3H,J=8Hz).

EXAMPLE 338

Preparation of
N'-(2,4-difluorophenyl)-N-[5-(4,5-diphenyl-1H-imidazol-2-ylamino)pentyl]-N-heptylurea Part A. A solution of 2-bromo-4,5-diphenyl-1H-imidazole (3.5 g, 0.0117 mol) in 1,5-diaminopentane (20 mL) was heated to reflux for 48 hours. The reaction mixture was concentrated in vacuo to give a viscous oil which was taken up in methylene chloride (60 mL) and washed with 10% aqueous NaHCO₃, water (2×50 mL), brine, dried over magnesium sulfate and concentrated in vacuo to give 5-(4,5-diphenyl-1H-imidazol-2-ylamino)aminopentane as a viscous oil (3.5 g, 0.0109 mol). $^1$H NMR (CDCl$_3$) δ7.55-7.09(m,10H), 4.79-3.79(bs,3H), 3.14(t,2H), 2.59(t,2H), 1.79-1.22(m,6H).

Part B. To a solution of 5-(4,5-diphenyl-1H-imidazol-2-ylamino)-aminopentane (1.7 g, 0.00531 mol) and triethylamine (0.58 g, 0.0058 mol) in methylene chloride cooled to 0° under a nitrogen atmosphere, heptanoyl chloride (0.788 g, 0.00531 mol) was added slowly. The reaction mixture was stirred for 1 hour at 0°, poured into water and extracted with methylene chloride (2×50 mL). The combined organic extract was washed with water, brine, dried over magnesium sulfate and concentrated to give N-[5-(4,5-diphenyl-1H-imidazol-2-ylamino)pentyl]heptanamide as a viscous oil. The product was purified by flash chromatography on silica gel (250 mL) eluting methylene chloride:methanol (95:5 v:v), to give an amber foam (1.3 g, 0.003 mol). $^1$H NMR (CDCl$_3$) δ7.43-7.15(m,10H), 6.3(m,1H), 3.24-3.1(m,4H), 2.09(t,2H), 1.6-1.16(m,14H), 0.84(t,3H).

Part C. Employing the method of Example 118, Part B, but using N-[5-(4,5-diphenyl-1H-imidazol-2-ylamino)pentyl]heptanamide, N-[5-(4,5-diphenyl-1H-imidazol-2-ylamino)pentyl]-N-heptylamine was obtained as an amber oil (1.00 g, 0.00238 mol) $^1$H NMR (CDCl$_3$) δ7.56-6.85(m,10H), 3.23(m,2H), 2.49(m,4H), 1.68-0.90(m,16H), 0.88(t,3H).

Part D. Employing the method of Example 118, Part C, but using N-[5-(4,5-diphenyl-1H-imidazol-2-ylamino)pentyl]-N-heptylamine, the title compound was obtained as a yellow foam (0.395 g, 0.000688 mol). $^1$H NMR (CDCl$_3$) δ8.37-7.1(m,11H), 6.9-6.67(m,2H), 6.44(d,1H), 4.53(bs,1H), 3.27(m,6H), 1.74-1.23(m,16H), 0.89(t,3H).

EXAMPLE 339'

Preparation of
N'-(2,4-difluorophenyl)-N-[6-(4,5-diphenyl-1H-imidazol-2-yl)hexyl]-N-heptylurea Part A. To a solution of 4,5-diphenyl-1-[(trimethylsilyl)ethoxymethyl]-1H-imidazole (2.5 g, 0.00734 mol) (B. Lipshutz, B. Huff, W. Hazen, Tetrahedron Letters, 29, 3411-14, 1988), in dry tetrahydrofuran (50 mL) cooled to −78° under a nitrogen atmosphere, n-butyl lithium in hexane (2.5M, 0.00734 mol) was added slowly. The reaction mixture was stirred for 1 hour and 1,6-dibromohexane (2.68 g, 0.0011 mol) was added rapidly, stirred for ½ hour and was allowed to warm to ambient temperature and stirred for 2 additional hours. The reaction mixture was poured into water and extracted with ethyl acetate (2×50 mL). The combined organic layer was washed with water, brine, dried over magnesium sulfate and concentrated to give a viscous oil. The product was purified by flash chromatography on silica gel (250 mL) eluting with hexane:ethyl acetate (70:30 v:v) to give 6-bromo-1-(4,5-diphenyl-1-[(trimethylsilyl)ethoxymethyl]imidazol-2-yl)hexane as an oil (2.18 g, 0.00424 mol). $^1$H NMR (CDCl$_3$) δ7.53-7.16(m,10H), 5.10(s,2H), 3.48(t,2H), 3 34(t,2H), 2.90(t,2H), 1.99-1.5(m,8H), 0.875(t,2H), 0.008(s,9H).

Part B. A solution of 6-bromo-1-(4,5-diphenyl-1-[(trimethylsilyl)ethoxymethyl]-1H-imidazol-2-yl)hexane (1.0 g, 0.00195 mol) and n-heptylamine (0.45 g, 0.00389 mol) in acetonitrile (25 mL) was heated to 60° for 8 hours. The reaction mixture was poured into 10% aqueous sodium bicarbonate and extracted with ethyl acetate (2×50 mL). The combined organic extract was washed with water, brine, dried over magnesium sulfate and concentrated to give N-[6-(4,5-diphenyl-1-[(trimethylsilyl)ethoxymethyl]-1H-imidazol-2-yl)hexyl]-N-heptylamine as a colorless viscous oil (1.04 g, 0.00189 mol). $^1$H NMR (CDCl$_3$) δ7.52-7.2(m,10H), 5.11(s,2H), 4.7-4.2(bs,1H), 3.3(t,2H), 2.93-2.70(m,6H), 1.95-1.34(m,18H), 0.93(t,3H), 0.86(t,2H), 0.005(s,9H).

Part C. Employing the method of Example 118, Part C, but using N-[6-(4,5-diphenyl-1-[(trimethylsilyl)ethoxymethyl]-imidazole-2-yl)hexyl]-N-heptylamine, N'-(2,4-difluorophenyl)-N-[6-(4,5-diphenyl-1-[(trimethylsilyl)ethoxymethyl]-imidazole-2-yl)hexyl]-N-heptylurea was isolated as a viscous oil (1.40 g, 0.00199 mol). $^1$H NMR (CDCl$_3$) δ8.12(m,1H), 7.53-7.16(m,10H), 6.88(m,2H), 6.48(d,1H), 5.1(s,2H), 3.33(m,6H), 2.90(t,2H), 2.0-1.34(m,18H), 0.88(t,3H), 0.79(t,2H), 0.055(s,9H).

Part D. To a solution of N'-(2,4-difluorophenyl)-N-[6-(4,5-diphenyl-1-[(trimethylsilyl)ethoxymethyl]-1H-imidazol-2-yl)hexyl]-N-heptylurea (0.60 g, 0.000853 mol) in dry tetrahydrofuran (10 mL) under a nitrogen atmosphere, tetrabutylammonium fluoride (1M in tetrahydrofuran, 3.41 mL) was added and the reaction mixture was heated to reflux 7 hours. The reaction mixture was cooled, poured into water (50 mL) and extracted with ethyl acetate (2×50 mL). The combined organic layer was washed with water, brine, dried over magnesium sulfate and concentrated in vacuo. The product was purified by flash chromatography on silica gel (75 mL) eluting hexane:ethyl acetate (60:40 v:v) to give the title compound as a colorless glass (0.26 g, 0.000454 mol). $^1$H NMR (CDCl$_3$) δ9.5-9.0(bs,1H), 7.87(m,1H), 7.5-7.2(m,10H), 6.83-6.7(m,2H), 6.4(d,1H), 3.28(m,4H), 2.67(t,2H), 1.75-1.26(m,18H), 0.88(t,3H).

TABLE 2

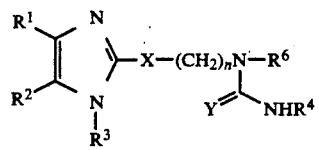

| Ex. No. | R$^1$ | R$^2$ | R$^3$ | R$^4$ | X | Y | n | R$^6$ | mp °C. |
|---|---|---|---|---|---|---|---|---|---|
| 267 | C$_6$H$_5$ | C$_6$H$_5$ | H | 2,4-diFC$_6$H$_3$ | O | O | 5 | (CH$_2$)$_6$CH$_3$ | |
| 268 | C$_6$H$_5$ | C$_6$H$_5$ | H | 2,4-diCH$_3$OC$_6$H$_3$ | O | O | 5 | (CH$_2$)$_6$CH$_3$ | |
| 269 | C$_6$H$_5$ | C$_6$H$_5$ | H | 2,4-diFC$_6$H$_3$ | O | O | 8 | (CH$_2$)$_6$CH$_3$ | |
| 270 | C$_6$H$_5$ | C$_6$H$_5$ | H | n-C$_3$H$_7$ | O | O | 8 | (CH$_2$)$_6$CH$_3$ | |
| 271 | C$_6$H$_5$ | C$_6$H$_5$ | H | 2,4-diFC$_6$H$_3$ | O | S | 5 | (CH$_2$)$_6$CH$_3$ | |
| 272 | C$_6$H$_5$ | C$_6$H$_5$ | CH$_3$ | 2,4-diFC$_6$H$_3$ | O | O | 8 | (CH$_2$)$_6$CH$_3$ | |
| 273 | C$_6$H$_5$ | C$_6$H$_5$ | C$_6$H$_5$ | 2,4,6-triFC$_6$H$_2$ | O | O | 8 | (CH$_2$)$_6$CH$_3$ | |

TABLE 2-continued

Structure: R¹, R² on imidazole ring with N-R³; substituent -X-(CH$_2$)$_n$N(R⁶)-C(=Y)-NHR⁴

| Ex. No. | R¹ | R² | R³ | R⁴ | X | Y | n | R⁶ | mp °C. |
|---|---|---|---|---|---|---|---|---|---|
| 274 | 4-FC$_6$H$_4$ | 4-FC$_6$H$_4$ | H | 2,4,6-triFC$_6$H$_2$ | O | O | 5 | (CH$_2$)$_6$CH$_3$ | |
| 275 | C$_6$H$_5$ | 3-pyridinyl | H | 2,4-diFC$_6$H$_3$ | O | O | 5 | (CH$_2$)$_6$CH$_3$ | |
| 276 | C$_6$H$_5$ | C$_6$H$_5$ | H | 2,4-diFC$_6$H$_3$ | S | S | 5 | (CH$_2$)$_6$CH$_3$ | 116–118 |
| 277 | 4-FC$_6$H$_4$ | 4-FC$_6$H$_4$ | H | 2,4-diFC$_6$H$_3$ | S | S | 8 | (CH$_2$)$_6$CH$_3$ | |
| 278 | C$_6$H$_5$ | C$_6$H$_5$ | H | 2,4-diFC$_6$H$_3$ | SO | O | 5 | (CH$_2$)$_6$CH$_3$ | 77–79 |
| 279 | C$_6$H$_5$ | C$_6$H$_5$ | H | 2,4-diFC$_6$H$_3$ | SO | O | 8 | (CH$_2$)$_6$CH$_3$ | |
| 280 | C$_6$H$_5$ | C$_6$H$_5$ | H | n-C$_3$H$_7$ | SO | O | 5 | (CH$_2$)$_6$CH$_3$ | |
| 281 | C$_6$H$_5$ | C$_6$H$_5$ | H | 2,4-diFC$_6$H$_3$ | SO$_2$ | O | 5 | (CH$_2$)$_6$CH$_3$ | 66–68 |
| 282 | C$_6$H$_5$ | C$_6$H$_5$ | H | 2,4-diFC$_6$H$_3$ | SO$_2$ | O | 8 | (CH$_2$)$_6$CH$_3$ | |
| 283 | C$_6$H$_5$ | C$_6$H$_5$ | H | n-C$_3$H$_7$ | SO$_2$ | O | 8 | (CH$_2$)$_6$CH$_3$ | |
| 284 | C$_6$H$_5$ | C$_6$H$_5$ | H | n-C$_3$H$_7$ | SO$_2$ | S | 5 | (CH$_2$)$_6$CH$_3$ | |
| 285 | C$_6$H$_5$ | C$_6$H$_5$ | CH$_3$ | n-C$_3$H$_7$ | SO$_2$ | O | 5 | (CH$_2$)$_6$CH$_3$ | |
| 286 | C$_6$H$_5$ | C$_6$H$_5$ | H | 2,4,6-triFC$_6$H$_2$ | NH | O | 5 | (CH$_2$)$_6$CH$_3$ | |
| 287 | C$_6$H$_5$ | C$_6$H$_5$ | H | 2,4-diCH$_3$OC$_6$H$_3$ | NH | O | 5 | (CH$_2$)$_6$CH$_3$ | |
| 288 | C$_6$H$_5$ | C$_6$H$_5$ | H | 2,4-diFC$_6$H$_3$ | NH | O | 8 | (CH$_2$)$_6$CH$_3$ | |
| 289 | 4-FC$_6$H$_4$ | 4-FC$_6$H$_4$ | H | n-C$_5$H$_{11}$ | NH | O | 4 | (CH$_2$)$_8$CH$_3$ | |
| 290 | C$_6$H$_5$ | C$_6$H$_5$ | CH$_3$ | C$_6$H$_5$ | NH | O | 7 | (CH$_2$)$_5$CH$_3$ | |
| 291 | C$_6$H$_5$ | C$_6$H$_5$ | H | 2,4-diFC$_6$H$_3$ | NCH$_3$ | O | 5 | (CH$_2$)$_6$CH$_3$ | |
| 292 | C$_6$H$_5$ | C$_6$H$_5$ | H | 2,4-diFC$_6$H$_3$ | NCH$_3$ | O | 8 | (CH$_2$)$_6$CH$_3$ | |
| 293 | C$_6$H$_5$ | C$_6$H$_5$ | H | n-C$_3$H$_7$ | NCH$_2$C$_6$H$_5$ | O | 6 | (CH$_2$)$_8$CH$_3$ | |
| 294 | C$_6$H$_5$ | C$_6$H$_5$ | H | 2,4,6-triFC$_6$H$_2$ | NCH$_2$C$_6$H$_5$ | O | 5 | (CH$_2$)$_6$CH$_3$ | |
| 295 | C$_6$H$_5$ | C$_6$H$_5$ | H | 2,4-diClC$_6$H$_3$ | NC$_3$H$_7$ | O | 8 | (CH$_2$)$_6$CH$_3$ | |
| 296 | C$_6$H$_5$ | C$_6$H$_5$ | H | 3,4,5-triCH$_3$OC$_6$H$_2$ | NC$_3$H$_7$ | O | 4 | (CH$_2$)$_5$CH$_3$ | |
| 297 | C$_6$H$_5$ | C$_6$H$_5$ | H | CH$_3$ | NC$_6$H$_{13}$ | O | 5 | (CH$_2$)$_6$CH$_3$ | |
| 298 | C$_6$H$_5$ | C$_6$H$_5$ | H | 2,4,6-triFC$_6$H$_2$ | S | S | 5 | (CH$_2$)$_6$CH$_3$ | 124–126 |
| 299 | C$_6$H$_5$ | C$_6$H$_5$ | H | (CH$_2$)$_2$CH$_3$ | S | S | 5 | (CH$_2$)$_6$CH$_3$ | 89–91 |
| 300 | C$_6$H$_5$ | C$_6$H$_5$ | H | 3-FC$_6$H$_4$ | S | S | 5 | (CH$_2$)$_6$CH$_3$ | 161–163 |
| 301 | (CH$_3$)$_2$CH | (CH$_3$)$_2$CH | H | C$_6$H$_{11}$ | NH | O | 5 | (CH$_2$)$_6$CH$_3$ | |
| 302 | (CH$_3$)$_2$CH | C$_6$H$_5$ | H | 2,4-diCH$_3$OC$_6$H$_3$ | CH$_2$ | O | 5 | (CH$_2$)$_6$CH$_3$ | |
| 303 | 4-CH$_3$OC$_6$H$_4$ | C$_6$H$_5$ | H | 2,4,6-triFC$_6$H$_2$ | SO | O | 5 | (CH$_2$)$_6$CH$_3$ | |
| 304 | 4-CH$_3$OC$_6$H$_4$ | 4-CH$_3$OC$_6$H$_4$ | H | 3-FC$_6$H$_4$ | SO$_2$ | O | 5 | (CH$_2$)$_6$CH$_3$ | |
| 305 | 4-CH$_3$OC$_6$H$_4$ | 4-CH$_3$OC$_6$H$_4$ | H | CH(CH$_3$)$_2$ | O | S | 5 | (CH$_2$)$_6$CH$_3$ | |
| 306 | 4-CH$_3$OC$_6$H$_4$ | 4-CH$_3$OC$_6$H$_4$ | H | C$_6$H$_5$ | NH | S | 5 | (CH$_2$)$_6$CH$_3$ | |
| 307 | 4-CH$_3$OC$_6$H$_4$ | 4-CH$_3$OC$_6$H$_4$ | H | (CH$_2$)$_7$CH$_3$ | CH$_2$ | S | 5 | (CH$_2$)$_6$CH$_3$ | |
| 308 | 4-CH$_3$OC$_6$H$_4$ | 4-CH$_3$OC$_6$H$_4$ | H | 2,6-diClC$_6$H$_3$ | O | O | 5 | (CH$_2$)$_6$CH$_3$ | |
| 309 | 4-CH$_3$OC$_6$H$_4$ | 4-CH$_3$OC$_6$H$_4$ | H | CH$_3$ | NH | O | 5 | (CH$_2$)$_6$CH$_3$ | |
| 310 | 4-CH$_3$OC$_6$H$_4$ | 4-CH$_3$OC$_6$H$_4$ | H | (C$_6$H$_4$)(C$_6$H$_5$) | CH$_2$ | O | 5 | (CH$_2$)$_6$CH$_3$ | |
| 311 | 4-CH$_3$OC$_6$H$_4$ | 4-CH$_3$OC$_6$H$_4$ | CH$_3$ | 2,4-diFC$_6$H$_3$ | SO | O | 5 | (CH$_2$)$_6$CH$_3$ | |
| 312 | (CH$_3$)$_2$CH | (CH$_3$)$_2$CH | CH$_3$ | C$_6$H$_{11}$ | SO$_2$ | O | 5 | (CH$_2$)$_6$CH$_3$ | |
| 313 | (CH$_3$)$_2$CH | (CH$_3$)$_2$CH | CH$_3$ | C$_6$H$_5$ | O | H$_2$ | 5 | (CH$_2$)$_6$CH$_3$ | |
| 314 | C$_6$H$_5$ | C$_6$H$_5$ | H | 2,4-diFC$_6$H$_3$ | NH | H$_2$ | 3 | (CH$_2$)$_6$CH$_3$ | |
| 315 | 4-CH$_3$OC$_6$H$_4$ | 4-CH$_3$OC$_6$H$_4$ | H | C$_6$H$_{11}$ | CH$_2$ | H$_2$ | 3 | (CH$_2$)$_6$CH$_3$ | |
| 316 | C$_6$H$_5$ | C$_6$H$_5$ | H | n-C$_3$H$_7$ | O | S | 5 | (CH$_2$)$_6$CH$_3$ | |
| 317 | (CH$_3$)$_2$CH | (CH$_3$)$_2$CH | H | C$_6$H$_{11}$ | NH | S | 5 | (CH$_2$)$_6$CH$_3$ | |
| 318 | (CH$_3$)$_2$CH | C$_6$H$_5$ | H | CH(CH$_3$)$_2$ | CH$_2$ | S | 5 | (CH$_2$)$_6$CH$_3$ | |
| 319 | C$_6$H$_5$ | 4-CH$_3$OC$_6$H$_4$ | H | C$_6$H$_5$ | O | H$_2$ | 5 | (CH$_2$)$_6$CH$_3$ | |
| 320 | (CH$_3$)$_2$CH | (CH$_3$)$_2$CH | H | 2,4-diFC$_6$H$_3$ | NH | H$_2$ | 3 | (CH$_2$)$_6$CH$_3$ | |
| 321 | 4-(CH$_3$)$_2$NC$_6$H$_4$ | 4-(CH$_3$)$_2$NC$_6$H$_4$ | H | C$_6$H$_{11}$ | CH$_2$ | H$_2$ | 8 | (CH$_2$)$_6$CH$_3$ | |
| 322 | 4-(CH$_3$)$_2$NC$_6$H$_4$ | 4-(CH$_3$)$_2$NC$_6$H$_4$ | H | (CH$_2$)$_7$CH$_3$ | SO | O | 5 | C$_6$H$_5$ | |
| 323 | 4-(CH$_3$)$_2$NC$_6$H$_4$ | 4-(CH$_3$)$_2$NC$_6$H$_4$ | H | n-C$_3$H$_7$ | SO$_2$ | O | 5 | (CH$_2$)$_6$CH$_3$ | |
| 324 | 4-(CH$_3$)$_2$NC$_6$H$_4$ | 4-(CH$_3$)$_2$NC$_6$H$_4$ | H | C$_6$H$_{11}$ | NH | O | 5 | (CH$_2$)$_6$CH$_3$ | |
| 325 | 4-(CH$_3$)$_2$NC$_6$H$_4$ | 4-(CH$_3$)$_2$NC$_6$H$_4$ | H | CH(CH$_3$)$_2$ | CH$_2$ | O | 5 | (CH$_2$)$_6$CH$_3$ | |
| 326 | 4-(CH$_3$)$_2$NC$_6$H$_4$ | 4-(CH$_3$)$_2$NC$_6$H$_4$ | H | C$_6$H$_5$ | CH$_2$ | S | 5 | (CH$_2$)$_6$CH$_3$ | |
| 327 | 4-(CH$_3$)$_2$NC$_6$H$_4$ | 4-(CH$_3$)$_2$NC$_6$H$_4$ | H | 2,4-diFC$_6$H$_3$ | S | H$_2$ | 3 | (CH$_2$)$_6$CH$_3$ | |
| 328 | 4-CH$_3$OC$_6$H$_4$ | 4-CH$_3$OC$_6$H$_4$ | H | C$_6$H$_{11}$ | S | H$_2$ | 8 | (CH$_2$)$_6$CH$_3$ | |
| 329 | C$_6$H$_5$ | C$_6$H$_5$ | C$_6$H$_5$ | (CH$_2$)$_7$CH$_3$ | S | H$_2$ | 5 | C$_6$H$_5$ | |
| 330 | C$_6$H$_5$ | C$_6$H$_5$ | CH$_2$CH$_3$ | 2,4-diFC$_6$H$_3$ | S | H$_2$ | 5 | (CH$_2$)$_6$CH$_3$ | |
| 331 | (CH$_3$)$_2$CH | (CH$_3$)$_2$CH | CH$_2$C$_6$H$_5$ | 2,4-diFC$_6$H$_3$ | S | H$_2$ | 5 | (CH$_2$)$_6$CH$_3$ | |
| 332 | 4-CH$_3$SC$_6$H$_4$ | 4-CH$_3$SC$_6$H$_4$ | H | 2,4-diFC$_6$H$_3$ | S | O | 8 | (CH$_2$)$_6$CH$_3$ | |
| 333 | 4-CH$_3$SOC$_6$H$_4$ | 4-CH$_3$SOC$_6$H$_4$ | H | C$_6$H$_{11}$ | O | H$_2$ | 8 | (CH$_2$)$_6$CH$_3$ | |
| 334 | 4-CH$_3$SO$_2$C$_6$H$_4$ | 4-CH$_3$SO$_2$C$_6$H$_4$ | H | 2,4-diFC$_6$H$_3$ | CH$_2$ | S | 5 | (CH$_2$)$_3$CH$_3$ | |
| 335 | 4-CH$_3$SC$_6$H$_4$ | C$_6$H$_5$ | H | 2,4-diFC$_6$H$_3$ | NH | O | 5 | (CH$_2$)$_8$CH$_3$ | |
| 336 | 4-CH$_3$SOC$_6$H$_4$ | C$_6$H$_5$ | H | 2,4-diFC$_6$H$_3$ | S | H$_2$ | 5 | CH$_3$ | |
| 337 | 4-CH$_3$SO$_2$C$_6$H$_4$ | C$_6$H$_5$ | H | 2,4-diFC$_6$H$_3$ | S | S | 5 | C$_6$H$_5$ | |
| 338 | C$_6$H$_5$ | C$_6$H$_5$ | H | 2,4-diFC$_6$H$_3$ | NH | O | 5 | (CH$_2$)$_6$CH$_3$ | foam |
| 339 | C$_6$H$_5$ | C$_6$H$_5$ | H | 2,4-diFC$_6$H$_3$ | CH$_2$ | O | 5 | (CH$_2$)$_6$CH$_3$ | glass |

EXAMPLE 340

Preparation of
2,4-difluoro-N-[(5-(4,5-diphenyl-1H-imidazol-2-ylthio)-pentyl)]-N-heptylbenzeneacetamide To a solution of N-[5-(4,5-diphenyl-1H-imidazol-2-ylthio)pentyl]-1-heptanamine (2.2 g, 0.005 mol), 1-hydroxybenzotriazole hydrate (0.81 g, 0.006 mol), and 2,4-difluorophenylacetic acid (1.12 g, 0.0065 mol) in N,N-dimethylformamide (50 mL) at 0° was added, portionwise as a solid, dicyclohexylcarbodiimide (1.24 g, 0.006 mol). The reaction mixture was stirred at 0° for 2.5 hours, then at ambient temperature for 72 hours. The solids were filtered and washed with chloroform. The filtrate was concentrated under vacuum and the residue (5.2 g) was chromatographed with 7:3 hexane-ethyl acetate. The resulting solid was triturated with hexane to give the title compound (2.59 g, 0.0044 mol) as a yellow oil. $^1$H NMR (CDCl$_3$) $\delta$7.6–7.0(m,11H), 6.8–6.5(m,2H), 3.7(d,2H,J=13.7Hz), 3.5(t,2H,J=6.4Hz), 3.4–3.0(m,3H), 2.9(t,2H,J=6.1Hz), 1.8–1.1(m,17H), 0.9(t,3H,J=6.6Hz).

EXAMPLE 353

Preparation of
N-[5-[4,5-bis(4-methoxyphenyl)-1H-imidazol-2-ylthio]-pentyl]-2,4-difluoro-N-heptylbenzeneethaneamine To a solution of lithium aluminium hydride (1N in tetrahydrofuran, 2 mL) in dry tetrahydrofuran (30 mL), a solution of N-[5-[4,5-bis(4-methoxyphenyl)-1H-imidazol-2-ylthio]pentyl]-2,4-difluoro-N-heptylbenzeneacetamide (0.70 g, 0.00107 mol) in dry tetrahydrofuran (15 mL) was added slowly. The reaction mixture was heated to reflux for 5 hours and was then allowed to cool to ambient temperature. The reaction mixture was poured into a mixture of 10% aqueous sodium sulfate (150 mL) and ice (150 mL). The resultant emulsion was filtered through Celite ® and the filtrate was extracted with ethyl acetate (3×100 mL). The organic layer was washed with water, brine, dried over magnesium sulfate and concentrated in vacuo to give a crude oil. The product was purified by flash chromatography on silica gel (100 mL) eluting methanol: methylene chloride (5:95 v:v) to give the title compound as a viscous colorless oil (0.46 g, 0.000723 mol). $^1$H NMR (CDCl$_3$) $\delta$9.2–9.15(bs,1H), 7.56–7.25(m,4H), 7.11(m,1H), 6.94–6.70(m,6H), 3.81(m,6H), 3.07(t,2H), 2.74–2.58(m,4H), 2.43(m,4H), 1.71(m,2H), 1.53–1.20(m,14H), 0.91(t,3H).

EXAMPLE 355

Preparation of
N-[5-[4,5-bis(4-methoxyphenyl)-1H-imidazol-2-ylthio]-pentyl]-N-heptylcyclohexaneacetamide Part A. Employing the method of Example 118, Part C, but using 2-cyclohexane acetyl chloride, N-heptyl-N-(5-hydroxypentyl)-cyclohexaneacetamide was obtained as an oil (1.5 g, 0.0046 mol). $^1$H NMR (CDCl$_3$) $\delta$3.70–3.61(m,2H), 3.37–3.18(m,4H), 2.03(d,2H), 1.97–1.08(m,26H), 1.02–0.86(m,4H).

Part B. Employing the method of Example 118, Part D, but using N-heptyl-N-(5-hydroxypentyl)cyclohexaneacetamide, N-(5-bromopentyl)-N-heptylcyclohexane acetamide was isolated as an oil (1.3 g, 0.00334 mol). $^1$H NMR (CDCl$_3$) $\delta$3.47–3.39(m,2H), 3.36–3.18(m,4H), 2.17(d,2H), 1.96–0.86(m,30H).

Part C. Employing the method of Example 118, Part E, but using N-(5-bromopentyl)-N-heptylcyclohexaneacetamide, the title compound was isolated as an oil (0.47 g, 0.00075 mol). $^1$H NMR (DMSO-d$_6$) $\delta$12.34(s,1H), 7.29(d,2H), 6.95(d,2H), 6.84(d,2H), 3.77(s,3H), 3.73(s,3H), 3.18(m,4H) 3.07(m,2H), 2.09(d,2H), 1.73–0.81(m,30H).

Additional amides, which are listed in Table 3, were prepared or could be prepared analogously according to the procedures of Examples 340, 353 and 355.

TABLE 3

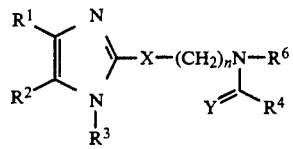

| Ex. No. | R$^1$ | R$^2$ | R$^3$ | R$^4$ | X | Y | n | R$^6$ | mp °C. |
|---|---|---|---|---|---|---|---|---|---|
| 340 | C$_6$H$_5$ | C$_6$H$_5$ | H | CH$_2$-2,4-diFC$_6$H$_3$ | S | O | 5 | (CH$_2$)$_6$CH$_3$ | oil |
| 341 | C$_6$H$_5$ | C$_6$H$_5$ | H | CH$_2$CH$_2$CH$_3$ | S | O | 5 | (CH$_2$)$_6$CH$_3$ | oil$^{(a)}$ |
| 342 | C$_6$H$_5$ | C$_6$H$_5$ | H | CH$_2$(CH$_2$)$_2$CH$_3$ | S | O | 5 | (CH$_2$)$_6$CH$_3$ | oil$^{(b)}$ |
| 343 | C$_6$H$_5$ | C$_6$H$_5$ | H | CH$_2$(C$_6$H$_4$)(C$_6$H$_5$) | S | O | 5 | (CH$_2$)$_6$CH$_3$ | 57–58 |
| 344 | C$_6$H$_5$ | C$_6$H$_5$ | H | CH$_2$C$_6$H$_{11}$ | S | O | 5 | (CH$_2$)$_6$CH$_3$ | oil$^{(c)}$ |
| 345 | C$_6$H$_5$ | C$_6$H$_5$ | H | 2,4-diFC$_6$H$_3$ | S | O | 5 | (CH$_2$)$_6$CH$_3$ | oil$^{(d)}$ |
| 346 | C$_6$H$_5$ | C$_6$H$_5$ | H | C$_6$H$_5$ | S | O | 5 | (CH$_2$)$_6$CH$_3$ | oil$^{(e)}$ |
| 347 | (CH$_3$)$_2$CH | (CH$_3$)$_2$CH | H | CH$_2$—C$_6$H$_{11}$ | S | O | 5 | (CH$_2$)$_6$CH$_3$ | oil$^{(f)}$ |
| 348 | 4-CH$_3$OC$_6$H$_4$ | 4-CH$_3$OC$_6$H$_4$ | H | (CH$_2$)$_2$CH$_3$ | S | O | 5 | (CH$_2$)$_6$CH$_3$ | oil$^{(g)}$ |
| 349 | 4-CH$_3$OC$_6$H$_4$ | 4-CH$_3$OC$_6$H$_4$ | H | CH$_2$-3,4-diClC$_6$H$_3$ | S | O | 5 | (CH$_2$)$_6$CH$_3$ | oil$^{(h)}$ |
| 350 | 4-CH$_3$OC$_6$H$_4$ | 4-CH$_3$OC$_6$H$_4$ | H | CH$_2$—C$_6$F$_5$ | S | O | 5 | (CH$_2$)$_6$CH$_3$ | oil$^{(i)}$ |
| 351 | 4-CH$_3$OC$_6$H$_4$ | 4-CH$_3$OC$_6$H$_4$ | H | CH$_2$-2,4-diFC$_6$H$_3$ | S | O | 5 | (CH$_2$)$_6$CH$_3$ | oil$^{(j)}$ |
| 352 | C$_6$H$_5$ | C$_6$H$_5$ | H | (CH$_2$)$_2$CH$_3$ | S | H$_2$ | 5 | (CH$_2$)$_6$CH$_3$ | oil$^{(k)}$ |
| 353 | 4-CH$_3$OC$_6$H$_4$ | 4-CH$_3$OC$_6$H$_4$ | H | CH$_2$-2,4-diFC$_6$H$_3$ | S | H$_2$ | 5 | (CH$_2$)$_6$CH$_3$ | oil |
| 354 | 4-(CH$_3$)$_2$NC$_6$H$_4$ | 4-(CH$_3$)$_2$NC$_6$H$_4$ | H | CH$_2$C$_6$H$_{11}$ | S | O | 5 | (CH$_2$)$_6$CH$_3$ | oil$^{(l)}$ |
| 355 | 4-CH$_3$OC$_6$H$_4$ | 4-CH$_3$OC$_6$H$_4$ | H | CH$_2$C$_6$H$_{11}$ | S | O | 5 | (CH$_2$)$_6$CH$_3$ | oil |
| 356 | n-C$_3$H$_7$ | n-C$_3$H$_7$ | H | n-C$_3$H$_7$ | S | O | 5 | (CH$_2$)$_6$CH$_3$ | |
| 357 | 3-pyridinyl | 3-pyridinyl | H | CH$_2$-2,4-diCH$_3$OC$_6$H$_3$ | CH$_2$ | O | 5 | (CH$_2$)$_6$CH$_3$ | |
| 358 | 4-pyridinyl | 4-pyridinyl | H | CH$_2$-2,4,6-triFC$_6$H$_2$ | NH | O | 5 | (CH$_2$)$_6$CH$_3$ | |
| 359 | 2-CH$_3$OC$_6$H$_4$ | 2-CH$_3$OC$_6$H$_4$ | H | CH$_2$-3-FC$_6$H$_4$ | S | H$_2$ | 5 | (CH$_2$)$_6$CH$_3$ | |
| 360 | 3-CH$_3$OC$_6$H$_4$ | 3-CH$_3$OC$_6$H$_4$ | H | CH(CH$_3$)$_2$ | O | O | 5 | (CH$_2$)$_6$CH$_3$ | |
| 361 | C$_6$H$_{11}$ | C$_6$H$_{11}$ | H | C$_6$H$_5$ | CH$_2$ | O | 5 | (CH$_2$)$_6$CH$_3$ | |
| 362 | C$_6$H$_5$ | 4-(CH$_3$)$_2$NC$_6$H$_4$ | H | (CH$_2$)$_7$CH$_3$ | NH | O | 5 | (CH$_2$)$_6$CH$_3$ | |
| 363 | 2-furanyl | 2-furanyl | H | 2,6-diClC$_6$H$_3$ | S | O | 5 | (CH$_2$)$_6$CH$_3$ | |

TABLE 3-continued $$R^1, R^2 \text{ imidazole with } N-R^3, \text{ substituent } -X-(CH_2)_n-N(R^6)-C(=Y)R^4$$

| Ex. No. | R¹ | R² | R³ | R⁴ | X | Y | n | R⁶ | mp °C. |
|---|---|---|---|---|---|---|---|---|---|
| 364 | 4-(t-$C_4H_9$)$C_6H_4$ | 4-(t-$C_4H_9$)$C_6H_4$ | H | $CH_3$ | O | $H_2$ | 5 | $(CH_2)_6CH_3$ | |
| 365 | 2-thienyl | 2-thienyl | H | $CH_2(C_6H_4)(C_6H_5)$ | $CH_2$ | O | 5 | $(CH_2)_6CH_3$ | |
| 366 | 4-HO$C_6H_4$ | 4-HO$C_6H_4$ | $CH_3$ | 2,4-diF$C_6H_3$ | NH | O | 5 | $(CH_2)_6CH_3$ | |
| 367 | $(CH_3)_2$CH | $(CH_3)_2$CH | $CH_3$ | $C_6H_{11}$ | S | O | 5 | $(CH_2)_6CH_3$ | |
| 368 | $C_6H_5CH_2$ | $C_6H_5CH_2$ | $CH_3$ | $C_6H_5$ | O | O | 5 | $(CH_2)_6CH_3$ | |
| 369 | $C_6H_4$-2-OCH$_2$O-2'-$C_6H_4$ | | H | 2,4-diF$C_6H_3$ | $CH_2$ | $H_2$ | 3 | $(CH_2)_6CH_3$ | |
| 370 | 4-$CH_3C_6H_4$ | 4-$CH_3C_6H_4$ | H | 2,4-diF$C_6H_3$ | S | O | 8 | $(CH_2)_6CH_3$ | |
| 371 | 4-$CH_3OC_6H_4$ | 4-$(CH_3)_2NC_6H_4$ | H | $C_6H_{11}$ | O | O | 8 | $(CH_2)_6CH_3$ | |
| 372 | 4-$CH_3OC_6H_4$ | $C_6H_{11}$ | H | $CH_2$-2,4-diF$C_6H_3$ | $CH_2$ | O | 5 | $(CH_2)_3CH_3$ | |
| 373 | 4-$CH_3OC_6H_4$ | $(CH_3)_2$CH | H | $CH_2$-2,4-diF$C_6H_3$ | NH | $H_2$ | 5 | $(CH_2)_8CH_3$ | |
| 374 | 4-$(CH_3)_2NC_6H_4$ | $C_6H_{11}$ | H | 2,4-diF$C_6H_3$ | S | O | 5 | $CH_3$ | |
| 375 | 4-$(CH_3)_2NC_6H_4$ | $(CH_3)_2$CH | H | $CH_2$-2,4-diF$C_6H_3$ | O | O | 5 | $C_6H_5$ | |
| 376 | $C_6H_4OC_6H_4$ | | | $C_6H_{11}$ | NH | O | 3 | $(CH_2)_6CH_3$ | |
| 377 | $C_6H_5$ | 4-$CH_3OC_6H_4$ | $CH_2C_6H_5$ | $(CH_2)_7CH_3$ | NH | O | 5 | $(CH_2)_3CH_3$ | |
| 378 | $C_6H_5$ | 4-$(CH_3)_2NC_6H_4$ | $C_6H_5$ | $(CH_2)_7CH_3$ | S | $H_2$ | 5 | $C_6H_5$ | |
| 379 | $(CH_3)_2$CH | $(CH_3)_2$CH | H | 2,4-diF$C_6H_3$ | S | O | 5 | $(CH_2)_6CH_3$ | |
| 380 | 4-$CH_3SC_6H_4$ | 4-$CH_3SC_6H_4$ | H | $CH_2$-2,4-diF$C_6H_3$ | S | O | 5 | $(CH_2)_6CH_3$ | |
| 381 | 4-$CH_3SOC_6H_4$ | 4-$CH_3SOC_6H_4$ | H | $CH_2$-2,4-diF$C_6H_3$ | NH | O | 5 | $(CH_2)_6CH_3$ | |
| 382 | 4-$CH_3SO_2C_6H_4$ | 4-$CH_3SO_2C_6H_4$ | H | $CH_2$-2,4-diF$C_6H_3$ | $CH_2$ | O | 5 | $(CH_2)_6CH_3$ | |
| 383 | $C_6H_5$ | 4-$CH_3SC_6H_4$ | H | $CH_2$-2,4-diF$C_6H_3$ | S | O | 5 | $(CH_2)_6CH_3$ | |
| 384 | $C_6H_5$ | 4-$CH_3SOC_6H_4$ | H | $CH_2$-2,4-diF$C_6H_3$ | NH | O | 5 | $(CH_2)_6CH_3$ | |
| 385 | $C_6H_5$ | 4-$CH_3SO_2C_6H_4$ | H | $CH_2$-2,4-diF$C_6H_3$ | $CH_2$ | O | 5 | $(CH_2)_6CH_3$ | |
| 386 | 4-$CH_3OC_6H_4$ | 4-$CH_3OC_6H_4$ | $CH_3$ | n-$C_3H_7$ | S | O | 5 | $(CH_2)_6CH_3$ | |
| 387 | 4-$CH_3OC_6H_4$ | 4-$CH_3OC_6H_4$ | H | $CH_2C_6H_{11}$ | SO | O | 5 | $(CH_2)_6CH_3$ | |
| 388 | 4-$CH_3OC_6H_4$ | 4-$CH_3OC_6H_4$ | H | $CH(CH_3)_2$ | S | O | 5 | $(CH_2)_6CH_3$ | |
| 389 | 4-$CH_3OC_6H_4$ | 4-$CH_3OC_6H_4$ | H | $CH_2C_6H_5$ | S | O | 5 | $(CH_2)_6CH_3$ | |
| 390 | 4-$CH_3OC_6H_4$ | 4-$CH_3OC_6H_4$ | H | $CH_2$-2,4-diF$C_6H_3$ | S | S | 3 | $(CH_2)_6CH_3$ | |
| 391 | 4-$CH_3OC_6H_4$ | 4-$CH_3OC_6H_4$ | H | $CH_2C_6H_{11}$ | S | O | 8 | $(CH_2)_6CH_3$ | |
| 392 | 4-$CH_3OC_6H_4$ | 4-$CH_3OC_6H_4$ | H | $(CH_2)_7CH_3$ | S | O | 5 | $C_6H_5$ | |
| 393 | 4-$(CH_3)_2NC_6H_4$ | 4-$(CH_3)_2NC_6H_4$ | H | n-$C_3H_7$ | $SO_2$ | O | 5 | $(CH_2)_6CH_3$ | |
| 394 | 4-$(CH_3)_2NC_6H_4$ | 4-$(CH_3)_2NC_6H_4$ | H | $C_6H_{11}$ | S | O | 5 | $(CH_2)_6CH_3$ | |
| 395 | 4-$(CH_3)_2NC_6H_4$ | 4-$(CH_3)_2NC_6H_4$ | H | $CH(CH_3)_2$ | S | $H_2$ | 5 | $(CH_2)_6CH_3$ | |
| 396 | 4-$(CH_3)_2NC_6H_4$ | 4-$(CH_3)_2NC_6H_4$ | H | $C_6H_5$ | S | O | 5 | $(CH_2)_6CH_3$ | |
| 397 | 4-$(CH_3)_2NC_6H_4$ | 4-$(CH_3)_2NC_6H_4$ | H | 2,4-diF$C_6H_3$ | SO | O | 3 | $(CH_2)_6CH_3$ | |
| 398 | 4-$(CH_3)_2C_6H_4$ | 4-$(CH_3)_2NC_6H_4$ | H | $C_6H_{11}$ | S | O | 8 | $(CH_2)_6CH_3$ | |
| 399 | 4-$(CH_3)_2NC_6H_4$ | 4-$(CH_3)_2NC_6H_4$ | H | $(CH_2)_7CH_3$ | $SO_2$ | O | 5 | $C_6H_5$ | |
| 400 | $C_6H_5$ | $C_6H_5$ | H | $CH(CH_3)_2$ | S | O | 5 | $(CH_2)_6CH_3$ | oil$^{(m)}$ |

Footnotes To Table 3
(a) ¹H NMR (CDCl₃) δ 11.7–11.6(bs, 1H), 7.7–7.1(m, 10H), 3.4(t, 2H, J=7Hz), 3.3–3.2(m, 2H), 2.9(t, 2H, J=7Hz), 2.35–2.25(m, 2H), 1.8–1.1(m, 18H), 1.0–0.8(m, 6H).
(b) ¹H NMR (CDCl₃) δ 11.8–11.7(bs, 1H), 7.7–7.1(m, 10H), 3.4(t, 2H, J=6.6Hz), 3.2(t, 2H, J=8.7), 2.9(t, 2H, J=6.5Hz), 2.4–2.2(m, 2H), 1.8–1.1(m, 20H), 0.85(sextet, 6H, J=4.1Hz).
(c) ¹H NMR (CDCl₃) δ 7.6–7.1(m, 11H), 3.4–2.9(m, 6H), 2.2–2.1(m, 2H), 1.8–1.0(m, 27H), 0.9–0.8(m, 3H).
(d) ¹H NMR (CDCl₃) δ 7.6–7.2(m, 11H), 6.9–6.8(m, 2H), 3.7–3.4(m, 2H), 3.2–3.0(m, 4H), 1.9–1.0(m, 17H).
(e) ¹H NMR (CDCl₃) δ 7.6–7.1(m, 16H), 3.6–3.4(m, 2H), 3.3–2.9(m, 4H), 1.9–1.0(m, 16H), 0.9–0.8(m, 3H).
(f) ¹H NMR (DMSO-d₆) δ 11.64(bs, 1H), 3.18(m, 4H), 2.98–2.74(m, 4H), 2.08(d, 2H), 1.77–0.81(m, 42H).
(g) ¹H NMR (DMSO-d₆) δ 12.36(s, 1H), 7.39(d, 2H), 7.31(d, 2H), 6.95(d, 2H), 6.85(d, 2H), 3.76(s, 3H), 3.74(s, 3H), 3.28–3.03(m, 6H), 2.22(t, 2H), 1.75–1.11(m, 18H), 0.83(m, 6H).
(h) ¹H NMR (DMSO-d₆) δ 12.35(bs, 1H), 7.62–7.17(m, 7H), 6.95(d, 2H), 6.85(d, 2H), 3.8–3.66(m, 8H), 3.35–3.02(m, 6H), 1.78–1.14(m, 16H), 0.85(m, 3H).
(i) ¹H NMR (DMSO-d₆) δ 12.33(bs, 1H), 7.37(d, 2H), 7.31(d, 2H), 6.94(d, 2H), 6.83(d, 2H), 3.82(d, 2H), 3.77(s, 3H), 3.73(s, 3H), 3.42–3.01(m, 6H), 1.81–1.16(m, 16H), 0.85(m, 3H).
(j) ¹H NMR (DMSO-d₆) δ 12.32(bs, 1H), 7.43–6.8(m, 11H), 3.78(s, 3H), 3.73(s, 3H), 3.65(s, 2H), 3.35–3.01(m, 6H), 1.77–1.16(m, 16H), 0.87(m, 3H).
(k) ¹H NMR (CDCl₃) δ 7.6–7.2(m, 10H), 2.1(t, 2H, J=7.4Hz), 2.5–2.3(m, 7H), 1.8–1.6(m, 2H), 1.5–1.2(m, 18H), 0.9(quintet, 6H, J=5.1Hz).
(l) ¹H NMR (DMSO-d₆) δ 12.12(s, 1H), 7.31(d, 2H), 7.20(d, 2H), 6.70(d, 2H), 6.63(d, 2H), 3.18(m, 4H), 3.03(m, 2H), 2.91(s, 6H), 2.87(s, 6H), 2.08(d, 2H), 1.64–0.82(m, 30H).
(m) ¹H NMR (CDCl₃) δ 11.8(s, 1H), 7.7–7.2(m, 1H), 3.5(t, 2H, J=6.4Hz), 3.3–3.1(m, 3H), 2.95(t, 2H, J=6.1Hz), 2.85–2.7(m, 1H), 1.9–1.2(m, 14H), 1.1–1.0(m, 6H), 0.9–0.8(m, 3H).

EXAMPLE 401

Preparation of cyclohexyl [5-(4,5-diphenyl-1H-imidazol-2-ylthio)pentyl]heptylcarbamate To a solution of N-[5-(4,5-diphenyl-1H-imidazol-2-ylthio)pentyl]-1-heptanamine (0.87 g, 0.002 mol) and sodium bicarbonate (5%, 1 mL) in toluene (10 mL) at 0° was added, dropwise, a solution of cyclohexylchloroformate (0.32 g, 0.002 mol) in toluene (5 mL). The reaction mixture was allowed to warm to ambient temperature and stirred overnight. The solvent was removed under vacuum. The residue (1.0 g) was chromatographed with 7:3 hexane-ethyl acetate to give the title compound (0.61 g, 0.0011 mol) as a yellow oil. ¹H NMR (CDCl₃) δ11.1(bs,1H), 7.7–7.2(m,10H), 4.6(bs,1H), 3.3(t,2H,J=5.1Hz), 3.2(t,2H,J=7.5Hz), 3.0(t,2H,J=5.2Hz), 1.9–1.2(m,26H), 0.9–0.8(m,3H).

EXAMPLE 411

Preparation of phenyl N-[5-(4,5-bis(1-methylethyl)-1H-imidazol-2-ylthio]pentyl]-N-heptylcarbamate Part A. Employing the method of Example 118, Part B, but using phenyl chloroformate and triethylamine, phenyl N-heptyl-N-(5-hydroxypentyl)carbamate was obtained as an oil (3.18 g, 0.00989 mol). $^1$H NMR (CDCl$_3$) δ7.40-7.06(m,5H), 3.68-3.63(m,2H), 3.42-3.27(m,4H), 2.08-1.95(bs,1H), 1.75-1.26(m,16H), 0.90(t,3H).

Part B. Employing the method of Example 118, Part C, but using phenyl N-heptyl-N-(5-hydroxypentyl)carbamate, phenyl N-(5-bromopentyl)-N-heptylcarbamate was isolated as an oil (3.8 g, 0.0099 mol). $^1$H NMR (CDCl$_3$) δ7.39-7.07(m,5H), 3.47-3.25(m,6H), 1.97-1.89(m,2H), 1.75-1.26(m,14H), 0.87(t,3H).

Part C. Employing the method of Example 118, Part D, but using phenyl N-(5-bromopentyl)-N-heptylcarbamate, the title compound was isolated as an oil (0.3 g, 0.000615 mol). $^1$H NMR (DMSO-d$_6$) δ11.07(s,1H), 7.35(m,2H), 7.18(t,1H), 7.05(d,2H), 3.31(m,2H), 3.20(m,2H), 2.95(m,3H), 2.8(m,1H), 1.67-1.06(m,2H), 0.86(m,3H).

Additional carbamates, which are listed in Table 4, were prepared or could be prepared analogously according to the procedures of Examples 401 and 411.

TABLE 4

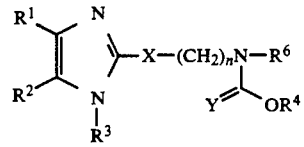

| Ex. No. | R$^1$ | R$^2$ | R$^3$ | R$^4$ | X | Y | n | R$^6$ | mp °C. |
|---|---|---|---|---|---|---|---|---|---|
| 401 | C$_6$H$_5$ | C$_6$H$_5$ | H | C$_6$H$_{11}$ | S | O | 5 | (CH$_2$)$_6$CH$_3$ | oil |
| 402 | C$_6$H$_5$ | C$_6$H$_5$ | H | C$_6$H$_5$ | S | O | 5 | (CH$_2$)$_6$CH$_3$ | oil$^{(a)}$ |
| 403 | C$_6$H$_5$ | C$_6$H$_5$ | H | CH$_2$CH(CH$_3$)$_2$ | S | O | 5 | (CH$_2$)$_6$CH$_3$ | oil$^{(b)}$ |
| 404 | C$_6$H$_5$ | C$_6$H$_5$ | H | CH$_2$CH$_3$ | S | O | 5 | (CH$_2$)$_6$CH$_3$ | oil$^{(c)}$ |
| 405 | C$_6$H$_5$ | C$_6$H$_5$ | H | (CH$_2$)$_7$CH$_3$ | S | O | 5 | (CH$_2$)$_6$CH$_3$ | oil$^{(d)}$ |
| 406 | C$_6$H$_5$ | C$_6$H$_5$ | H | 4-FC$_6$H$_4$ | S | O | 5 | (CH$_2$)$_6$CH$_3$ | oil$^{(e)}$ |
| 407 | C$_6$H$_5$ | C$_6$H$_5$ | H | (CH$_2$)$_2$CH$_3$ | S | O | 5 | (CH$_2$)$_6$CH$_3$ | oil$^{(f)}$ |
| 408 | C$_6$H$_5$ | C$_6$H$_5$ | H | CH$_2$C$_6$H$_5$ | S | O | 5 | (CH$_2$)$_6$CH$_3$ | oil$^{(g)}$ |
| 409 | 4-(CH$_3$)$_2$NC$_6$H$_4$ | 4-(CH$_3$)$_2$NC$_6$H$_4$ | H | C$_6$H$_5$ | S | O | 5 | (CH$_2$)$_6$CH$_3$ | oil$^{(h)}$ |
| 410 | 4-CH$_3$OC$_6$H$_4$ | 4-CH$_3$OC$_6$H$_4$ | H | C$_6$H$_5$ | S | O | 5 | (CH$_2$)$_6$CH$_3$ | oil$^{(i)}$ |
| 411 | (CH$_3$)$_2$CH | (CH$_3$)$_2$CH | H | C$_6$H$_5$ | S | O | 5 | (CH$_2$)$_6$CH$_3$ | oil |
| 412 | n-C$_3$H$_7$ | n-C$_3$H$_7$ | H | n-C$_3$H$_7$ | S | O | 5 | (CH$_2$)$_6$CH$_3$ | |
| 413 | 2-pyridinyl | 2-pyridinyl | H | C$_6$H$_{11}$ | O | O | 5 | (CH$_2$)$_6$CH$_3$ | |
| 414 | 3-pyridinyl | 3-pyridinyl | H | 2,4-diCH$_3$OC$_6$H$_3$ | CH$_2$ | O | 5 | (CH$_2$)$_6$CH$_3$ | |
| 415 | 4-pyridinyl | 4-pyridinyl | H | CH$_2$-2,4,6-triFC$_6$H$_2$ | NH | O | 5 | (CH$_2$)$_6$CH$_3$ | |
| 416 | 2-CH$_3$OC$_6$H$_4$ | 2-CH$_3$OC$_6$H$_4$ | H | 3-F—C$_6$H$_4$ | S | H$_2$ | 5 | (CH$_2$)$_6$CH$_3$ | |
| 417 | 3-CH$_3$OC$_6$H$_4$ | 3-CH$_3$OC$_6$H$_4$ | H | CH(CH$_3$)$_2$ | O | O | 5 | (CH$_2$)$_6$CH$_3$ | |
| 418 | C$_6$H$_{11}$ | C$_6$H$_{11}$ | H | C$_6$H$_5$ | CH$_2$ | O | 5 | (CH$_2$)$_6$CH$_3$ | |
| 419 | C$_6$H$_5$ | 4-(CH$_3$)$_2$NC$_6$H$_4$ | H | (CH$_2$)$_7$CH$_3$ | NH | O | 5 | (CH$_2$)$_6$CH$_3$ | |
| 420 | 2-furanyl | 2-furanyl | H | 2,6-diCl—C$_6$H$_3$ | S | O | 5 | (CH$_2$)$_6$CH$_3$ | |
| 421 | 4-(t-C$_4$H$_9$)C$_6$H$_4$ | 4-(t-C$_4$H$_9$)C$_6$H$_4$ | H | CH$_3$ | O | H$_2$ | 5 | (CH$_2$)$_6$CH$_3$ | |
| 422 | 2-thienyl | 2-thienyl | H | (C$_6$H$_4$) (C$_6$H$_5$) | CH$_2$ | O | 5 | (CH$_2$)$_6$CH$_3$ | |
| 423 | 4-OH—C$_6$H$_4$ | 4-OH—C$_6$H$_4$ | CH$_3$ | 2,4-diFC$_6$H$_3$ | NH | O | 5 | (CH$_2$)$_6$CH$_3$ | |
| 424 | (CH$_3$)$_2$CH | (CH$_3$)$_2$CH | CH$_3$ | C$_6$H$_{11}$ | S | O | 5 | (CH$_2$)$_6$CH$_3$ | |
| 425 | C$_6$H$_5$CH$_2$ | C$_6$H$_5$CH$_2$ | CH$_3$ | C$_6$H$_5$ | O | O | 5 | (CH$_2$)$_6$CH$_3$ | |
| 426 | C$_6$H$_4$-2-OCH$_2$O-2'-C$_6$H$_4$ | | H | 2,4-diFC$_6$H$_3$ | CH$_2$ | H$_2$ | 3 | (CH$_2$)$_6$CH$_3$ | |
| 427 | C$_6$H$_4$OC$_6$H$_4$ | | H | C$_6$H$_{11}$ | NH | O | 3 | (CH$_2$)$_6$CH$_3$ | |
| 428 | 4-CH$_3$OC$_6$H$_4$ | 4-(CH$_3$)$_2$NC$_6$H$_4$ | H | C$_6$H$_{11}$ | O | O | 8 | (CH$_2$)$_6$CH$_3$ | |
| 429 | 4-CH$_3$OC$_6$H$_4$ | C$_6$H$_{11}$ | H | CH$_2$-2,4-diFC$_6$H$_3$ | CH$_2$ | O | 5 | (CH$_2$)$_3$CH$_3$ | |
| 430 | 4-CH$_3$OC$_6$H$_4$ | (CH$_3$)$_2$CH | H | CH$_2$-2,4-diFC$_6$H$_3$ | NH | H$_2$ | 5 | (CH$_2$)$_8$CH$_3$ | |
| 431 | 4-(CH$_3$)NC$_6$H$_4$ | C$_6$H$_{11}$ | H | 2,4-diFC$_6$H$_3$ | S | O | 5 | CH$_3$ | |
| 432 | 4-(CH$_3$)NC$_6$H$_4$ | (CH$_3$)$_2$CH | H | 2,4-diFC$_6$H$_3$ | O | O | 5 | C$_6$H$_5$ | |
| 433 | C$_6$H$_{11}$ | (CH$_3$)$_2$CH | H | CH$_2$-2,4-diFC$_6$H$_3$ | CH$_2$ | O | 5 | 3-FC$_6$H$_4$ | |
| 434 | C$_6$H$_5$ | 4-CH$_3$OC$_6$H$_4$ | H | (CH$_2$)$_7$CH$_3$ | NH | O | 5 | (CH$_2$)$_3$CH$_3$ | |
| 435 | C$_6$H$_5$ | 4-(CH$_3$)$_2$NC$_6$H$_4$ | H | (CH$_2$)$_7$CH$_3$ | S | H$_2$ | 5 | C$_6$H$_5$ | |
| 436 | (CH$_3$)$_2$CH | (CH$_3$)$_2$CH | H | 2,4-diFC$_6$H$_3$ | S | O | 5 | (CH$_2$)$_6$CH$_3$ | |
| 437 | 4-CH$_3$SC$_6$H$_4$ | 4-CH$_3$SC$_6$H$_4$ | H | 2,4-diFC$_6$H$_3$ | S | O | 5 | (CH$_2$)$_6$CH$_3$ | |
| 438 | 4-CH$_3$SOC$_6$H$_4$ | 4-CH$_3$SOC$_6$H$_4$ | H | 2,4-diFC$_6$H$_3$ | NH | O | 5 | (CH$_2$)$_6$CH$_3$ | |
| 439 | 4-CH$_3$SO$_2$C$_6$H$_4$ | 4-CH$_3$SO$_2$C$_6$H$_4$ | H | 2,4-diFC$_6$H$_3$ | CH$_2$ | O | 5 | (CH$_2$)$_6$CH$_3$ | |
| 440 | C$_6$H$_5$ | 4-CH$_3$SC$_6$H$_4$ | C$_6$H$_5$ | 2,4-diFC$_6$H$_3$ | S | O | 5 | (CH$_2$)$_6$CH$_3$ | |
| 441 | C$_6$H$_5$ | 4-CH$_3$SOC$_6$H$_4$ | CH$_2$CH$_3$ | 2,4-diFC$_6$H$_3$ | NH | O | 5 | (CH$_2$)$_6$CH$_3$ | |
| 442 | C$_6$H$_5$ | 4-CH$_3$SO$_2$C$_6$H$_4$ | CH$_2$C$_6$H$_5$ | 2,4-diFC$_6$H$_3$ | CH$_2$ | O | 5 | (CH$_2$)$_6$CH$_3$ | |
| 443 | 4-(CH$_3$)$_2$NC$_6$H$_4$ | 4-(CH$_3$)$_2$NC$_6$H$_4$ | CH$_3$ | n-C$_3$H$_7$ | S | O | 5 | (CH$_2$)$_6$CH$_3$ | |
| 444 | 4-(CH$_3$)$_2$NC$_6$H$_4$ | 4-(CH$_3$)$_2$NC$_6$H$_4$ | H | C$_6$H$_{11}$ | S | H$_2$ | 5 | (CH$_2$)$_6$CH$_3$ | |
| 445 | 4-(CH$_3$)$_2$NC$_6$H$_4$ | 4-(CH$_3$)$_2$NC$_6$H$_4$ | H | CH(CH$_3$)$_2$ | S | O | 5 | (CH$_2$)$_6$CH$_3$ | |
| 446 | 4-(CH$_3$)$_2$NC$_6$H$_4$ | 4-(CH$_3$)$_2$NC$_6$H$_4$ | H | C$_6$H$_5$ | SO | O | 5 | (CH$_2$)$_6$CH$_3$ | |
| 447 | 4-(CH$_3$)$_2$NC$_6$H$_4$ | 4-(CH$_3$)$_2$NC$_6$H$_4$ | H | 2,4-diFC$_6$H$_3$ | S | O | 3 | (CH$_2$)$_6$CH$_3$ | |
| 448 | 4-(CH$_3$)$_2$NC$_6$H$_4$ | 4-(CH$_3$)$_2$NC$_6$H$_4$ | H | C$_6$H$_{11}$ | S | O | 8 | (CH$_2$)$_6$CH$_3$ | |
| 449 | 4-(CH$_3$)$_2$NC$_6$H$_4$ | 4-(CH$_3$)$_2$NC$_6$H$_4$ | H | (CH$_2$)$_7$CH$_3$ | SO$_2$ | O | 5 | C$_6$H$_5$ | |
| 450 | 4-CH$_3$OC$_6$H$_4$ | 4-CH$_3$OC$_6$H$_4$ | H | n-C$_3$H$_7$ | S | O | 5 | (CH$_2$)$_6$CH$_3$ | |
| 451 | 4-CH$_3$OC$_6$H$_4$ | 4-CH$_3$OC$_6$H$_4$ | H | C$_6$H$_{11}$ | S | H$_2$ | 5 | (CH$_2$)$_6$CH$_3$ | |
| 452 | 4-CH$_3$OC$_6$H$_4$ | 4-CH$_3$OC$_6$H$_4$ | CH$_3$ | CH(CH$_3$)$_2$ | S | O | 5 | (CH$_2$)$_6$CH$_3$ | |
| 453 | 4-CH$_3$OC$_6$H$_4$ | 4-CH$_3$OC$_6$H$_4$ | H | C$_6$H$_5$ | SO | O | 5 | (CH$_2$)$_6$CH$_3$ | |
| 454 | 4-CH$_3$OC$_6$H$_4$ | 4-CH$_3$OC$_6$H$_4$ | H | 2,4-diFC$_6$H$_3$ | S | O | 3 | (CH$_2$)$_6$CH$_3$ | |
| 455 | 4-CH$_3$OC$_6$H$_4$ | 4-CH$_3$OC$_6$H$_4$ | H | C$_6$H$_{11}$ | SO$_2$ | O | 8 | (CH$_2$)$_6$CH$_3$ | |
| 456 | 4-CH$_3$OC$_6$H$_4$ | 4-CH$_3$OC$_6$H$_4$ | H | (CH$_2$)$_7$CH$_3$ | S | S | 5 | C$_6$H$_5$ | |

TABLE 4-continued

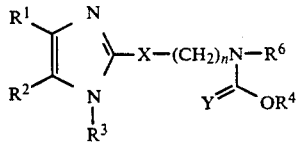

| Ex. No. | $R^1$ | $R^2$ | $R^3$ | $R^4$ | X | Y | n | $R^6$ | mp °C. |
|---|---|---|---|---|---|---|---|---|---|
| 457 | 4-CH$_3$OC$_6$H$_4$ | 4-CH$_3$OC$_6$H$_4$ | H | CH$_2$CH(CH$_3$)$_2$ | S | O | 5 | (CH$_2$)$_6$CH$_3$ | oil$^{(j)}$ |

Footnotes To Table 4

$^{(a)1}$H NMR (CDCl$_3$) δ 10.6(s, 1H), 7.7–7.0(m, 15H), 3.4(q, 4H, J=4.7Hz), 2.9(t, 2H, J=5.8Hz), 1.8–1.2(m, 16H), 0.95–0.75(m, 3H).

$^{(b)1}$H NMR (CDCl$_3$) δ 10.9(s, 1H), 7.75–7.1(m, 10H), 3.75(d, 2H, J=6.3Hz), 3.3(t, 2H, J=6.0Hz), 3.15(t, 2H, J=7.5Hz), 3.0(t, 2H, J=6.2Hz), 2.0–1.2(m, 17H), 0.9(t, 9H, J=3.2Hz).

$^{(c)1}$H NMR (CDCl$_3$) δ 10.9(s, 1H), 7.75–7.1(m, 10H), 4.0(d, 2H, J=6.8Hz), 3.4–2.95(m, 6H), 1.9–1.1(m, 19H), 1.0–0.8(m, 3H).

$^{(d)1}$H NMR (CDCl$_3$) δ 10.7(s, 1H), 7.7–7.2(m, 10H), 4.1–3.9(m, 2H), 3.4–2.9(m, 6H), 1.8–1.2(m, 28H), 0.9–0.8(m, 6H).

$^{(e)1}$H NMR (CDCl$_3$) δ 10.4(s, 1H), 7.7–6.8(m, 14H), 3.5–2.9(m, 6H), 1.9–1.1(m, 16H), 1.0–0.8(m, 3H).

$^{(f)1}$H NMR (CDCl$_3$) δ 10.9(s, 1H), 7.75–7.1(m, 10H), 4.0(q, 2H, J=6.9Hz), 3.3(t, 2H, J=9.5Hz), 3.2(t, 2H, J=7.5Hz), 3.0(t, 2H, J=7.8Hz), 1.8–1.1(m, 18H), 0.9(t, 3H, J=7.2Hz).

$^{(g)1}$H NMR (CDCl$_3$) δ 10.5(s, 1H), 7.7–7.2(m, 15H), 5.05(s, 2H), 3.3(q, 2H, J=5.7Hz), 3.2(t, 2H, J=7.4Hz), 3.0(q, 2H, J=5.4Hz), 1.8–1.1(m, 16H), 0.9(t, 3H, J=6.4Hz).

$^{(h)1}$H NMR (CDCl$_3$) δ 10.0–9.8(bs, 1H), 7.57–7.03(m, 9H), 6.63(m, 4H), 3.43–3.26(m, 4H), 3.09–2.86(bs, 14H), 1.81–1.25(m, 16H), 0.89(t, 3H).

$^{(i)1}$H NMR (DMSO-d$_6$) δ 12.34(s, 1H), 7.39–7.22(m, 6H), 7.19(t, 1H), 7.06(d, 2H), 6.94(d, 2H), 6.84(d, 2H), 3.77(s, 3H), 3.72(s, 3H), 3.40–3.20(m, 4H), 3.09(m, 2H), 1.75–1.17(m, 16H), 0.84(m, 3H).

$^{(j)}$NMR (CDCl$_3$) δ 7.6–7.3(m, 4H), 6.9–6.8(m, 4H), 3.9–3.7(m, 8H), 3.4–2.9(m, 5H), 2.0–1.2(m, 19H), 1.0–0.8(m, 9H).

EXAMPLE 458

Preparation of N'-(2,4-difluorophenyl)-N-[3.3-dimethyl-5-(4,5-diphenyl-1H-imidazol-2-ylthio)pentyl]-N-heptylurea Part A. The method of Little, R. D. and Muller, G. W., J. Am. Chem. Soc. 1981, 103, p. 2744 was used to prepare 3,3-dimethyl-5-hydroxypentanoic acid lactone. This lactone (12.85 g, 100.3 mmol) was dissolved in toluene (100 mL) under nitrogen atmosphere, and treated with heptylamine (17.0 mL, 115 mmol). After refluxing for 18 hours, the mixture was cooled, washed with an equal volume aq. hydrochloric acid (1N), dried over magnesium sulfate, and concentrated under vacuum. The product was purified by elution through a plug of silica gel with ethyl acetate, and the eluant was concentrated under vacuum to afford N-heptyl-3,3-dimethyl-5-hydroxypentanamide (24.0 g, 98.7 mmol, 98%) as an oil. $^1$H NMR (CDCl$_3$) δ6.32(br s,1H); 3.78(t,2H,J=5.7Hz); 3.22(q,2H,J=6.7Hz); 2.25(s,2H); 1.67(t,2H,J=5.7Hz); 1.57–1.45(m,2H); 1.38–1.25(m,8H); 1.02(s,6H); 0.88(t,3H,J=7.0Hz).

Part B. A slurry of lithium aluminum hydride (5.50 g, 145 mmol) in tetrahydrofuran (100 mL) was cooled to 0° C., and a solution of the amide prepared in Part A (11.48 g, 47.2 mmol) in tetrahydrofuran (50 mL) was added dropwise over 1 hour. The ice bath was removed, and the mixture was heated to reflux for 18 hours. After cooling to 0° C., the mixture was quenched by the slow dropwise addition of water (6 mL), aq. NaOH (18 mL, 15%), and water (18 mL). The solution was filtered through a plug of Celite®, dried over potassium carbonate, and concentrated under vacuum to afford N-heptyl-3,3-dimethyl-5-hydroxypentanamine as a clear, colorless oil (7.61 g, 33.2 mmol, 70%). $^1$H NMR (CDCl$_3$) δ3.70(dt,2H,J=10.2,7.0Hz); 2.70–2.55(m,2H); 2.39–2.29(m,2H); 1.56(dt,2H,J=12.1,7.0Hz); 1.51–1.41(m,6H); 1.36–1.24(m,8H); 0.91(s,6H); 0.88(t,3H,J=6.9Hz).

Part C. A solution of the amine prepared in Part C (4.26 g, 18.6 mmol) in methylene chloride (20 mL) was cooled to 0° C., and a solution of 2,4-difluorophenyl isocyanate (2.20 mL, 18.6 mmol) in methylene chloride (20 mL) was added dropwise with stirring over 1 hour. After slow warming to ambient temperature over 18 hours, the reaction mixture was concentrated under vacuum, and the residual oil was purified by flash chromatography to afford N'-(2,4-difluorophenyl)-N-(3,3-dimethyl-5-hydroxypentyl)-N-heptylurea as a colorless oil (2.31 g, 6.01 mmol, 32%). $^1$H NMR (CDCl$_3$) δ7.93(br q,1H,J=6.2Hz); 6.89–6.78(m,3H); 3.76(t,2H,J=6.3Hz); 3.38–3.24(m,4H); 2.36(br s,1H); 1.65–1.52(m,6H); 1.36–1.24(m,8H); 0.97(s,6H); 0.89(t,3H,J=6.6Hz).

Part D. A solution of the alcohol prepared in Part C (2.05 g, 5.33 mmol) in methylene chloride (30 mL) was cooled to 0° C. and treated with solid carbon tetrabromide (2.14 g, 6.45 mmol). Then, a solution of triphenylphosphine (1.69 g, 6.44 mmol) in methylene chloride (20 mL) was added dropwise. After stirring for 18 hours, the mixture was concentrated under vacuum and purified by flash chromatography to afford N'-(2,4-difluorophenyl)-N-(5-bromo-3,3-dimethylpentyl)-N-heptylurea as a clear, colorless oil (1.68 g, 3.75 mmol, 70%). $^1$H NMR (CDCl$_3$) δ8.10–8.02(m,1H); 6.88–6.80(m,2H); 6.37(br d,1H,J=3.3Hz); 3.44–3.38(m,2H); 3.36–3.24(m,4H); 1.93–1.85(m,2H); 1.70–1.55(m,4H); 1.40–1.25(m,8H); 0.98(s, 6H); 0.89(t, 3H,J=7.0Hz).

Part E. A slurry of the bromide prepared in Part D (1.60 g, 3.58 mmol), 4,5-diphenyl-1H-imidazole-2-thiol (0.82 g, 3.25 mmol), potassium carbonate (0.55 g, 3.98 mmol) and tetra-n-butylammonium iodide (0.264 g, 0.71 mmol) in tetrahydrofuran (20 mL) was heated to reflux for 18 hours, then cooled, poured into water (100 mL), and extracted with methylene chloride (100 mL). The aqueous phase was neutralized to pH 6 with HCl (6N), then reextracted with methylene chloride. The extracts were combined, dried over magnesium sulfate and concentrated under vacuum to afford the title compound as a solid, which was recrystallized to purity from ether-hexane, mp 138°–9° C. $^1$H NMR (CDCl$_3$) δ10.98(br s,1H); 7.74–7.66(m,1H); 7.60–7.51(br m,2H); 7.34–7.26(m,2H); 7.24–7.14(m,6H); 6.86–6.78(m,1H); 6.75–6.69(m,1H); 6.44(br s,1H); 3.23–3.14(m,6H); 1.80–1.66(m,2H); 1.62–1.54(m,4H); 1.39–1.27(m,8H); 0.94(s,6H); 0.90(t,3H,J=6.6Hz).

Additional branched compounds, which are listed in Table 5, could be prepared analogously according to the procedure of Example 458.

TABLE 5

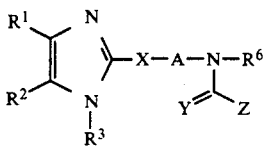

| Ex. No. | R¹ | R² | R³ | X | A | Y | Z | R⁶ |
|---|---|---|---|---|---|---|---|---|
| 458 | $C_6H_5$ | $C_6H_5$ | H | S | $(CH_2)_2C(CH_3)_2(CH_2)_2$ | O | $NH-2,4-diFC_6H_3$ | $(CH_2)_6CH_3$* |
| 459 | $C_6H_5$ | $C_6H_5$ | H | S | $CH_2CH(CH_3)(CH_2)_3$ | O | $NH-2,4-diFC_6H_3$ | $(CH_2)_6CH_3$ |
| 460 | $C_6H_5$ | $C_6H_5$ | H | $CH_2$ | $(CH_2)_3CH(CH_3)CH_2$ | S | $NH-2,4-diFC_6H_3$ | $(CH_2)_3CH_3$ |
| 461 | $C_6H_5$ | $C_6H_5$ | H | NH | $(CH_2)_3C(CH_3)_2CH_2$ | $H_2$ | $NH-2,4-diFC_6$ | $(CH_2)_8CH_3$ |
| 462 | $C_6H_5$ | $C_6H_5$ | H | O | $(CH_2)CH(C_5H_{11})(CH_2)_2$ | O | $CH_2CH(CH_3)_2$ | $C_6H_5$ |
| 463 | $4-(CH_3)_2NC_6H_4$ | $4-(CH_3)_2NC_6H_4$ | $CH_3$ | S | $CH(CH_3)(CH_2)_4$ | S | $CH_2CH(CH_3)_2$ | $2,4-diFC_6H_3$ |
| 464 | $4-(CH_3)_2NC_6H_4$ | $4-(CH_3)_2NC_6H_4$ | H | $CH_2$ | $CH_2CH=CH(CH_2)_2$ | $H_2$ | $CH_2CH(CH_3)_2$ | $(CH_2)_6CH_3$ |
| 465 | $4-(CH_3)_2NC_6H_4$ | $4-(CH_3)_2NC_6H_4$ | $CH_2CH_3$ | NH | $(CH_2)_3CH=CH(CH_2)_2$ | O | $O(CH_2)_7CH_3$ | $(CH_2)_3CH_3$ |
| 466 | $4-(CH_3)_2NC_6H_4$ | $4-(CH_3)_2NC_6H_4$ | $CH_2C_6H_5$ | O | $CH_2C\equiv C(CH_2)_2$ | S | $O(CH_2)_7CH_3$ | $CH_3$ |
| 467 | $4-CH_3OC_6H_4$ | $4-CH_3OC_6H_4$ | $C_6H_5$ | S | $(CH_2)_3C\equiv C(CH_2)_2$ | $H_2$ | $O(CH_2)_7CH_3$ | $C_6H_5$ |
| 468 | $4-CH_3OC_6H_4$ | $4-CH_3OC_6H_4$ | H | $CH_2$ | $CH_2CH(CH_3)(CH_2)_3$ | O | $NHCH(CH_3)_2$ | $(CH_2)_6CH_3$ |
| 469 | $4-CH_3OC_6H_4$ | $4-CH_3OC_6H_4$ | H | NH | $(CH_2)_3CH(CH_3)CH_2$ | S | $NHCH(CH_3)_2$ | $(CH_2)_3CH_3$ |
| 470 | $4-CH_3OC_6H_4$ | $4-CH_3OC_6H_4$ | H | O | $(CH_2)_3C(CH_3)_2CH_2$ | $H_2$ | $NHCH(CH_3)_2$ | $(CH_2)_8CH_3$ |
| 471 | $(CH_3)_2CH$ | $(CH_3)_2CH$ | H | S | $(CH_2)_2CH(C_5H_{11})(CH_2)_2$ | O | $(CH_2)_7CH_3$ | $C_6H_5$ |
| 472 | $(CH_3)_2CH$ | $(CH_3)_2CH$ | $CH_3$ | $CH_2$ | $CH(CH_3)(CH_2)_4$ | S | $(CH_2)_7CH_3$ | $2,4-diFC_6H_3$ |
| 473 | $(CH_3)_2CH$ | $(CH_3)_2CH$ | H | NH | $CH_2CH=CH(CH_2)_2$ | $H_2$ | $(CH_2)_7CH_3$ | $(CH_2)_6CH_3$ |
| 474 | $(CH_3)_2CH$ | $(CH_3)_2CH$ | H | O | $(CH_2)_3CH=CH(CH_2)_2$ | O | $OC_6H_5$ | $(CH_2)_3CH_3$ |
| 475 | $C_6H_{11}$ | $C_6H_{11}$ | H | S | $CH_2C\equiv C(CH_2)_2$ | S | $OC_6H_5$ | $CH_3$ |
| 476 | $C_6H_{11}$ | $C_6H_{11}$ | $C_6H_5$ | $CH_2$ | $(CH_2)_3C\equiv C(CH_2)_2$ | $H_2$ | $OC_6H_5$ | $C_6H_5$ |
| 477 | $C_6H_{11}$ | $C_6H_{11}$ | H | NH | $CH_2CH(CH_3)(CH_2)_3$ | O | $NH(CH_2)_7CH_3$ | $(CH_2)_6CH_3$ |
| 478 | $C_6H_{11}$ | $C_6H_{11}$ | H | O | $(CH_2)_3CH(CH_3)CH_2$ | S | $NH(CH_2)_7CH_3$ | $(CH_2)_3CH_3$ |
| 479 | $C_6H_5$ | $4-CH_3OC_6H_4$ | H | S | $(CH_2)_3C(CH_3)_2CH_2$ | $H_2$ | $NH(CH_2)_7CH_3$ | $(CH_2)_8CH_3$ |
| 480 | $C_6H_5$ | $4-CH_3OC_6H_4$ | H | $CH_2$ | $(CH_2)_2CH(C_5H_{11})(CH_2)_2$ | O | $CH_2C_6H_5$ | $C_6H_5$ |
| 481 | $C_6H_5$ | $4-CH_3OC_6H_4$ | $CH_3$ | NH | $CH(CH_3)(CH_2)_4$ | S | $C_6H_5$ | $2,4-diFC_6H_3$ |
| 482 | $C_6H_5$ | $4-CH_3OC_6H_4$ | H | O | $CH_2CH=CH(CH_2)_2$ | $H_2$ | $CH_2C_6H_5$ | $(CH_2)_6CH_3$ |
| 483 | $C_6H_5$ | $4-(CH_3)_2NC_6H_4$ | H | S | $(CH_2)_3CH=CH(CH_2)_2$ | O | $OCH(CH_3)_2$ | $(CH_2)_3CH_3$ |
| 484 | $C_6H_5$ | $4-(CH_3)_2NC_6H_4$ | H | $CH_2$ | $CH_2C\equiv C(CH_2)_2$ | S | $OCH(CH_3)_2$ | $CH_3$ |
| 485 | $C_6H_5$ | $4-(CH_3)_2NC_6H_4$ | $C_6H_5$ | NH | $(CH_2)_3C\equiv C(CH_2)_2$ | $H_2$ | $OCH(CH_3)_2$ | $C_6H_5$ |
| 486 | $4-(CH_3)_2NC_6H_4$ | $4-(CH_3)_2NC_6H_4$ | H | S | $CH_2CH(CH_3)(CH_2)_3$ | O | $CH_2CH(CH_3)_2$ | $(CH_2)_3CH_3$ |
| 487 | $4-(CH_3)_2NC_6H_4$ | $4-(CH_3)_2NC_6H_4$ | H | S | $(CH_2)_3CH(CH_3)CH_2$ | O | $O(CH_2)_7CH_3$ | $(CH_2)_3CH_3$ |
| 488 | $4-(CH_3)_2NC_6H_4$ | $4-(CH_3)_2NC_6H_4$ | H | S | $(CH_2)_3C(CH_3)_2CH_2$ | O | $NH-2,4-diFC_6H_3$ | $(CH_2)_6CH_3$ |
| 489 | $4-(CH_3)_2NC_6H_4$ | $4-(CH_3)_2NC_6H_4$ | H | SO | $(CH_2)_2CH(C_5H_{11})(CH_2)_2$ | O | $NH-2,4-diFC_6H_3$ | $(CH_2)_8CH_3$ |
| 490 | $4-(CH_3)_2NC_6H_4$ | $4-(CH_3)_2NC_6H_4$ | H | $SO_2$ | $CH(CH_3)(CH_2)_4$ | O | $NH(CH_2)_2CH_3$ | $(CH_2)_6CH_3$ |
| 491 | $4-CH_3OC_6H_4$ | $4-CH_3OC_6H_4$ | H | S | $CH_2CH=CH(CH_2)_2$ | O | $CH_2-2,4-diFC_6H_3$ | $(CH_2)_3CH_3$ |
| 492 | $4-CH_3OC_6H_4$ | $4-CH_3OC_6H_4$ | H | S | $(CH_2)_3CH=CH(CH_2)_2$ | O | $O-2,4-diFC_6H_3$ | $(CH_2)_3CH_3$ |
| 493 | $4-CH_3OC_6H_4$ | $4-CH_3OC_6H_4$ | H. | S | $CH_2C\equiv C(CH_2)_2$ | O | $CH_2-CH(CH_3)_2$ | $(CH_2)_6CH_3$ |
| 494 | $4-CH_3OC_6H_4$ | $4-CH_3OC_6H_4$ | H | S | $(CH_2)_3C\equiv C(CH_2)_2$ | O | $CH_2CH_3$ | $(CH_2)_6CH_3$ |
| 495 | $4-(CH_3)_2NC_6H_4$ | $4-(CH_3)_2NC_6H_4$ | H | S | $(CH_2)_2C(CH_3)_2(CH_2)_2$ | O | $CH_2C_6H_{11}$ | $(CH_2)_6CH_3$ |
| 496 | $4-CH_3OC_6H_4$ | $4-CH_3OC_6H_4$ | H | S | $(CH_2)_2C(CH_3)_2(CH_2)_2$ | O | $NHCH(CH_3)_2$ | $(CH_2)_6CH_3$ |
| 497 | $(CH_3)_2CH$ | $(CH_3)_2CH$ | H | S | $(CH_2)_2C(CH_3)_2(CH_2)_2$ | O | $OC_6H_5$ | $(CH_2)_6CH_3$ |
| 498 | $C_6H_{11}$ | $C_6H_{11}$ | H | S | $(CH_2)_2C(CH_3)_2(CH_2)_2$ | O | $CH_2CH(CH_3)_2$ | $(CH_2)_6CH_3$ |

*m.p. = 138–139° C.

EXAMPLE 499

Preparation of N-[5-(4,5-diphenyl-1H-imidazol-2-ylthio)-pentyl]-N-heptyl-N'-phenylguanidine A solution of N-[5-(4,5-diphenyl-1H-imidazol-2-ylthio)pentyl]-N-heptanamine (0.50 g, 0.00115 mol) and N-phenyl-S-methyl-carbamimidothioate hydrochloride (0.34 g, 0.00115 mol) in acetonitrile (10 mL) and triethylamine (0.5 mL) was heated to reflux under a nitrogen atmosphere for 4 hours. The reaction was allowed to cool to ambient temperature, was diluted with ethyl acetate (50 mL), washed with 10% aqueous sodium bicarbonate (25 mL), water, brine, dried over magnesium sulfate and concentrated in vacuo to give a crude oil. The product was crystallized from acetonitrile to give the title compound (0.4 g, 0.00072 mol) as a white powder, mp 135°–6°. ¹H NMR (CDCl₃) δ7.45(m,4H), 7.23(m,8H), 6.94(t,1H), 6.82(d,2H), 3.3(t,2H), 3.16(t,2H), 3.03(t,2H), 1.7–1.16(m,16H), 0.87(t,3H).

EXAMPLE 500

Preparation of N-[5-[4,5-bis(4-methoxyphenyl)-1H-imidazol-2-ylthio]-pentyl]-N-heptyl-N'-phenylguanidine Employing the method of Example 499 but using N-[5-[4,5-bis(4-methoxyphenyl)-1H-imidazol-2-ylthio]-pentyl]-1-heptanamine the title compound was obtained as an off white foam (0.61 g, 0.00099 mol) mp 68°–72°. ¹H NMR (CDCl₃) δ7.37(d,4H), 7.22(m,2H), 6.97(t,1H), 6.90–6.78(m,6H), 3.75(S,6H), 3.31(t,2H), 3.20(t,2H), 3.00(t,2H), 1.7–1.15(m,16H), 0.87(t,2H).

EXAMPLE 501

Preparation of N-[5-(4,5-diphenyl-1H-imidazol-2-ylthio)pentyl]-N-heptyl-N'-(1-methylethyl)guanidine Employing the method of Example 499 but using N-(1-methylethyl)-S-methyl-carbamimidothioate hydrochloride, the title compound was obtained as a pale yellow glass (0.31 g, 0.00059 mol), mp 98°–101°. ¹H NMR (CDCl₃) δ12.75(bs,1H), 7.85–7.68(bs,1H), 7.55(d,4H), 7.30–7.16(m,6H), 6.25–6.15(bs,1H), 4.10–3.95(m,1H), 3.35(m,2H), 3.19(m,2H), 2.93(m,2H), 1.55–1.10(m,22H), 0.85(t,3H).

UTILITY

The compounds of the present invention are inhibitors of the enzyme acyl-CoA: cholesterol acyltransferase and are thus effective in inhibiting esterification and transport of cholesterol across the intestinal wall. In addition, the compounds are useful in preventing the formation of cholesterol ester rich macrophages (foam cells) in the arterial wall through the inhibition of cholesterol ester formation. Foam cells are a source of the large quantity of cholesterol ester found in atheromatous lesions as opposed to the surrounding undiseased tissue. Thus inhibition of ACAT would decrease the accumulation and storage of cholesterol esters in the arterial wall and prevent or inhibit the formation of atheromatous lesions.

A. Assay of the Inhibition of Acyl-CoA: Cholesterol Acyltransferase (ACAT) in Hepatic Microsomes The ability of the compounds to inhibit ACAT, the enzyme responsible for the intracellular synthesis of cholesteryl esters, was tested as follows. Male Sprague Dawley rats weighing 150–300 g, were fed rat chow ad libitum. The animals were fasted for twenty-four hours prior to being sacrificed by decapitation. The livers were perfused in situ with 50 ml of cold 0.25M sucrose, excised, and homogenized in three volumes of 0.1M phosphate buffer, pH 7.4, that contained 0.5 mM EDTA (ethylenediaminetetraacetic acid), 1.0 mM glutathione, 0.25M sucrose and 20 mM leupeptin. Microsomes were obtained by differential centrifugation; the supernatant from an initial spin at 15,000×g for 15 minutes was centrifuged at 105,000×g for 1 hour to pellet the microsomes. The microsomes were suspended in homogenization buffer, reisolated by centrifugation, and stored at −70° C. Microsomes were used within one month of preparation.

The control assay in a final volume of 200 μl consisted of 200 μg of microsomal protein, 75 μM $^{14}C$-oleoyl-CoA (10,000 dpm/nmol) in 0.1M phosphate, pH 7.4, that contained 1 mM glutathione. Compounds were added in 5 μl of DMSO (dimethyl sulfoxide) and additional controls were run with DMSO only. All components, except the oleoyl-CoA, were preincubated for 15 min. at 37° C. prior to the initiation of the reaction by the addition of oleoyl-CoA. The assay was terminated after 10 min by the addition of 4 ml of chloroform:methanol (2:1, v/v). 20,000 dpm of $^{3}H$-cholesteryl oleate and 10 μg of unlabeled cholesteryl oleate and oleic acid were added as an internal standard and carriers, respectively. After allowing 10 min. for lipid extraction, the samples were centrifuged at 1,000×g for 10 min. to separate the solvent layers. The chloroform layer containing the neutral lipids was spotted onto a Baker SI250-Pa silica gel TLC plate and the plate developed using a hexane: diethyl ether: acetic acid (170:30:1 v/v/v) mobile phase. The lipids were visualized by their interaction with iodine vapor and the cholesteryl ester spot was scraped into a scintillation vial and counted. The specific activity of ACAT in the control incubation averaged 260 pmol/min/mg microsomal protein. The inhibition of ACAT activity by the compounds is shown in Table 6; the data are expressed as the concentration at which ACAT activity is inhibited by 50% ($IC_{50}$).

B. Assay of the Inhibition of Cholesterol Esterification in Mammalian Cells

The esterification of cholesterol was determined in the murine macrophage-like cell line J774.A1. Cells were seeded in 35 mm wells at a density of 300,000 cells per well in 2 mls of Dulbecco's Eagle Medium (DMEM) supplemented with 10% fetal bovine serum (FBS). Cells were incubated at 37° C. in an atmosphere of 5% $CO_2$ and 93% humidity. After 24 hours the media was changed to 0.68 mls 10% FBS-DMEM containing 34 μg of acetylated human low density lipoprotein (ac-LDL) to increase the intracellular concentration of cholesterol and promote esterification. At 41 hours, various inhibitors were added to the cells in DMSO (10 μl/ml maximum). At 43 hours, the cells were pulsed with 0.1 mM $^{14}C$-oleic acid (10,000 dpm/nmol) complexed with BSA (bovine serum albumin) to follow cholesterol ester formation. The experiment was terminated at 45 hours by washing the monolayers 3 times with 3 ml of Tris-buffered saline at 4° C. The lipids were extracted by incubating the monolayers with 1.5 ml of hexane:isopropanol (3:2, v/v) for 30 min. under gentle agitation. During this period, 10,000 dpm 3H-cholesteryl linoleate and 10 μg of cholesteryl oleate were added as an internal standard and carrier respectively. The organic solvent was removed and the cells were washed with an additional 1.0 ml of hexane: isopropanol which was combined with the original extract. The cells were allowed to dry overnight, digested with 1.5 ml of 0.2N sodium hydroxide for 1 hour and an aliquot of the solubilized protein used for protein determination using the Lowry method. The organic extract was taken to dryness, the residue resuspended in 100 μl of chloroform and the lipids separated on silica gel impregnated glass fiber plates using a hexane:diethylether:acetic acid (170:30:1, v/v/v) solvent system. Individual lipids were visualized with iodine and the cholesteryl ester spot cut out and transferred to scintillation vials to determine the amount of radioactivity. The conversion of oleic acid to cholesteryl ester in the control averaged 0.54 mmol/hour/mg protein and was increased upon the addition of ac-LDL to about 10.69±0.69 mmol/hour/mg protein. The inhibition of esterification by the compounds is shown in Table 7; the data are expressed as the concentration at which ACAT activity is inhibited by 50% ($IC_{50}$). It should be noted that many of the intermediates had inhibitory activity in the in vitro ACAT assay and in the macrophage assay. For example, N-[5(4,5-diphenyl-1H-imidazol-2-ylthio)pentyl]-1-heptanaminehydrochloride had $IC_{50}$'s of 100 nM and 6 μM in the in vitro ACAT and macrophage assay, respectively.

C. Assay of Antihypercholesterolemic Activity in Cholesterol-fed Hamsters

Inhibition of ACAT activity in the gut reduces the absorption of cholesterol in cholesterol-fed animals. Hamsters weighing approximately 100 g, were maintained on a diet supplemented with 0.8% cholesterol. The treatment group received 1–100 mg/kg/day, p.o., of the test compound dissolved in 500 μl of corn oil for a period of two weeks. The control group were pair-fed to the treatment group and were dosed with 500 μl of the corn oil vehicle. At sacrifice, the hamsters were anesthetized with $CO_2$ and exsanguinated via cardiac puncture. Total serum cholesterol was determined on a Du Pont aca ® IV. The data were expressed in terms of mg cholesterol per 100 ml of serum (mg %). The antihypercholesterolemic activity of the compound of Example 1 is shown in Table 8.

TABLE 6

Inhibition of In Vitro Hepatic ACAT Activity by Various Compounds

| Compound of Example | In Vitro ACAT IC$_{50}$ (nM) |
|---|---|
| 1 | 13 |
| 2 | 3 |
| 3 | 8 |
| 4 | 60 |
| 5 | 12 |
| 6 | 3,600 |
| 7 | 41 |
| 8 | 10 |
| 9 | 930 |
| 20 | 20 |
| 53 | 17 |
| 64 | 30 |
| 71 | 16 |
| 85 | 60 |
| 94 | 10 |
| 97 | 25 |
| 105 | 20 |
| 107 | 1,000 |
| 110 | 60 |
| 114 | 40 |
| 118 | 170 |
| 122 | 80 |
| 137 | 76 |
| 160 | 490 |
| 186 | 2,850 |
| 188 | 20 |
| 189 | 70 |
| 190 | 30 |
| 192 | 70 |
| 193 | 60 |
| 194 | 1,900 |
| 195 | 40 |
| 196 | 300 |
| 197 | 119 |
| 198 | 40 |
| 199 | 20 |
| 200 | 710 |
| 201 | 200 |
| 202 | 220 |
| 205 | 74 |
| 204 | 500 |
| 206 | 40 |
| 207 | 9 |
| 208 | 20 |
| 209 | 1,400 |
| 210 | 17 |
| 211 | 32 |
| 212 | 60 |
| 258 | 40,000 |
| 261 | 80 |
| 262 | 200 |
| 263 | 40 |
| 266 | 230 |
| 276 | 58 |
| 278 | 8 |
| 281 | 16 |
| 298 | 30 |
| 299 | 140 |
| 300 | 130 |
| 338 | 3,500 |
| 339 | 280 |
| 340 | 25 |
| 341 | 3 |
| 342 | 30 |
| 343 | 160 |
| 344 | 30 |
| 345 | 60 |
| 346 | 50 |
| 347 | 30 |
| 348 | 700 |
| 349 | 200 |
| 350 | 605 |
| 351 | 250 |
| 352 | 300 |

TABLE 6-continued

Inhibition of In Vitro Hepatic ACAT Activity by Various Compounds

| Compound of Example | In Vitro ACAT IC$_{50}$ (nM) |
|---|---|
| 353 | 240 |
| 354 | 50 |
| 355 | 10 |
| 401 | 50 |
| 402 | 20 |
| 403 | 35 |
| 404 | 33 |
| 405 | 500 |
| 406 | 10 |
| 407 | 40 |
| 408 | 9 |
| 409 | 120 |
| 410 | 640 |
| 411 | 310 |
| 457 | 834 |
| 499 | 3,160 |

TABLE 7

Inhibition of Cholesterol Esterification in Macrophage by Various Compounds

| Compound of Example | Cholesterol Esterification IC$_{50}$ ($\mu$M) |
|---|---|
| 1 | 1.0 |
| 2 | 0.8 |
| 3 | 17.5 |
| 4 | 4.6 |
| 5 | 2.5 |
| 6 | 3.8 |
| 7 | 7.5 |
| 8 | 0.5 |
| 9 | 11.2 |
| 20 | 54.5 |
| 53 | 0.4 |
| 64 | 0.6 |
| 71 | 1.9 |
| 85 | 3.1 |
| 94 | 0.1 |
| 97 | 0.7 |
| 105 | 0.3 |
| 107 | 2.3 |
| 110 | 0.9 |
| 114 | 3.5 |
| 118 | 0.1 |
| 122 | 0.3 |
| 137 | 3.4 |
| 160 | 1.6 |
| 186 | 6.2 |
| 188 | 0.9 |
| 189 | 2.2 |
| 190 | 2.2 |
| 192 | 2.0 |
| 193 | 2.7 |
| 194 | 4.1 |
| 195 | 0.4 |
| 196 | 1.4 |
| 197 | 0.1 |
| 198 | 0.06 |
| 199 | 0.6 |
| 200 | 0.8 |
| 201 | 0.5 |
| 202 | 0.004 |
| 203 | 50.0 |
| 204 | 0.4 |
| 205 | 0.003 |
| 206 | 0.4 |
| 207 | 0.6 |
| 208 | 2.8 |
| 209 | 4.8 |
| 210 | 0.8 |
| 211 | 0.7 |
| 212 | 1.7 |
| 258 | 25.0 |
| 259 | 0.9 |

TABLE 7-continued

Inhibition of Cholesterol Esterification
in Macrophage by Various Compounds

| Compound of Example | Cholesterol Esterification IC$_{50}$ (μM) |
|---|---|
| 260 | 6.0 |
| 276 | 6.1 |
| 278 | 1.2 |
| 281 | 3.5 |
| 298 | 2.5 |
| 299 | 1.2 |
| 300 | 0.9 |
| 338 | 3.4 |
| 339 | 4.4 |
| 340 | 0.2 |
| 341 | 0.1 |
| 342 | 1.6 |
| 343 | 1.1 |
| 344 | 0.4 |
| 345 | 0.3 |
| 346 | 0.5 |
| 347 | 0.3 |
| 348 | 0.2 |
| 349 | 0.09 |
| 350 | 0.05 |
| 351 | 0.04 |
| 352 | 2.2 |
| 353 | 0.08 |
| 354 | 0.02 |
| 355 | 0.03 |
| 401 | 0.4 |
| 402 | 0.4 |
| 403 | 0.5 |
| 404 | 0.5 |
| 405 | 3.9 |
| 406 | 0.6 |
| 407 | 0.8 |
| 408 | 1.3 |
| 410 | 0.03 |
| 411 | 0.5 |
| 457 | 0.1 |
| 499 | 3.4 |

TABLE 8

Dose Response Evaluation of Example 1
in Hypercholesterolemic Hamsters

| Dose (mg/kg/day) | Serum Cholesterol (mg %)[a] Control | Serum Cholesterol (mg %)[a] Treated | Decrease (%) |
|---|---|---|---|
| 1 | 400 ± 25 | 295 ± 12 | 26 |
| 3 | 381 ± 17 | 279 ± 16 | 27 |
| 10 | 371 ± 7 | 201 ± 12 | 46 |
| 30 | 368 ± 15 | 197 ± 11 | 46 |
| 100 | 400 ± 17 | 62 ± 8 | 60 |

[a]Values are the mean ± SEM, n = 9–10 per group

Dosage Forms

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, 16th Edition, 1980.

In their therapeutic use as antihypercholesterolemic and/or antiatherosclerotic agents, the compounds of the invention are administered to the patient at dosage levels of 1 to 28 g per day. For a normal male adult human of approximately 70 kg of body weight, this translates into a dosage of 14 to 400 mg per kilogram body weight per day. The dosage administered will, of course, vary depending upon known factors such as the age, health, and weight of the recipient; nature and extent of symptoms, kind of concurrent treatment, frequency of treatment, and the effect desired. Useful pharmaceutical dosage forms for administration of the compounds of this invention can be illustrated as follows:

Tablets

Tablets are prepared by conventional procedures so that the dosage unit is 500 milligrams of active ingredient, 150 milligrams of lactose, 50 milligrams of cellulose and 10 milligrams of magnesium stearate.

Capsules

Capsules are prepared by conventional procedures so that the dosage unit is 500 milligrams of active ingredient, 100 milligrams of cellulose and 10 milligrams of magnesium stearate.

| Syrup | Wt. % |
|---|---|
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | Wt. % |
|---|---|
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendible Powder | Wt. % |
|---|---|
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Colorant, Flavor and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Colorant, Flavor and Preservative | as required |
| Water | as required |

Gelcarin ® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogeneous paste.

The term "consisting essentially of" in the present disclosure is intended to have its customary meaning; namely, that all specified materials and conditions are very important in practicing the invention but that unspecified materials and conditions are not excluded so long as they do not prevent the benefits of the invention from being realized.

The foregoing disclosure includes all the information deemed essential to enable those of skill in the art to practice the claimed invention. Because the cited publications and applications may provide further useful information, however, these cited materials are hereby incorporated by reference.

What is claimed is:

1. A method of treating hypercholesterolemia or atherosclerosis in a mammal comprising administering to the mammal a therapeutically effective amount of a compound of the formula

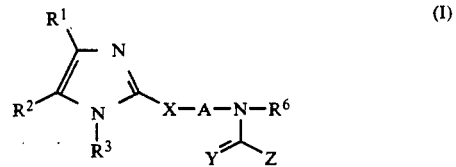

wherein
$R^1$ and $R^2$ are selected independently from H, $C_1$-$C_8$ unbranched alkyl, $C_3$-$C_8$ branched alkyl, $C_3$-$C_7$ cycloalkyl, $C_4$-$C_{10}$ cycloalkylakyl, $C_7$-$C_{14}$ araalkyl, 2-, 3-, or 4-pyridyl, 2-thienyl, 2-furanyl phenyl optionally substituted with 1 to 3 groups selected from F, Cl, Br, OH, $C_1$-$C_4$ alkoxy, $C_1$-$C_4$ alkyl, $C_3$-$C_8$ branched alkyl, $CH_3S(O)_r$, $NO_2$, $CF_3$ or $NR^7R^8$;

$R^3$ is H, $C_1$-$C_6$ alkyl, allyl, benzyl, or phenyl optionally substituted with F, Cl, $CH_3$, $CH_3O$, or $CF_3$;

$R^4$ is straight chain $C_1$-$C_8$ alkyl optionally substituted with F; $C_3$-$C_8$ branched alkyl, $C_3$-$C_7$ cycloalkyl, $C_4$-$C_{10}$ cycloalkylalkyl, $C_7$-$C_{14}$ araalkyl where the aryl group is optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^7R^8$, or $NCOR^7$; $C_3$-$C_6$ alkenyl or alkynyl, $C_1$-$C_3$ perfluoroalkyl, phenyl optionally substituted with 1 to 3 groups selected from $C_1$-$C_4$ alkyl, $C_3$-$C_8$ branched alkyl, $C_1$-$C_4$ alkoxy, F, Br, Cl, $NH_2$, OH, CN, $CO_2H$, $CF_3$, $NO_2$, $C_1$-$C_4$ carboalkoxy, $NR^7R^8$ or $NCOR^7$; pentafluorophenyl, benzyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^7R^8$, or $NCOR^7$; or biphenyl;

$R^5$ is H, $C_1$-$C_6$ alkyl, or benzyl;

$R^6$ is $C_1$-$C_8$ alkyl, $C_3$-$C_8$ branched alkyl, $C_3$-$C_7$ cycloalkyl, $C_3$-$C_8$ alkenyl or alkynyl, phenyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^7R^8$, or $NCOR^7$; pentafluorophenyl, benzyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^7R^8$, or $NCOR^7$;

$R^7$ and $R^8$ are selected independently from H or $C_1$-$C_4$ alkyl;

X is $S(O)_r$;

A is $C_2$-$C_{10}$ branched alkyl, $C_3$-$C_{10}$ alkenyl, or $C_3$-$C_{10}$ alkynyl;

Y is O;

Z is $NHR^4$, $OR^4$, or $R^4$;

r is 0–2, or a pharmaceutically acceptable salt thereof.

2. A method of treating hypercholesterolemia or atherosclerosis in a mammal comprising administering to the mammal a therapeutically effective amount of the compound N-[5-(4,5-diphenyl-1H-imidazole-2-ylthio)-pentyl]-N-heptylbutanamide.

3. A method of treating hypercholesterolemia or atherosclerosis in a mammal comprising administering to the mammal a therapeutically effective amount of the compound N-[5-[4,5-bis(1-methylethyl)-1H-imidazole-2-ylthio]pentyl]-N-heptylcyclohexaneacetamide.

4. A method of treating hypercholesterolemia or atherosclerosis in a mammal comprising administering to the mammal a therapeutically effective amount of the compound [N-[5[4,5-bis(4-methoxyphenyl)-1H-imidazole-2-ylthio]pentyl]-2,4-difluoro-N-heptylbenzeneacetamide.

5. The method of claim 1 wherein
$R^1$ and $R^2$ are selected independently from $C_1$-$C_8$ unbranched alkyl, $C_3$-$C_8$ branched alkyl, $C_3$-$C_7$ cycloalkyl, $C_4$-$C_{10}$ cycloalkylalkyl, $C_7$-$C_{14}$ araalkyl, 2-, 3-, or 4-pyridinyl, 2-thienyl, 2-furanyl, phenyl optionally substituted with 1 to 2 groups selected from F, Cl, Br, OH, $C_1$-$C_4$ alkoxy, $C_1$-$C_4$ alkyl, $C_3$-$C_8$ branched alkyl, $CH_3S(O)_r$, $NO_2$, or $NR^7R^8$.

6. The method of claim 5 wherein
$R^3$ is H, $CH_3$ is phenyl;
$R^6$ is $C_1$-$C_8$ alkyl, $C_3$-$C_8$ branched alkyl, $C_3$-$C_7$ cycloalkyl, phenyl optionally substituted with 1 to 3 groups selected from $CH_3$, $CH_3O$, F, Br, Cl, $NH_2$, OH, CN, $CO_2H$, $CF_3$, or di($C_1$-$C_4$)alkylamino; or benzyl optionally substituted with 1 to 3 groups selected from $CH_3$, $CH_3O$, F, Br, Cl, $NH_2$, OH, CN, $CO_2H$, $CF_3$, or di($C_1$-$C_4$)alkylamino;
X is $S(O)_r$;
A is $C_2$-$C_{10}$ alkyl, $C_4$-$C_9$ branched alkyl.

7. The method of claim 5, wherein
$R^1$ and $R^2$ are selected from $C_1$-$C_8$ unbranched alkyl, $C_3$-$C_8$ branched alkyl, $C_3$-$C_7$ cycloalkyl, $C_4$-$C_{10}$ cycloalkylalkyl, $C_7$-$C_{14}$ araalkyl, 2-, 3-, or 4-pyridinyl, 2-thienyl, or phenyl optionally substituted with 1 to 2 groups selected from F, Br, Cl, $C_1$-$C_4$ alkyl, $C_3$-$C_8$ branched alkyl, $CH_3O$, $CH_3S(O)_r$, $NO_2$, or di-$C_1$-$C_4$ alkylamino.

8. The method of claim 7 wherein
$R^1$ and $R^2$ are selected independently from $C_1$-$C_8$ unbranched alkyl, $C_3$-$C_8$ branched alkyl, $C_3$-$C_7$ cycloalkyl, $C_4$-$C_{10}$ cycloalkylalkyl, $C_7$-$C_{14}$ araalkyl, 2-thienyl, 2-furanyl, phenyl optionally substituted with 1 to 2 groups selected from F, Cl, Br, OH, $C_1$-$C_4$ alkoxy, $C_1$-$C_4$ alkyl, $C_3$-$C_8$ branched alkyl, $CH_3S(O)_r$, $NO_2$, or $NR^7R^8$.

9. The method of claim 8 wherein
$R^3$ is H, $CH_3$, phenyl;
$R^6$ is $C_1$-$C_8$ alkyl, $C_3$-$C_8$ branched alkyl, $C_3$-$C_7$ cycloalkyl, phenyl optionally substituted with 1 to 3 groups selected from $CH_3$, $CH_3O$, F, Br, Cl, $NH_2$, OH, CN, $CO_2H$, $CF_3$, or di($C_1$-$C_4$)alkylamino; or benzyl optionally substituted with 1 to 3 groups selected from $CH_3$, $CH_3O$, F, Br, Cl, $NH_2$, OH, CN, $CO_2H$, $CF_3$, or di($C_1$-$C_4$)alkylamino.

10. The method of claim 9 wherein
$R^1$ and $R^2$ are selected independently from $C_1$-$C_8$ unbranched alkyl, $C_3$-$C_8$ branched alkyl, $C_3$-$C_7$ cycloalkyl, $C_4$-$C_{10}$ cycloalkylalkyl, $C_7$-$C_{14}$ araalkyl, 2-thienyl, or phenyl optionally substituted with 1 to 2 groups selected from F, Br, Cl, $C_1$-$C_4$ alkyl, $C_3$-$C_8$ branched alkyl, $CH_3O$, $CH_3S(O)_r$, $NO_2$, or di($C_1$-$C_4$)alkylamino.

* * * * *